(12) United States Patent
Aguillon Gutierrez et al.

(10) Patent No.: US 11,618,904 B2
(45) Date of Patent: Apr. 4, 2023

(54) PROMOTER WITH AN ENRICHED CYTOSINE-GUANINE DINUCLEOTIDE REGION, VECTORS, CELLULAR LINES, METHOD FOR PRODUCING RECOMBINANT PROTEIN

(71) Applicants: UNIVERSIDAD DE CHILE, Santiago (CL); BPH S.A., Santiago (CL); INGENIERIA ORBICORP LTDA, Santiago (CL)

(72) Inventors: Juan Carlos Aguillon Gutierrez, Santiago (CL); Maria Carmen Molina Sampayo, Santiago (CL); Roberto Aquiles Zuñiga Olate, Santiago (CL); Matias Fernando Guitierrez Gonzalez, Santiago (CL); Norberto Andres Collazo Muñoz, Santiago (CL); Jaime Camilo Teneb Lobos, Santiago (CL)

(73) Assignees: UNIVERSIDAD DE CHILE, Santiago (CL); BPH S.A., Santiago (CL); INGENERIA ORBICORP LTDA, Santiago (CL)

( * ) Notice: Subject to any disclaimer, the term of this patent is extended or adjusted under 35 U.S.C. 154(b) by 1131 days.

(21) Appl. No.: 16/314,192

(22) PCT Filed: Jun. 9, 2017

(86) PCT No.: PCT/CL2017/050024
§ 371 (c)(1),
(2) Date: Dec. 28, 2018

(87) PCT Pub. No.: WO2018/000105
PCT Pub. Date: Jan. 4, 2018

(65) Prior Publication Data
US 2019/0309323 A1  Oct. 10, 2019

(30) Foreign Application Priority Data
Jun. 29, 2016 (CL) .................... 1661-2016

(51) Int. Cl.
*C12N 15/85* (2006.01)
*C07K 16/24* (2006.01)
*C12N 5/10* (2006.01)

(52) U.S. Cl.
CPC ............ *C12N 15/85* (2013.01); *C07K 16/241* (2013.01); *C12N 5/10* (2013.01); *C12N 2710/16143* (2013.01); *C12N 2830/60* (2013.01)

(58) Field of Classification Search
CPC .................................................. C12N 15/85
See application file for complete search history.

(56) References Cited

U.S. PATENT DOCUMENTS

| 5,512,483 A | 4/1996 | Mader et al. |
| 2003/0166890 A1 | 9/2003 | Crombie et al. |
| 2009/0156498 A1 | 6/2009 | Pardridge et al. |
| 2012/0258541 A1 | 10/2012 | Mauro et al. |

FOREIGN PATENT DOCUMENTS

| EP | 1639112 A2 | 3/2006 |
| WO | 2005/000888 A2 | 1/2005 |
| WO | 2007/123489 A1 | 11/2007 |
| WO | 2011/083175 A1 | 7/2011 |
| WO | 2012/074277 A2 | 6/2012 |
| WO | 2012/087246 A1 | 6/2012 |
| WO | 2015/033086 A1 | 3/2015 |
| WO | 2015/102487 A1 | 7/2015 |
| WO | 2016/062837 A1 | 4/2016 |
| WO | 2017/062724 A1 | 4/2017 |

OTHER PUBLICATIONS

David I. Israel, et al; "Highly inducible expression from vectors containing multiple GRE's in CHO cells overexpressing the glucocorticoid receptor", Nucleic Acids Research; vol. 17, No. 12, Jun. 26, 1989; pp. 4589-4604.
Jiandong Li, et al; "A comparative study of different vector designs for the mammalian expression of recombinant IgG antibodies", Journal of Immunological Methods 318; pp. 113-124, Jan. 10, 2007.
Mariati; "Insertion of Core CpG Island Element into Human CMV Promoter for Enhancing Recombinant Protein Expression Stability in CHO cells", Biotechnology Progress; May-Jun. 2014; 30(3): pp. 523-534; Epub May 10, 2014.
Bo Wang, et al; "Structural comparision of two anti-CD20 monoclonal antibody drug products using middle-down mass spectrometry", Analyst; May 21, 2013; 138(10): 3058-65.
International Search Report dated Sep. 15, 2017; PCT/CL2017/050024.
Written Opinon dated Sep. 15, 2017; PCT/CL2017/050024.
Chilean First office action 201601661.
Chilean Second Office Action; 201601661.

*Primary Examiner* — Antonio Galisteo Gonzalez
(74) *Attorney, Agent, or Firm* — Procopio, Cory, Hargreaves & Savitch LLP

(57) ABSTRACT

The present invention relates to the field of genetic engineering, preferably the expression of recombinant proteins (RP). In particular, the invention relates to a promoter and variants thereof having an equal function and more than 90% sequence identity. The promoter comprises a fragment of 1147 base pairs (bp) of a first promoter, promoter of the β-actin gene of the *Cricetulus griseus* genome, enriched in cytosine-guanine dinucleotides (RegCG). The first promoter can be upstream of a second promoter, cytomegalovirus (CMV) promoter. The invention also relates to vectors, transfected cellular lines and a method for producing RP in mammal cells that have been transfected with vectors containing said promoter or variants thereof.

19 Claims, 8 Drawing Sheets

Specification includes a Sequence Listing.

PROMOTER WITH AN ENRICHED CYTOSINE-GUANINE DINUCLEOTIDE REGION, VECTORS, CELLULAR LINES, METHOD FOR PRODUCING RECOMBINANT PROTEIN

FIELD OF THE INVENTION

The present invention relates to the field of genetic engineering, preferably the expression of recombinant proteins (RP). Particularly, the invention relates to a promoter and variants thereof having the same function and having more than 90% sequence identity. The promoter comprises a fragment of 1147 base pairs (bp) of a first promoter, gene β-actin of the genome *Cricetulus griseus*, enriched in Cytosine-Guanine dinucleotides (RegCG), which may be upstream of a second promoter, cytomegalovirus (CMV). The invention also comprises vectors, transfected cell lines, and method for producing RP in mammalian cells which have been transfected with vectors containing the aforementioned promoter or variants thereof.

BACKGROUND

By means of genetic engineering, different RP having therapeutic application have been generated, also known as biopharmaceuticals. Within the RP, therapeutic antibodies (TpAb) have been developed, whose most successful applications are in the treatment of cancer and autoimmune diseases.

Although the marketing of TpAb generates high economic activity, an explosion in the generation of new TpAb is expected with the discovery of new therapeutic targets. In addition, the fact that TpAb should be administered in high doses for long periods further increases the demand for them. Although there has been a great development of bioprocesses and bioreactors for RP expression in mammalian cells (CHO-Chinese hamster ovary, NS02 and HEK) in recent years, significantly increasing production, this has not been enough to meet the growing demand for RP. It is for this reason that many efforts have focused on improving the productive capacity of the cells at different levels. Thus, it is now known that protein expression can be increased, both by changing the genetic level of cell lines so as to increase their viability, gene expression, folding efficiency and secretory capacity, and by optimizing the conditions of the cell cultures, allowing increased production of RP along with increased survival and cell density thereof.

Among the closest patents documents, it can be mentioned CL200400189 (Immuno Japan Inc.) that teaches an expression vector which allows to easily obtain strains of high level of recombinant protein production using mammalian cells, especially Chinese hamster ovary cells as a guest. The vector comprises a promoter with highly inducible expression, a multiple cloning site for insertion of a gene, and a polyadenylation signal sequence, in that order, from above, and further comprising a drug resistant gene below them.

CL19890089 teaches a process for the preparation of hybrid fusion proteins composed of human interleukin-2 (IL-2) and *pseudomonas* exotoxin by recombinant DNA technology. Exotoxin is at the carboxyl end and IL-2 at the amino terminus, and comprises transforming a host organism with a recombinant vector. The host thus transformed is cultivated in a suitable medium and the hybrid protein is purified. The hybrid protein (IL2-pe 40) can be used to treat autoimmune diseases and to suppress the immune response in cases of graft rejection and transplants. Production of recombinant human IL-2 fusion proteins can be substantially enhanced by utilizing a construction vector capable of expressing the hybrid protein at high levels. Moreover, the resulting protein can be purified at a high yield using an affinity column with the receptor. In a specific embodiment, the fusion protein of the IL-2 and *Pseudomonas* exotoxin is expressed at high levels in *E. coli*. The vector is useful for treating autoimmune diseases such as thyroiditis, type 1 diabetes, rheumatoid arthritis.

US201139339 teaches vectors, transfected cell lines, mammalian host cells (particularly Chinese hamster ovary (CHO) cells) for protein production, where transfection efficiency is based on the use of: a single vector, functional sequences in oriP, codons optimized for Epstein-Barr nuclear antigen-1 virus (EBNA1), poly(ethyleneimine) 40 kDa fully deacetylated as a transfection reagent, co-expression of a fibroblast growth factor (FGF) and/or using protein kinase B to enhance and improve heterologous gene expression by valproic acid (VPA).

JP2011019509 (TOYOBO CO LTD) provides an expression vector containing a multi-cloning site optimized to allow cloning of the gene of a target protein with good efficiency, by introducing the expression vector into animal cells and establishment of cell showing a high productivity of the recombinant protein. This expression vector has a multi-cloning site with a restriction enzyme recognition sequence having a low frequency of occurrence in the gene of the target protein, especially an antibody gene, a cassette selection marker gene expression resistance to a mRNA-destabilizing, and at least one gene expression sequence of stabilization.

US20110081708 relates to a method for boosting recombinant gene expression in bacteria, yeast, insect and mammalian cells. This method generally considered most or all of the parameters and factors affecting protein expression including codon usage, use of tRNA, GC content, ribosome binding sequences, promoter, 5'-UTR sequences, ORF and 3'-UTR of genes to increase protein expression of genes in bacteria, yeast, insect and mammalian cells. In particular, the invention relates to a system and method for optimizing the sequence of recombinant protein expression improves with the use of algorithms, and therefore the method can be incorporated into software.

US2011097798 discloses the use of expression vectors of a target cDNA of at least one selective marker gene of a single cassette of mammalian expression is under the control of a promoter compound, said cDNA and at least one marker gene are associated by IRES element, an expression vector comprising also protects; a promoter compound, at least one cloning site the gene target insert, an IRES, a bacterial expression promoter EM7 a selective marker gene, a transcription terminator, a pUC origin of high amplification copy and at least one element a region associated with the nuclear matrix (MAR). Also, it mentions as elements to optimize promoter, the start site of transcription (TSS), the TATA box in TFIID complex element recognition factor II B, TFIIB, among others.

EP2316955 relates to a system and method for the production of proteins comprising the use of animals or plants which modify protein folding or processing capacity, and involves the co-expression of a polypeptide which significantly increases the yield in cells of the protein of interest. Such co-expressed polypeptide may be a component or modulator XBP1 or ATF6.

WO2010092335 relates to a modified recombinant host cell to increase expression levels of Ero1 and XBP1 relative to expression levels in XBP1 and Ero1 in an unmodified cell. It also relates to a method for producing a recombinant protein of interest, wherein the yield of the protein of interest is increased, increasing the ability of the cell to perform post-translational modifications. The method may be initiated or positively regulated through UPR. Also, it mentions that the modified cell increases expression of Ero1 and XBP1. The method is used to produce recombinant antibodies such as proteins or fragments thereof.

US20100120089 describes an inducible expression cassette comprising a high promoter gene dihydrofolate reductase (DHFR) with GC-rich repeat sequences, which are partially or completely removed, to enhance the effectiveness of a gene amplification system. An expression vector comprising such a cassette and optionally a gene encoding a recombinant protein of interest, a line of animals transformed with the vector cells, and a method of mass production and purification of a recombinant protein by means of culturing the transformant. The invention enables reducing the time needed to establish a cell line that produces at high levels, a recombinant protein of interest with a low concentration of DHFR inhibitor, which allows more efficient production of the recombinant protein.

KR20080016871 relates to a mammalian host cell with a high expression level of a recombinant antibody containing a double gene vector sequences optimized nucleotide encoding the light chain and the antibody heavy chain, and a process for improving the production of recombinant antibodies in a mammalian host cell. The vector comprises at least a first transcription unit containing a first sequence of synthetic nucleotides encoding a first polypeptide chain and a second transcription unit containing a second synthetic nucleotide sequence encoding a second polypeptide chain where both synthetic sequences They are based on the nucleotide sequences of natural origin, wherein the first and second nucleotide sequence is adapted to genes of CHO cells, wherein the mammals expression vector, the two synthetic nucleotide sequences have a GC content and/or GC distribution, which is different from the corresponding natural nucleotides sequences.

US20070141557 relates to a method for optimizing the expression of a nucleotide sequence based on the amino acid sequence of a protein, and device for carrying out said method. An important variable of the invention is the GC content (guanine and cytosine bases), repeating DNA motifs, or the repeating complementary reverse sequence.

WO0069881 refers to an estrogen response element binding protein called (ERE-BP), and isolated polynucleotides encoding said protein. Vectors, host cells, recombinant methods for producing the protein, transgenic animals and antibody are also provided. The invention relates to therapeutic methods and treatment of disorders related to the mentioned protein. It also provides an isolated nucleic acid encoding said mammalian estrogen response element binding protein (ERE-BPs), and fragments thereof.

U.S. Pat. No. 8,298,816B2 provides a hybrid promoter comprising a combination of a CMV enhancer promoter and a beta-actin or mammalian transcriptional regulatory region of the genomic sequence post Woodchuck Hepatitis Virus (WPRE) and a mammalian beta-actin promoter that is stronger than existing promoters. In addition, the activities of beta-actin promoters could be enhancers by co-expressing the oncogene Ras product, which is a transactivator.

US20130174284A1 relates to a recombinant vector and a transgenic mouse expressing human ferritin in tissue in a non specific manner, and more particularly, to a vector prepared for operably linking a gene of human ferritin to an early enhancer of the cytomegalovirus (CMV) promoter and a beta-actin promoter. Furthermore, the invention relates to a method for preparing a transgenic mouse and a method for monitoring cell or tissue therapy using the transgenic mouse.

US20130273634A1 discloses a method for mass production of human coagulation factor VII. The method includes a) providing an expression vector which carries i) an empty dihydrofolate reductase promoter of one or more repeated CCGCC sequences from a GC rich region thereof, and a dihydrofolate reductase (DHFR) gene operably linked to it, and ii) a cytomegalovirus (CMV) promoter and human coagulation factor VII gene to it; b) obtaining a transformed host cell line containing the expression vector; c) culturing the transfected host cell in the presence of an inhibitor of dihydrofolate reductase to select cells expressing the human coagulation factor VII with high efficiency; d) adding sodium butyrate to the selected host cells.

US20130324593A1 relates to a hybrid promoter wherein all or part of a CMV enhancer, all or part of a beta-actin promoter, all or part of a CMV promoter, and all or part of a beta-actin intron are operatively connected to each other, a recombinant vector comprising the same, a transformant, a pharmaceutical composition comprising the recombinant vector or the transformant, and a method for preparing a target protein using the recombinant vector or the transformant. The hybrid promoter of the invention is capable of inducing high expression of a target protein in a eukaryotic cell. Then, the hybrid promoter of the invention can be effectively used for the development of an antibody or the production of a DNA vaccine.

US20140017726A1 relates to a nucleic acid molecule comprising a promoter functional herpesvirus, functional enhancer of herpesvirus, and one or more inner elements of the CpG island of phosphoribosyltransferase gene and/or a functional variant thereof. A method of producing the desired polypeptide using the nucleic acid molecule, a vector and a host cell containing the nucleic acid molecule are also disclosed.

KR20120059222A discloses a fusion promoter that is operably linked partially or completely to a CMV promoter, and partially or completely to a beta-actin intron maintaining high expression by a target gene. The fusion protein is operably linked, partially or completely, to a promoter or a beta-actin intron. The CMV promoter contains a DNA fragment of specific sequence. The beta-actin intron containing said DNA fragment of specific sequence. The recombinant vector contains a fusion promoter containing an ampicillin, kamicina or chloramphenicol antibiotic resistant acetyl transferase gene. Pharmaceutical composition containing the vector or recombinant host cell transformed with the recombinant vector.

KR20050018720 teaches an oligonucleotide to activate cytomegalovirus (CMV) and method to activate it. The invention solves problems such as the difficulty of in vivo activation of CMV promoter and CMV inactivation by interferon when the CMV promoter is applied to gene therapy.

"High-level protein expression in CHO transient transfection scalable", Ye J, Kober V, Tellers M, Naji Z, Salmon P, Markusen J F, Journal: Biotech Bioeng. 2009 Jun. 15: 103 (3); 542-51 discloses Chinese hamster ovary (CHO) cells that have been widely used as the platform production of therapeutic proteins, including monoclonal antibodies in the pharmaceutical industry. For early development, it is advantageous to rapidly produce large amounts of protein in the same cell line. Therefore, the development of a platform of transiently transfected CHO cells with a high level of protein expression is highly desirable. The publication develops such a platform. Polyethyleneimine (PEI) was used as transfection reagent. It was found that DMSO and lithium acetate (LiAc) levels improve transient expression of transfection significantly in CHO cells. With an optimized process of transient transfection, the monoclonal antibody (Mab) was expressed in CHO cells at a high level, with an average of 80 mg/L.

"Endogenous estrogen receptor is transcriptionally active in primary beta cells from ovarian estrogen receptor knockout mice", S O Mueller, Katzenellenbogen J A, Korach K S., Steroids. 2004 September; 69 (10): 681-6 teaches that an estrogen receptor (ER) alpha is an transcription factor inducible by the hormone having a key physiological role. Interestingly, a clear and indisputable physiological function of the recently described ERβ remains difficult, with the exception of the ovary, where it has been a proven cooperative role of ERα and ERβ. It investigates the endogenous environmental requirements which act as inducible transcription factors. It also studies selective agonist potency ERβ R-indenestrol-A, the pure ERα agonist and antagonist ERβ R, R-diethyl tetrahidrocriseno, and pure ERα agonist propylpyrazole triol.

BRIEF DESCRIPTION OF THE INVENTION

The present invention relates to the field of genetic engineering and protein expression, preferably recombinant proteins (RP). Particularly, the invention relates to a promoter and variants thereof having the same function and more than 90% sequence identity. Preferably, such variants have more than 95% sequence identity. Even more preferably, such variants have more than 98% sequence identity. Even more preferably, such variants have more than 99% sequence identity. The promoter comprises a promoter which is a fragment of 1147 bp of promoter sequence of β-actin genome *Cricetulus griseus*, rich in cytosine-guanine dinucleotides (RegCG) sequence SEQ ID NO: 5, which may be upstream of the CMV promoter. The invention also comprises vectors, transfected cell lines, methods for producing such vectors and cell lines, and method for producing RP in mammalian cells which have been transfected with vectors containing the aforementioned promoter or variants.

The present invention optionally proposes incorporating RegCG (SEQ ID NO: 5), upstream of the CMV promoter expression vectors, to prevent silencing of the latter, thus improving the RP expression levels in mammalian cells, preferably CHO cells. Thus, an expression system more efficient (4.5 times), with respect to commercial viral vectors, in the production yield of Recombinant Antibodies (RAb).

In addition, this optimized expression system may allow the development of new biopharmaceuticals and/or biogenerics.

DETAILED DESCRIPTION OF THE INVENTION

Figure 1:
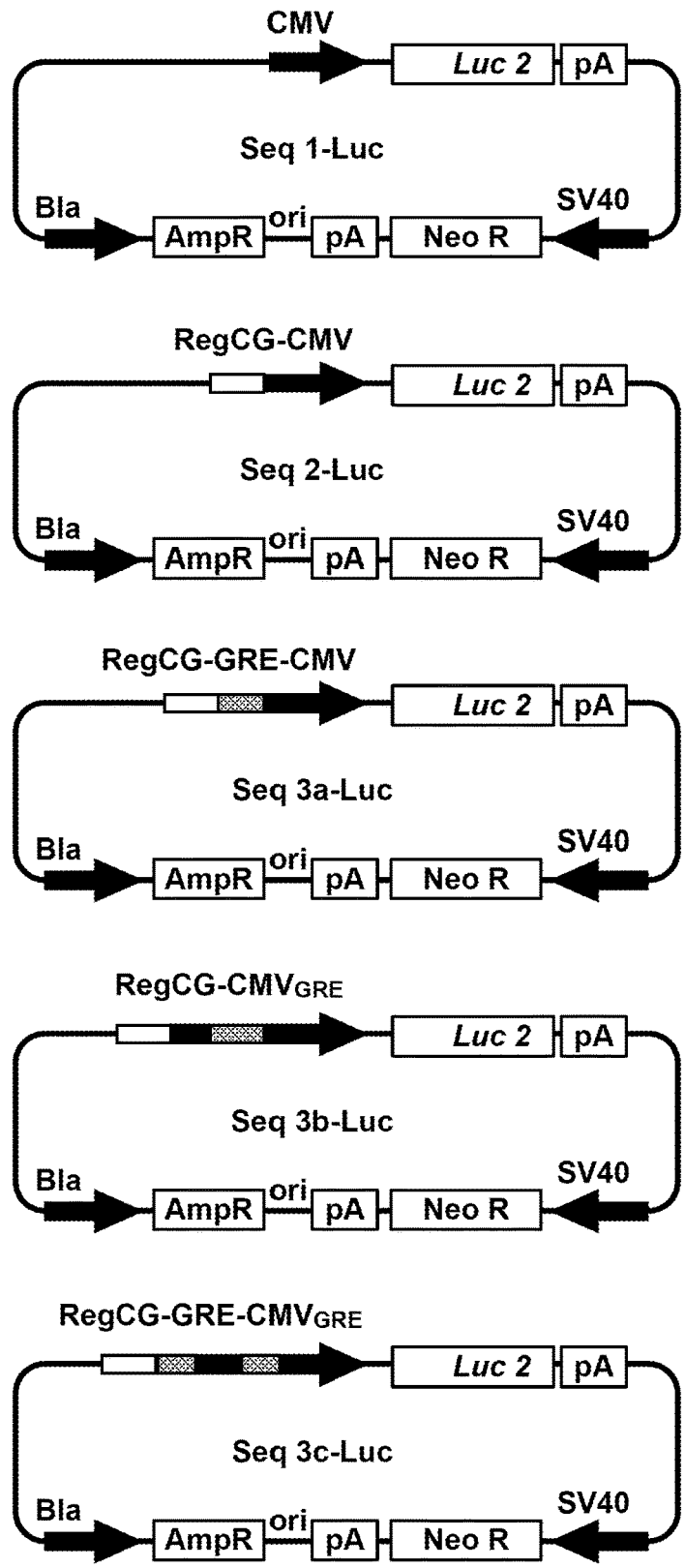
FIG. 1 shows a diagram of promoter variants in reporter vectors, cloned in vector pGL4.17 (SEQ ID NO: 1) encoding for the luciferase protein (Luc2). Seq1-Luc vector (SEQ ID NO: 2) comprises the promoter region CMV (SEQ ID NO: 3), used as a control; the Seq2-Luc vector (SEQ ID NO: 4) comprises RegCG (SEQ ID NO: 5) upstream of the CMV promoter region to form the RegCG-CMV promoter (SEQ ID NO: 6); Seq3a-Luc vector (SEQ ID NO: 7) comprises a tandem of 5 glucocorticoid response elements (GRE) (SEQ ID NO: 8) incorporated in the RegCG-CMV promoter, and CMV between RegCG forming RegCG-GRE-CMV (SEQ ID NO: 9). The vector Seq3b-Luc (SEQ ID NO: 10), contains GRE between the enhancer (SEQ ID NO: 29) and the core of CMV (SEQ ID NO: 30), forming RegCG-CMV-GRE (SEQ ID NO: 11). Seq3c-Luc (SEQ ID NO: 12) contains a GRE between RegCG and CMV; and another GRE between the enhancer and the core of CMV forming RegCG-GRE-CMV-GRE (SEQ ID NO: 13).
Figure 2:
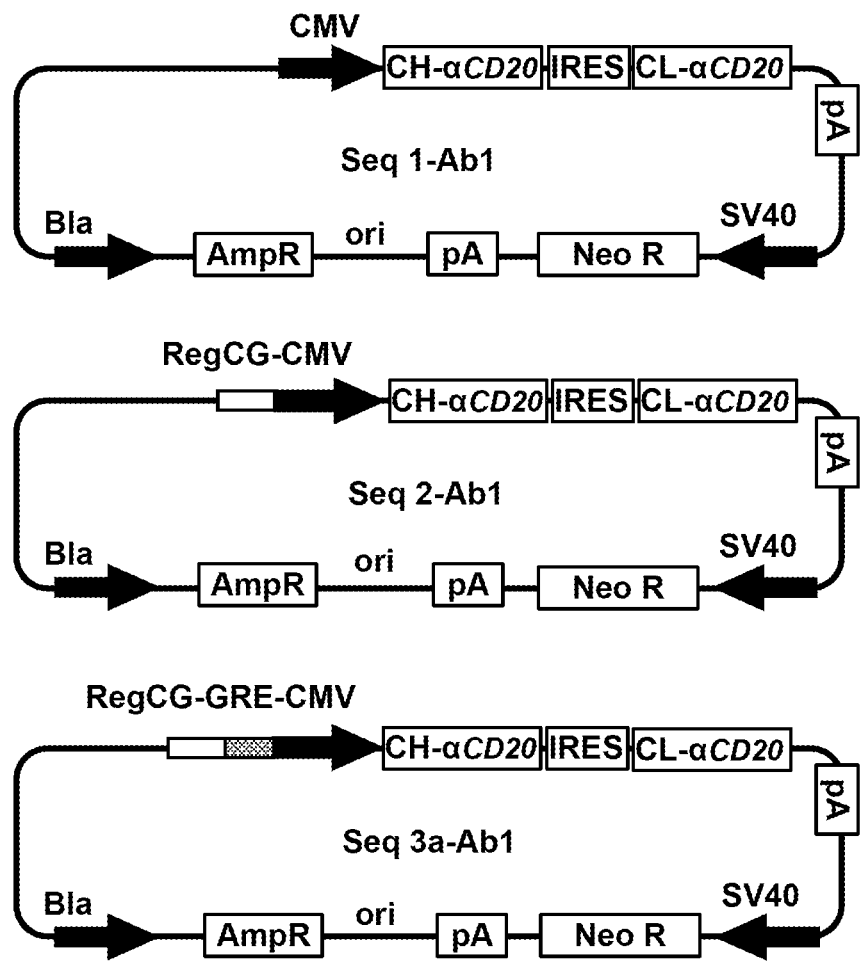
FIG. 2 shows a diagram of promoter variants in expression vectors, cloned in pcDNA 3.1 vector (−) (SEQ ID NO: 14) encoding the Ab1 antibody. The Ab1 antibody is encoded by the genes of the heavy (SEQ ID NO: 15) and light (SEQ ID NO: 16) chains separated by an IRES (SEQ ID NO: 17), forming CH-αCD20-IRES-CL-αCD20 (SEQ ID NO: 18). The vector Seq1-Ab1 (SEQ ID NO: 19) comprises the promoter region CMV (SEQ ID NO: 3), used as a control; vector Seq2-Ab1 (SEQ ID NO: 20) comprises RegCG (SEQ ID NO: 5) upstream of the CMV promoter region to form the RegCG-CMV promoter (SEQ ID NO: 6); the vector Seq3a-Ab1 (SEQ ID NO: 21) comprises a tandem of 5 glucocorticoid response elements (GRE) (SEQ ID NO: 8) incorporated in the RegCG-CMV promoter, between RegCG and CMV, forming RegCG-GRE-CMV (SEQ ID NO: 9).

The present invention relates to a promoter and variants thereof having the same function and more than 90% sequence identity. Preferably, such variants have more than 95% sequence identity. Even more preferably, such variants have more than 98% sequence identity. Even more preferably, such variants have more than 99% sequence identity. The promoter comprises a promoter which is a fragment of 1147 bp of promoter sequence of β-actin of the genome *Cricetulus griseus*, enriched in citosine-guanine dinucleotides (RegCG) sequence SEQ ID NO: 5, which may be upstream of the CMV promoter. The invention also comprises vectors, transfected cell lines, methods for producing such vectors and cell lines, and method for producing RP in mammalian cells which have been transfected with vectors containing the aforementioned promoter or variants. The present invention optionally proposes incorporating RegCG (SEQ ID NO: 5), upstream of the CMV promoter expression vectors, to prevent silencing of the latter, thus improving the RP expression levels in mammalian cells, preferably CHO cells. Thus, the present invention proposes an expression system more efficient (4.5 times), with respect to commercial viral vectors, in the production yield of Recombinant Antibodies (AcR).

Thus, the present invention incorporates a 1147 bp fragment of the promoter sequence of β-actin of the genome *Cricetulus griseus*, enriched in cytokine-guanine dinucleotides (RegCG) sequence SEQ ID NO: 5 and Ab2 in CHO cells transfected with the vector generated in the present invention, where Ab1 corresponds to a human anti-CD20 antibody whose light chain sequence (SEQ ID NO: 31) and heavy chain sequence (SEQ ID NO: 32) are identical to those of the commercial antibody Rituximab, and where Ab2 corresponds to a human anti-TNF antibody whose light chain sequence (SEQ ID NO: 33) and heavy chain sequence (SEQ ID NO: 34) correspond to the sequences of an antibody registered in Chilean patent 50,500.

For incorporation of the expression vector to a mammalian cell, any technique of inserting DNA known in the art, such as transfection, viral transduction among others may be used, including those widely established techniques, such as electroporation, coprecipitation with phosphate calcium, lipofection, and others. In addition, transfection can be performed in a transient or stable manner, where transient transfection is defined as the one in which no selective pressure on the cells is performed, maintaining the vector episomally therein.

On the other hand, stable transfection involves the integration of the vector to the genomic DNA of the cells, either by non-homologous recombination, or by site-directed additions. Cells performing this addition can be selected using a marker in the vector, which can also allow the amplification of the copy number of the vector in the genome of the host cell.

For the generation of this promoter, the early cytomegalovirus promoter sequence (CMV) (SEQ ID NO: 3) was used as the basis because it has high transcriptional activity and is widely used for RP expression in animal cells. However, this promoter is frequently silenced in production lines, resulting in low productivity clones of PR. Therefore, in order to avoid such silencing, a region of 1147 bp (SEQ ID NO: 5) derived from a CpG island was incorporated upstream of the promoter, which was designated RegCG. RegCG can be immediately upstream of the promoter or alternatively separated from this by a segment, for example, a segment of 187 bp (SEQ ID NO: 8). In the latter case, the spacer segment contains glucocorticoid recognition elements (GREs) in order to generate an adjustable mechanism of protein production by the addition of a glucocortidoid such as dexamethasone in the culture medium; whose presence does not affect the decrease of promoter silencing, maintaining its basal activity in the absence of the inducer.

Figure 4:
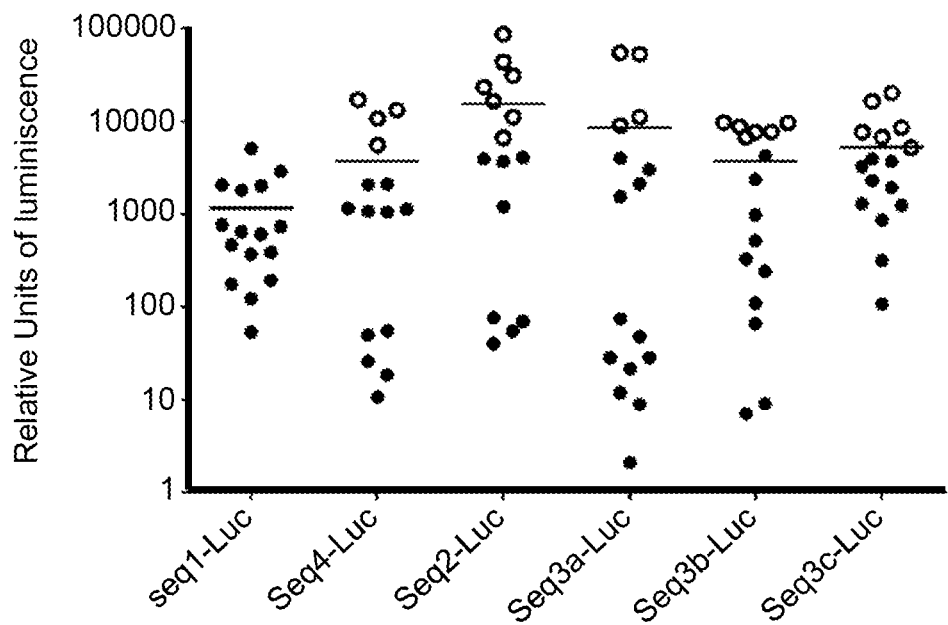
FIG. 4 shows the effect of RegCG in combination with GRE on transcriptional activity of the CMV promoter in stable cell lines. The promoter activity was expressed in relative luminescence units (RLU) calculated as the ratio of the luminescence and total protein concentration in cell lysates. The dots indicate the activity of each clone, also showing the average activity for each measurement. The empty circles correspond to clones having higher average clones with Seq1-Luc plus 3 standard deviations activity.

In order to find sequences capable of maintaining the transcriptional activity of the CMV promoter sequence, genomic DNA sequences (gDNA) of promoter regions of housekeeping genes were analyzed, identifying a region with 67.7% of CG content corresponding to the promoter region and part of the first exon of beta-actin gene (ACTB) of the *Cricetulus griseus* (RegCG) (SEQ ID NO: 5). Briefly, the promoter sequence from gDNA of cells Chinese hamster ovary (CHO) was amplified by PCR using the F1 (SEQ ID NO: 27) and R1 primers (SEQ ID NO: 28) containing restriction sites for cloning. Then, this amplicon was purified and cloned into pGEM®-T Easy (Promega). Positive clones which were sequenced were selected, checking the construction designed. This fragment was subcloned into the expression vector Seq1-Luc (SEQ ID NO: 2), to generate Seq2-Luc (SEQ ID NO: 4). Stable cell lines were generated by transfection of CHO-K1 (ATCC CCL-61) cells with reporters vectors Seq1-Luc, Seq2-Luc, Seq3a-Luc, Seq3b-Luc and Seq3c-Luc (FIG. 1) and clones were isolated in the presence of the antibiotic G418 by limit dilution. Then, 16 clones were subcultured and luciferase activity was measured on day 41 after the removal of selection antibiotic. Luciferase activity of Seq2-Luc, Seq3a-Luc, Seq3b-Luc, and Seq3c-Luc is higher than the promoter activity Seq1-Luc at culture day 41 (FIG. 4).

Figure 9:
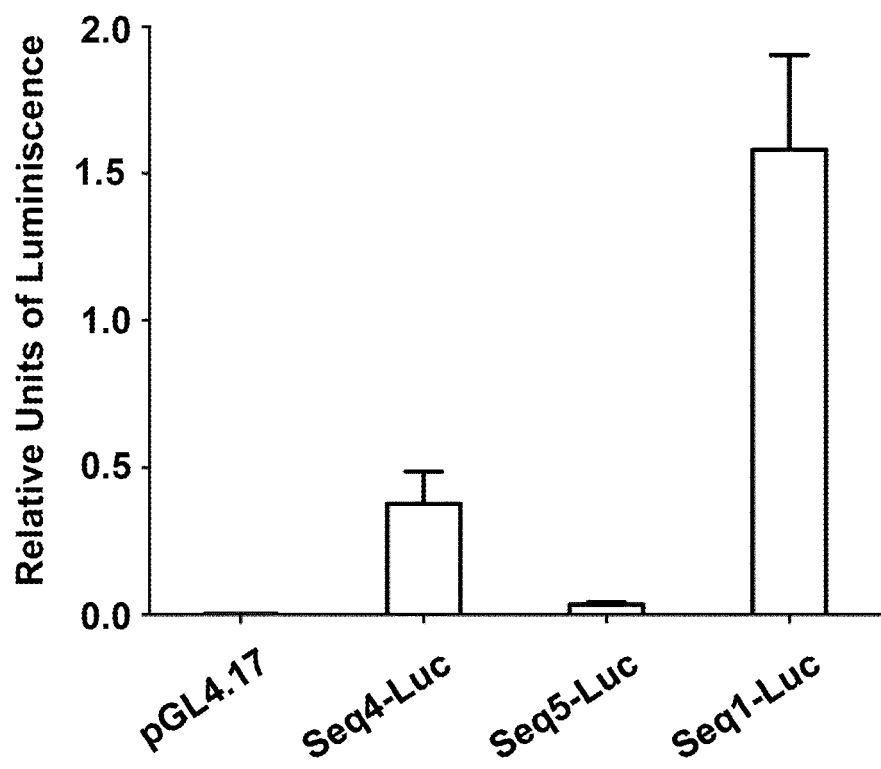
FIG. 9 shows luciferase activity expressed as relative luminescence units of different promoters in expression vectors Seq4-Luc (SEQ ID NO: 35), Seq5-Luc (SEQ ID NO: 36) and Seq1-Luc, transiently transfected in CHO K1 cells.

Furthermore, the effect of addition of the promoter on luciferase activity in transient transfections was determined. CHO-K1 cells were cultured to reach 90% confluence and were co-transfected using Lipofectamine CD (Invitrogen, USA), with the normalization vector pGL4.73 (Promega, USA) expressing *Renilla reniformis* luciferase (Ren), under the control of SV40 promoter, and with experimental vectors Seq1-Luc (SEQ ID NO: 2), Seq4-Luc (SEQ ID NO: 35) and Seq5-Luc (SEQ ID NO: 36) expressing *Photinus pyralis* luciferase (Luc), under the control of the promoters studied and pGL4.17 (base vector without promoter). Cotransfected cells were cultured for 18 hours at 37° C. and 5% $CO_2$, and then the luminescence product of the Luc and Ren reactions was independently analyzed using the "Dual-Glo Luciferase Assay System" (Promega system, USA) in white 96-well plates. Luminescence relative units were calculated by the ratio of Luc/Ren. It is noted that RegCG has transcriptional activity (FIG. 9).

Similarly, a DNA sequence (SEQ ID NO: 8) containing a tandem of 5 repeats of the consensus sequence elements glucocorticoid response (GRE) was synthesized, separated by 25 nucleotides of irrelevant sequence, i.e., which may be any sequence. Subsequently, GRE was incorporated into the vector carrying the CMV promoter with RegCG, between both elements, and Seq3a-Luc vector (SEQ ID NO: 7) was generated. Then, the luciferase activity of clones of CHO-K1 cells transfected with Seq2-Luc vectors and selected with G418 selection antibiotic was analyzed. It was compared with the activity of clones of cells transfected with the control vector Seq1-Luc (SEQ ID NO: 2), generated in the same way. To perform the analysis, clones were grown to a level of confluence of 50 to 80%, induced with dexamethasone at concentrations of 0; 0.1; 1 and 10 µM, respectively, and luciferase activity was measured after 48 hours of treatment. Regarding the promoter activity it was found, at day 41, that Seq2-Luc and Seq3a-Luc vectors presented 13 and 7.5 times, respectively, the activity of the control promoter (FIG. 4). Furthermore, Seq3a-Luc clones showed that there is a significant increase in luminescence of 30 to 40% compared to stimulation with dexamethasone (FIG. 5), where a Seq3c-Luc clone, whose promoter contains two tandem GRE, reached an increase of 70%.

Figure 6:
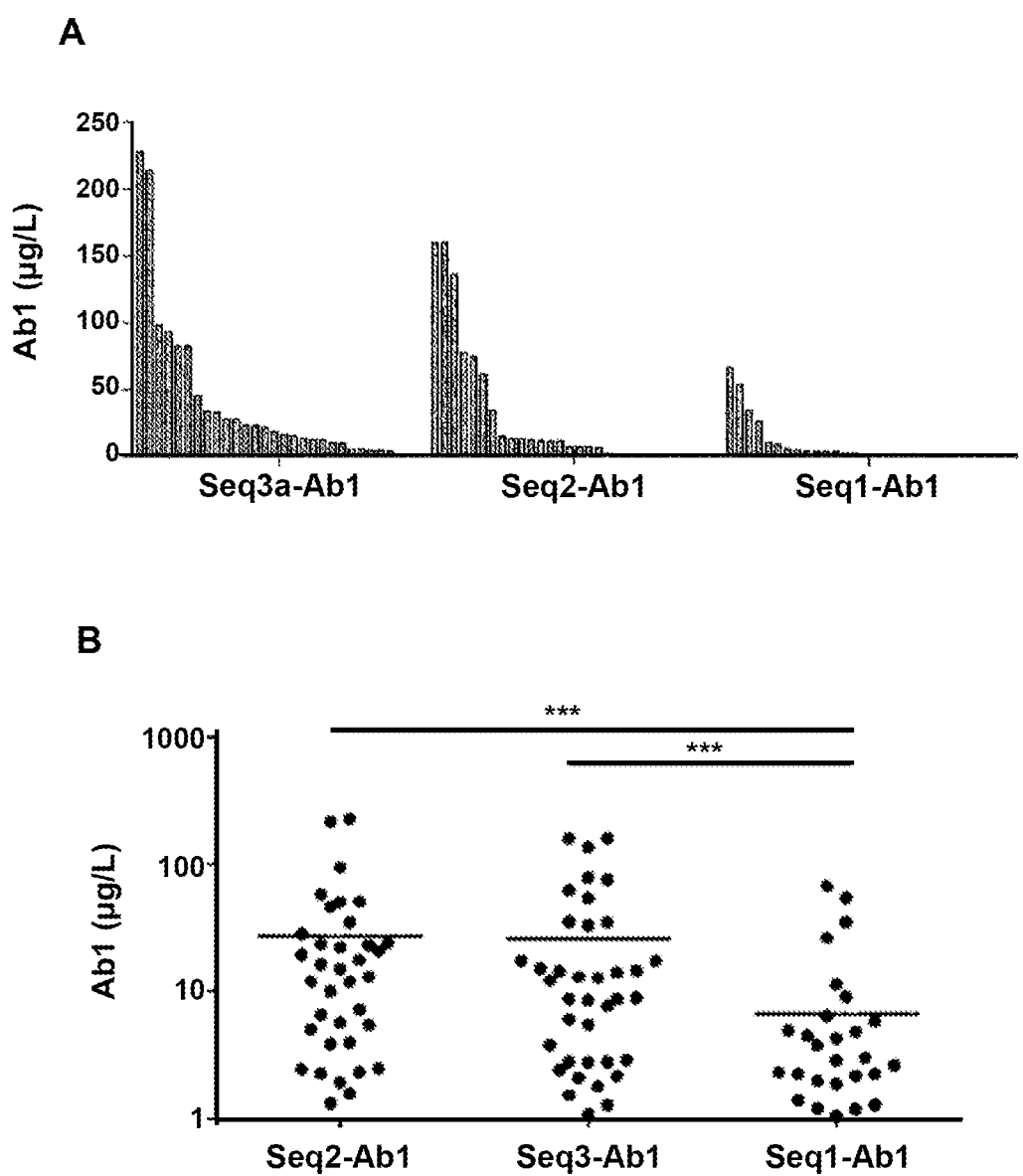
FIG. 6 shows Ab1 antibody production by clones containing the Seq1-Ab1, Seq2-Ab1 and Seq3a-Ab1 vectors (FIG. 2) in CHO-KI cells. Cells were transfected with Seq3a-Ab1, Seq2-Ab1 and Seq1-Ab1 vectors; and cloned by limit dilution, then subcultured for 15 days in the presence of the antibiotic G418 selection at 1 mg/mL. A) Distribution of clones based on their decreasing production level Ab1. B) Concentration of Ab1 produced by each clone according to the promoter. Mean values (horizontal bar) were Seq2-Ab1: 25.3 ug/L, Seq3a-Ab1: 24.3 ug/L and Seq1-Ab1: 6.2 ug/L. (***$P<0.001$).

Tests were performed to measure the expression of recombinant antibodies in stable transfections, for which several vectors were constructed. First, a bicistronic expression system was generated, where the luciferase gene was replaced by genes of the heavy (SEQ ID NO: 15) and light (SEQ ID NO: 16) chains of an anti-CD20 (Ab1) antibody, separated by a IRES (Internal Ribosomal Entry Site) (SEQ ID NO: 17) downstream of Seq1, Seq2 and Seq3a promoters. Stable expression clones were obtained by G418 selection and limit dilution, randomly selecting 39 clones of each construct. The passage supernatants were obtained corresponding to day 35 after removal of selection antibiotic and antibody production was measured by ELISA, which reached values higher than 300 g/L in 13 of them, being 4.1 times the average concentration of Seq2-Ab1 with respect to Seq1-Ab1 (FIG. 6).

Figure 7:
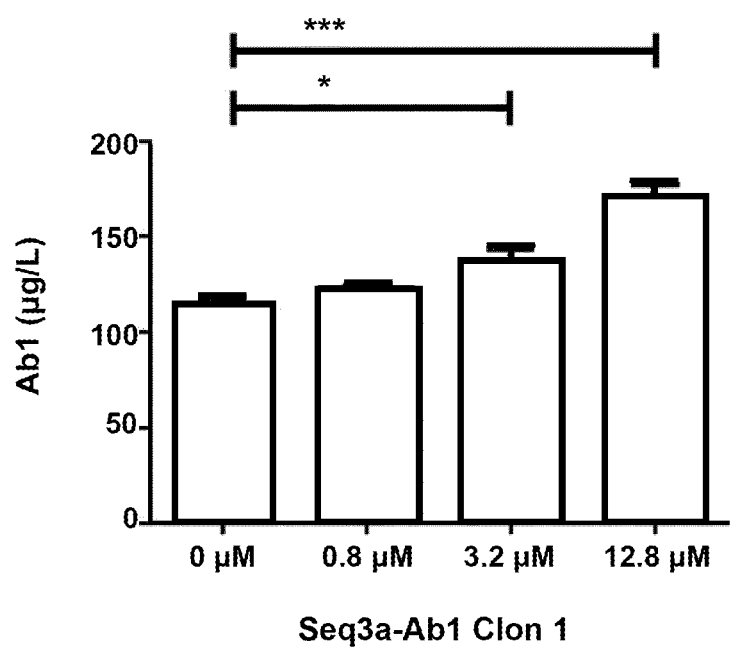
FIG. 7 shows the analysis of induction by dexamethasone of a stable clone with Seq3a-Ab1 promoter (SEQ ID NO: 21) having GRE. Ab1 concentration at different dexamethasone concentrations is shown. (*$P<0.05$; ***$P<0.001$).

Finally, clones generated using the construction Seq3a-Ab1 (SEQ ID NO: 21) having glucocorticoid response elements are able to respond to dexamethasone. Cells were grown to confluency and treated with dexamethasone at different concentrations (0, 0.8, 3.2 and 12.8 µM) and Ab1 concentration was measured after 48 hours by capture ELISA (FIG. 7).

Figure 3:
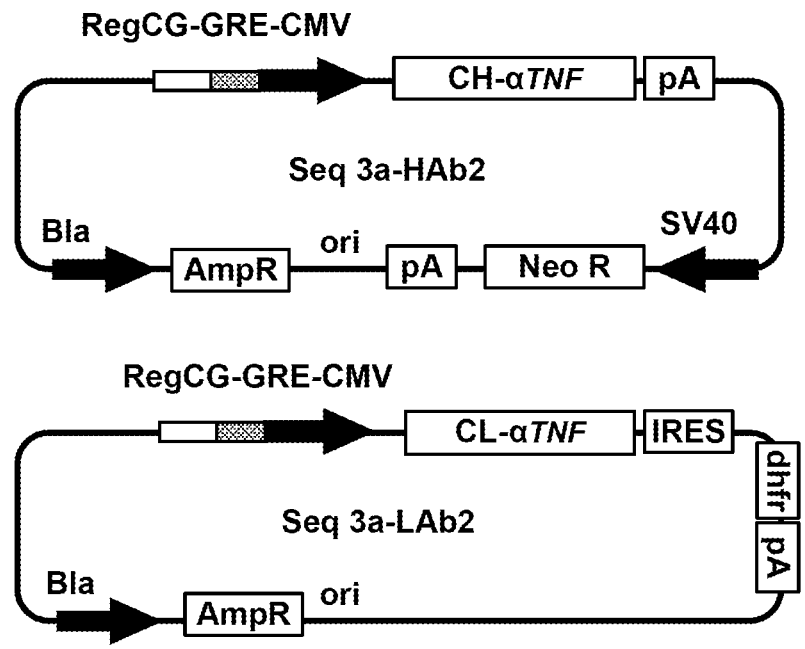
FIG. 3 shows a scheme of a variant RegCG-GRE-CMV promoter (SEQ ID NO: 9) in expression vectors encoding Ab2 antibody. Ab2 antibody is encoded by the genes of the heavy (SEQ ID NO: 22) and light (SEQ ID NO: 23) chains encoded in Seq3a-HAb2 (SEQ ID NO: 24) vector and Seq3a-LAb2 (SEQ ID NO: 25), respectively. The Seq3a-LAb2 vector contains downstream of the light chain and separated by a IRES (SEQ ID NO: 17) coding sequence for the enzyme dihydrofolate reductase (DHFR) (SEQ ID NO: 26).

The above results were developed in CHO-K1 cells, which are easy to clone and are grown in adhesion. The next step was to analyze the promoter activity in conditions of industrial application, mainly suspension growth, unlike the CHO-K1 cell line. The cell line CHO-DG44 (A1097101 Gibco by Life Technologies) is adapted to grow in suspension and has the mutated gene of the dihydrofolate reductase (DHFR) enzyme, so the expression vector of the recombinant protein contains the DHFR gene (SEQ ID NO: 26) which allows the growth of these cells when cultured in the absence of hypoxanthine and thymidine (HT). This deficiency is used to induce gene amplification of the recombinant genes which are co-expressed in the expression vector together with the DHFR gene when grown in the presence of methotrexate, an inhibitor of DHFR at sub toxic concentrations. Under these conditions, the cells respond by generating the DHFR gene amplifications, increasing the production of this enzyme, and increasing the dependent proliferation of the number of copies generated. Along with it, not only the DHFR gene is amplified, but also its surrounding regions. In this regard, the vector Seq3a-LAb2, a vector with the Seq3a promoter using IRES system to express the light chain gene of the Ab2 AcR downstream DHFR (FIG. 3) was constructed. For expression of heavy chain of the Ab2 AcR under the Seq3a promoter control, the Seq3a-HAb2 vector, subject to G418 selection antibiotic, was generated. Suspended CHODG-44 cells were transfected with both vectors and then the cells stably transformed with both vectors were selected on medium lacking HT and having G418. Thus, during the process of gene amplification, DHFR gene co-amplified the recombinant gene of the heavy chain (SEQ ID NO: 24) and light chain (SEQ ID NO: 25) of the Ab2 antibody. The generated cultures were grown in suspension in 6-well plates with 3 mL of CDOptiCHO® medium with 2 mM glutamine and 0.1% Pluronic® at 140 rpm for antibody production.

Figure 8:
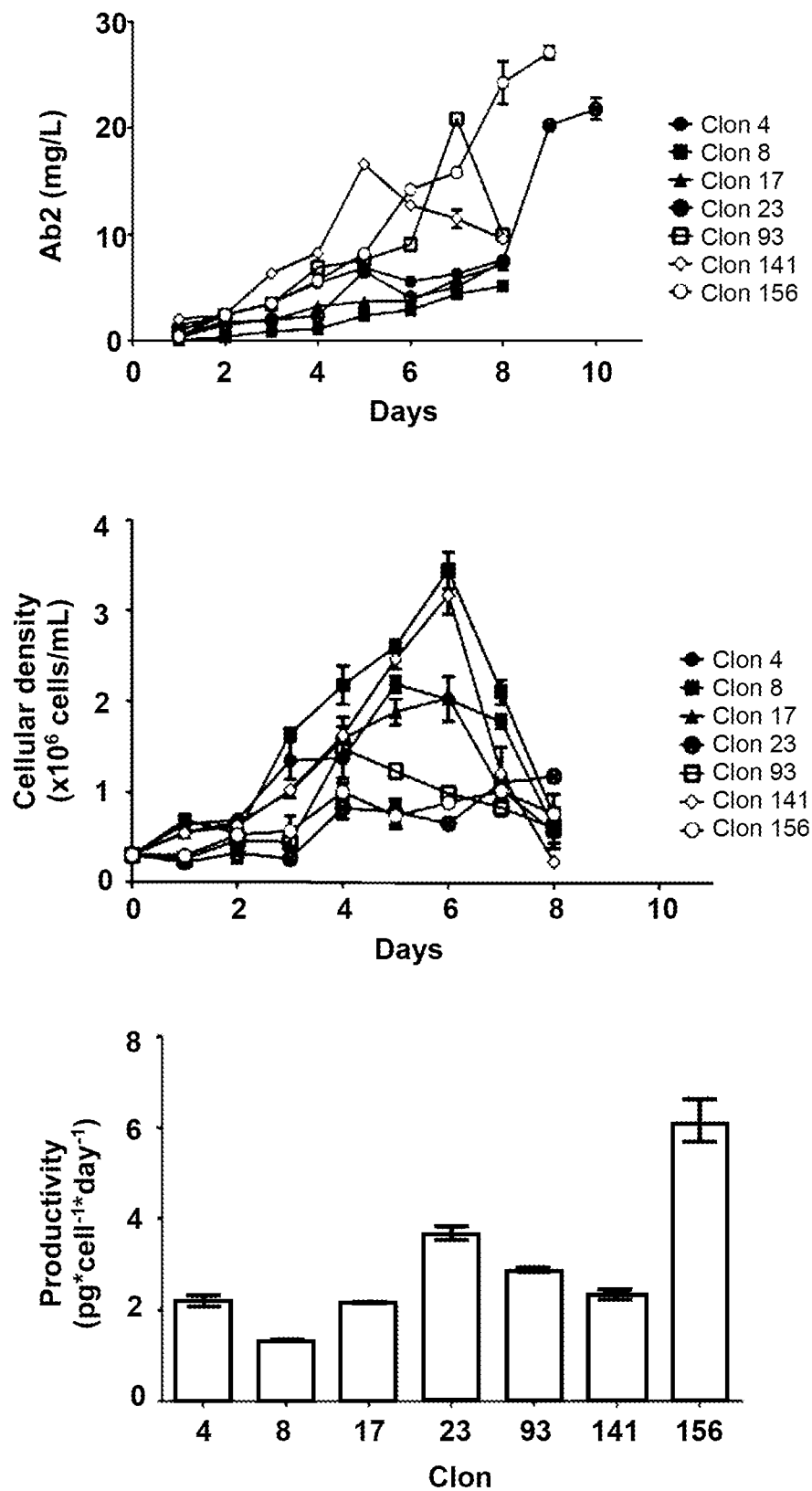
FIG. 8 shows the growth curves, production and productivity levels of specific Ab2 producing clones. Seven clones (4, 8, 17, 23, 93, 141 and 156) of CHO-DG44 cells co-transfected with vectors Seq3a-HAb2 (SEQ ID NO: 24) and Seq3a-LAb2 (SEQ ID NO: 25) selected for the production of Ab2 antibody.

As seen in FIG. 8, the Sec3a-HAb2 and Sec3a-LAb2 vectors containing RegCG are capable of producing the antibody in a form of suspension culture, and it was possible to isolate a large number of clones with this feature.

Example 1: Preparation of Expression Vectors of an Human Anti-TNF Under Control of the Promoter RegCG/GRE/CMV (SEQ ID NO:9)

The human anti-TNF antibody (or antibody Ab2) is produced by expression of the genes encoding for the light (LAb2) and heavy (HAb2) chains of Ab2, expressed in independent vectors, both under the control of the RegCG/GRE/CMV promoter. The Seq3a-HAb2 vector expresses HAb2 and contains a selection system based on the expression of the neomycin resistance gene under the control of the SV40 promoter. The Seq3a-LAb2 vector expresses LAb2 and contains a selection system based on the expression of the enzyme dihydrofolate reductase (DHFR), expressed in a biscistronic manner with LAb2. The RegCG/GRE/CMV promoter contained in both vectors was obtained from the Seq3a_Luc vector (FIG. 1).

For the construction of Seq3a-HAb2 vector (FIG. 3), the Luc2 gene was replaced from Seq3a-Luc vector with HAb2 gene. To do this, first, from the vector Seq3a-Luc, the fragment containing the Luc2 gene and poly A between restriction sites HindIII and BamHI was removed by digestion with the corresponding restriction enzymes. Between both sites, a DNA fragment synthesized by hybridizing oligonucleotides of complementary sequence IntF (SEQ ID NO: 37) and IntR (SEQ ID NO: 38) containing the restriction sites MluI, NdeI and EcoRI was inserted sequentially, leaving cohesive ends for restriction sites HindIII and BamHI, then, between the EcoRI and BamHI sites, a DNA fragment synthesized by PCR with primers PoA-Fw (SEQ ID NO: 39) and PoA-Rv (SEQ ID NO: 40) from the Seq3a-Luc vector was inserted, which contains the Poly A sequence, wherein the generated amplicon contains at its ends EcoRI and BamHI sites, generating Seq3a-IC vector (SEQ ID NO: 41), which has a polyclonal region downstream of the RegCG polyclonal/GRE/CMV promoter, where the gene of different recombinant proteins can be inserted. The fragment containing the HAb2 gene was obtained by PCR amplification with oligonucleotides HTNFHind-Fv (SEQ ID NO: 42) and RitHMlu-Rv (SEQ ID NO: 43), from the vector pHQG9 (SEQ ID NO: 44), where the amplicon leaves at its ends the cleavage sites for the restriction enzymes HindIII and MluI. The amplicon was cut with the enzymes HindIII and MluI (Fermentas) and then inserted into the Seq3a-IC vector (SEQ ID NO: 41) between the same sites by ligation with T4 ligase enzyme (NEB).

For the construction of the Seq3a-LAb2 vector (FIG. 3), first, the CMV promoter in the vector pKQG9 (SEQ ID NO: 45) was replaced with the RegCG/GRE/CMV promoter between the restriction sites SalI and HindIII. Then, the DNA fragment containing the RegCG/GRE/CMV promoter and the HAb2 gene between sites SalI and BamHI was cut. In parallel, the pOptiVEC-TOPO vector (Invitrogen) was cut by restriction between sites SalI and BamHI, and the DNA fragment containing the CMV promoter, located before the IRES sequence, was removed. Subsequently, the fragment containing the RegCG/GRE/CMV promoter and the LAb2 gene, between sites SalI and BamHI pKQG9 vector (SEQ ID NO: 45), was introduced, resulting in the bicistronic system, expressing LAb2 and DHFR on a single transcript where LAb2 and DHFR genes are separated by an IRES sequence.

Example 2: Host Cell Preparation for Expression of the Ab2 Antibody

The cells used correspond to the CHO cell line DG-44 (Gibco A1097101 by Life Technologies). To obtain clones derived from CHO DG44, the cells were co-transfected with Seq3a-LAb2 and Seq3a-HAb2 vectors by lipotransfection. Briefly, cells are routinely cultured in suspension and agitation with CD DG44 medium (Gibco), specific for CHO DG44 cells. They are seeded at a cell density of $3\times10^5$ cells/mL in 30 mL of culture, supplemented with 2 mM glutamine and 0.1% Pluronic (Sigma Aldrich) and cultured statically at 37° C. and 8% $CO_2$. Then, the reagent for transfection Lipofectamine 2000 (ThermoFisher Scientific) diluted in Opti-MEM (Gibco) was added and subsequently the DNA to be transfected was diluted into this mixture. The DNA was previously linearized by digestion with PvuI restriction enzyme, which cuts at a restriction site the ampicillin resistance element. The DNA/lipofectamine complex was added to the cells and 4 hours later the medium was changed by CD OptiCHO (ThermoFisher Scientific) with G418 800 g/mL, supplemented with 2 mM glutamine and Pluronic 0.1% (Sigma Aldrich), and culturing was continued at 37° C. and 5% $CO_2$, with stirring at 120 rpm. The culture medium was changed every three days until viability reached 90% or more. Then, the cells were cultured in the same culture medium but with the addition of methotrexate (ThermoFisher Scientific) at 50 nM with medium change every three days until viability reached 90% or more. This process was repeated for methotrexate concentrations of 100 nM, 250 nM and 500 nM. From the latter population, clones were obtained by single cell suspension in semisolid medium CloneCell (StemCell Technologies). The appearance of clones was confirmed two weeks after seeding and the clones obtained were transferred to 96-well culture plates in CD OptiCHO medium with G418, supplemented with 2 mM glutamine and 0.1% Pluronic (Sigma Aldrich), at 37° C. and 5% $CO_2$; for scaling.

Example 3: Effect of RegCG in Combination with GRE on the Transcriptional Activity of the CMV Promoter in Stable Cell Lines Stable cell lines were generated by transfecting CHO-K1 (ATCC CCL-61) cells with reporter vectors Seq1-Luc (SEQ ID NO: 2), Seq2-Luc (SEQ ID NO: 4), Seq3a-Luc (SEQ ID NO: 7), Seq3b-Luc (SEQ ID NO: 10), and Seq3c-Luc (SEQ ID NO: 12), for this the cells were cultured in 6-well plates using DMEM-F12 medium supplemented with 10% FBS until reaching 90% confluence. Cells were washed with phosphate buffered saline (PBS) and a mixture containing 1 μg of vector DNA is added, previously linearized by cutting with the restriction enzyme PvuI and purified with 20 μl of Lipofectamine 2000 (Invitrogen) in 500 μL of OptiMEM medium (Invitrogen). Cells with this mixture were incubated for 4 hours at 37° C. with 5% $CO_2$, after which the medium was removed and further incubated with 2 mL of DMEM-F12 medium supplemented with 10% FBS in the presence of selection antibiotic G418 (Gibco) at 500 g/mL. Once control transfection without vectors began to die, between 10 to 15 days, clones were isolated by limit dilution. For this purpose, the cells were released with trypsin and resuspended in DMEM-F12 supplemented with FBS and G418 at 800 g/mL, to which the cells were seeded in 96-well culture plates with 200 μl of cells at dilutions such as that 0.5; 1 and 10 cells per well plate remain on average. Cell growth was obtained in less than one third of the wells seeded at 0.5 cells per well, indicating that the cultures are clonal. Then, 16 random clones were selected for vector, which were subcultured in the absence of selection antibiotic to promote gene silencing, making passages every 3 to 4 days. Finally, the luciferase activity was measured on day 41 after the removal of selection antibiotic. For this, the "Bright-Glo™ Luciferase Assay System" (Promega) was used following the suppliers instructions, for which the culture cells of each clone were lysed, from which luciferase activity was measured by measuring luminescence generated by the addition of substrate of this enzyme and quantified in a model luminometer Luminoskan Ascent (Thermo Electronic Corporation). In parallel, from each lysate, the total concentration of proteins was quantified by the Bradford technique, whose reaction was quantified by the mediation of absorbance at 405 nm. This absorbance was used to normalize the luciferase activity by the ratio between luminescence (Luc) and the absorbance at 405 nm, (Luc/Abs), expressed as relative luminescence units. The data of the relative luminescence units were plotted on a dot plot in the statistical program GraphPad Prism (FIG. 4), in which the average values are indicated by a horizontal bar. Seq4-Luc vector, whose promoter is RegCG, has 3 times higher average activity than CMV, indicating that RegCG has greater resistance to silencing than CMV in clones already stabilized. Luciferase activity in vectors Seq2-Luc, Seq3a-Luc, Seq3b-Luc, Seq3c-Luc, whose promoters combine RegCG and CMV, have the highest activities, where the highest average activity was obtained with the Seq2-Luc vector containing the RegCG/CMV promoter, this being 13 times the average activity of the Seq1-Luc vector under the control of CMV. This shows that there is a potentiating effect of promoter activity by combining RegCG and CMV, regardless of the presence of GRE.

Example 4: Analysis of Dexamethasone Induction of Stable Clones with Promoters Having GRE (SEQ ID NOs: 9, 11 and 13)

Clones with increased production were selected from transfections with promoters containing GRE to test whether they are able to respond to dexamethasone by increasing reporter activity. To do this, the selected clones were cultured in 24-well plates in DMEM-F12 medium, supplemented with 10% FBS, seeding 500,000 cells/mL at 37° C. and $CO_2$ and 5%. The next day, they were stimulated by addition of dexamethasone (SIGMA) at different concentrations and cultivation was continued for 48 hours. The luciferase activity was then determined by Luc/Abs ration, similarly to that performed in Example 3.

Figure 5:
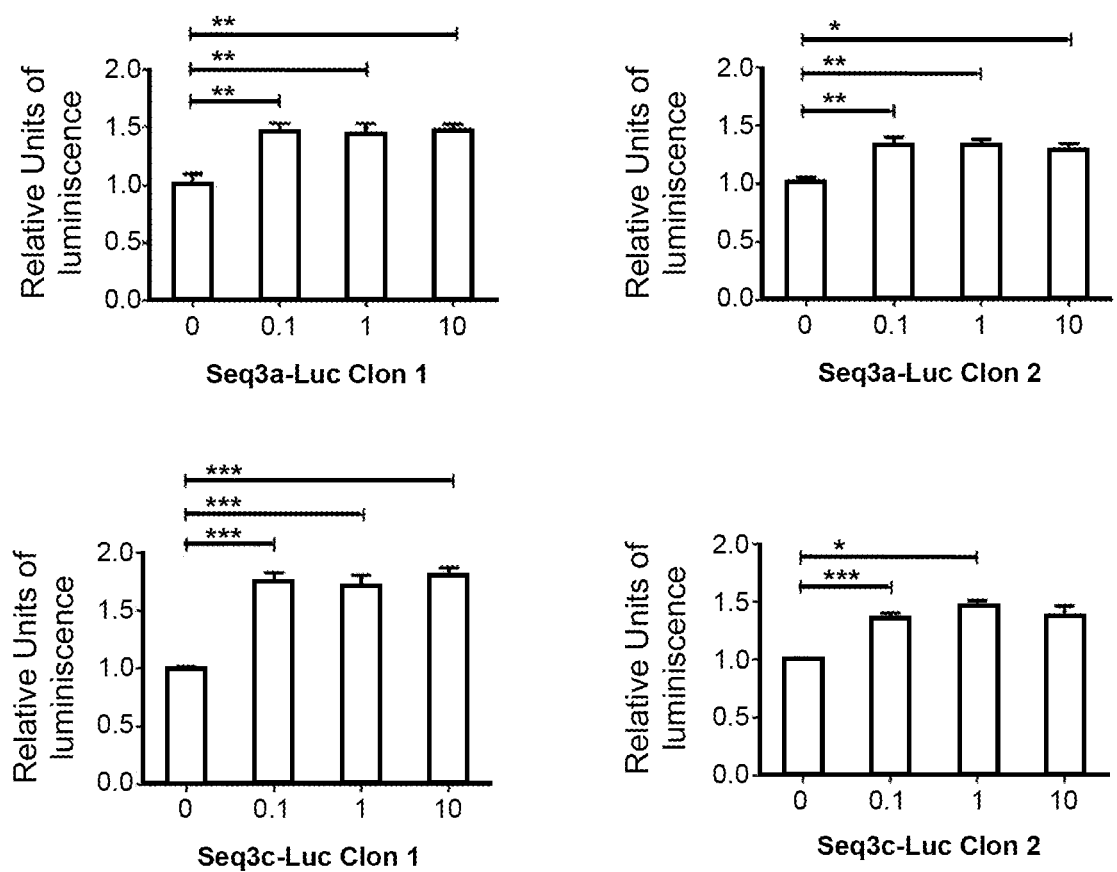
FIG. 5 shows the analysis of induction by dexamethasone of stable clones with promoters having GRE. It shows luciferase activity (RLU) of clones with GRE-containing promoters and RegCG with the CMV promoter. Relative Luminescence Units corresponds to the ratio between luciferase activity and protein concentration in the lysate, normalized with respect to the value obtained without dexamethasone (*$P<0.05$, $P<0.01$; *$P<0.001$).

In FIG. 5, the result of two Seq3a-Luc and two Seq3c-Luc clones is shown, which showed in average a significant increase of luminescence between 20% and 40%, compared to stimulation with dexamethasone between 0.1 and 10 µM.

Example 5: Production of Ab1 Antibody by Clones Containing the Seq1-Ab1 (SEQ ID NO: 19) Vector, Seq2-Ab1 (SEQ ID NO: 20), and Seq3a-Ab1 (SEQ ID NO: 21) in CHO-K1 Cells Stable cell lines were generated by transfecting CHO-K1 (ATCC CCL-61) cells with reporter vectors Seq1-Ab1, Seq2-Ab1, and Seq3a-Ab1, for this purpose the cells were cultured in 6-well plates in DMEM-F12 medium, supplemented with 10% FBS until reaching 90% confluence. Cells were washed with phosphate buffered saline (PBS) and a mixture containing 1 ug of vector DNA, previously linearized by cutting with the restriction enzyme PvuI and purified, along with 100 µl of Lipofectamine 2000 (Invitrogen) in 500 µl OptiMEM medium (Invitrogen). Cells with this mixture were incubated for 4 hours at 37° C. with 5% $CO_2$, after the which the medium was removed and further incubated with 2 mL of DMEM-F12 medium, supplemented with 10% FBS in the presence selection antibiotic G418 (Gibco) at 800 g/mL. Once control transfection without vector began to die, between 10 to 15 days, clones were isolated by limit dilution. For this purpose, the cells were released with trypsin and resuspended in DMEM-F12 medium, supplemented with FBS and G418 at 800 g/mL, to which the cells were seeded in 96-well culture plates with 200 µl of cells at dilutions such as that 0.5; 1 and 10 cells per well plate remain on average. Cell growth was obtained in less than one third of the wells seeded at 0.5 cells per well, indicating that the cultures are clonal. Then for each vector clones, 30 clones were randomly selected, which were subcultured in the absence of the selection antibiotic to promote gene silencing, making passages every 3 to 4 days. Finally, the production of secreted antibodies to the supernatant on day 39 was measured, after elimination of antibiotic selection. For this purpose, an ELISA capture was used, in which ELISA plates were sensitized with a human anti-IgG Kappa polyclonal antibody (Dako), then dilutions of culture supernatant were added to capture the Ab1 antibody. Then, a human anti-IgG antibody conjugated to HRP (IgG-HRP, eBioscience) was added, which was revealed with the reagent TMB (Thermo Fisher Scientific). Antibody concentration was determined by measuring absorbance at 405 nm and its calibration versus absorbance of wells with a commercial anti-CD20 (Rituximab) antibody instead of supernatant.

FIG. 6 shows in the upper panel the Seq1-Ab1, Seq2-Ab1 and Seq3a-Ab1 clones sorted from highest to lowest antibody production. In the bottom panel the same clones are shown in a dot plot, in which the mean values for each group of clones are indicated by a horizontal bar.

The average concentrations achieved with Seq2-Ab1 and Seq3a-Ab1 clones, whose promoters combine RegCG and CMV, are 4.5 times the average activity of vector Seq1-Ab1, under the control of CMV. This indicate a that there is a potentiating effect of promoter activity by combining RegCG and CMV, regardless of the presence of GRE. This supports what is shown in Example 4, in that RegCG has greater resistance to silencing than CMV in clones already stabilized.

Example 6: Analysis of Induction by Dexamethasone of a Stable Clone with Seq3a-Ab1 Promoter (SEQ ID NO: 21) Having GRE A high production clone was selected from transfections with Seq3a-Ab1 vector whose promoter contains GRE, to analyze whether it is able to respond to dexamethasone increasing production of antibody. For this, it was cultured in a 24-well plate in DMEM-F12 medium, supplemented with 10% FBS, seeding 500,000 cells/mL at 37° C. and 5% $CO_2$. Two days after the cells reached confluency, they were stimulated by addition of dexamethasone (SIGMA) at different concentrations and cultivation was continued for 48 hours. Then, The concentration of antibody secreted into the supernatant was determined using an ELISA capture with human anti-IgG Kappa polyclonal antibody (Dako) and revealed with an anti-IgG (eBioscience) antibody, similarly to that conducted in Example 5.

FIG. 7, shows the production result, showing a significant increase in the production of Ab1 compared to stimulation with dexamethasone at 3.2 and 12.8 µM, increasing by 48% the highest dose used with respect to the control without dexamethasone.

Example 7: Growth, Production and Productivity Levels of Specific Ab2 Producing Clones The clone was prepared according to Example 2, derived from CHO DG44 cells (A1097101 Gibco by Life Technologies) routinely maintained in culture medium CD OptiCHO (ThermoFisher Scientific) supplemented with 2 mM glutamine, 0.1% Pluronic (Sigma Aldrich) and G418 at 50 g/mL, at 37° C. and 5% $CO_2$. As a result of cloning, few initial cells are obtained, so the clones were initially grown in 96-well plates, to then be scaled as needed to 24-well plates and eventually to 6-well plates. After reaching the growth to seed in 6-well plates, cells were cultured with stirring at 120 rpm. To obtain the production and growth curves, the clones were seeded in Erlenmeyer flasks with ventilation filter, polycarbonate (Corning) at $3 \times 10^5$ cells/mL in 30 mL of culture medium. Every day an aliquot culture was removed for cell count and to obtain supernatant for determination of antibody concentration. Cell viability was determined by counting the cells stained with trypan blue on the microscope. The antibody concentration in supernatant was determined by ELISA capture. This assay consists of capturing the antibody in an ELISA plate previously sensitized with an anti-Kappa polyclonal antibody (Dako), followed by the addition of an antibody directed against the immunoglobulin heavy chain conjugated to peroxidase. Detection was performed using 3,3',5,5'-Tetramethylbenzidine (TMB, ThermoFisher Scientific) and the absorbance was measured at 450 nm. Specific productivity was calculated by the following formula:

$$qmAb = \frac{mmAb}{A}; A = \frac{(N - NO) \times t}{\ln\frac{N}{No}}$$

where mmAb represents the total mass of antibody in the supernatant in picograms; and N and NO the number of viable cells in times t2 and t1, respectively.

Clones were selected sequentially by their levels of antibody production from cultures in 96-well plates. Clones with the highest values were then cultured in 6-well plates, where the best 7 clones were selected, which were finally cultured in flasks containing 30 mL of medium and stirring characterizing their parameters of: variation of cell density over time, net production, and specific productivity of Ab2. FIG. 8 shows the analysis of the 7 clones selected, which shows that the higher production and specific productivities were achieved by clones 23 and 156.

Example 8: Luciferase Activity of Different Promoters in Expression Vectors Seq4-Luc (SEQ ID NO: 35), Seq5-Luc (SEQ ID NO: 36) and Seq1-Luc, Transiently Transfected in Cho K1 Cells CHO-K1 cells were cultured in 24-well plates in DMEM-F12 medium (Gibco) supplemented with 10% fetal bovine serum (FBS) (HyClone), at 37° C. and 5% $CO_2$, inoculating 300,000 cells/mL for 24 hours, or until reaching between 80 to 90% confluency. Then, cells were co-transfected independently with 500 ng of reporter vectors Seq4-Luc (SEQ ID NO: 35), Seq5-Luc (SEQ ID NO: 36), Seq1-Luc and empty vector pGL4.17 (Promega) together with 500 ng of normalizer vector pGL4.73 (Promega). To do this, for each transfection, the culture medium was removed and a mixture containing the reporter vector and the normalizer with 20 µl CD Lifectamine 2000 (Invitrogen) in 100 µl OptiMEM medium (Invitrogen) was added, and incubated for 4 hours at 37° C. and 5% $CO_2$. Then, the transfection mixture was removed and fed with 500 µl of DMEM-F12 medium, supplemented with 10% FBS and incubated for 48 hours at 37° C. and 5% $CO_2$. To analyze the activity of the reporter gene of the transfections, the "Dual-Glo Luciferase Assay System" (Promega, USA) was used following the manufacturers instruction, where from cell lysate the luciferase activity of firefly, expressed as reporter vectors and activity of *renilla* luciferase expressed by the normalizer vector, can be sequentially measured. Both activities were mediated by quantifying luminescence read on a Luminometer, model Luminoskan ASECNT (Thermo Electronic Corporation). The final measure was obtained from the ratio between the luminescence of the firefly (LUC) and *renilla* (Ren) luciferase, (Lun/Ren).

In FIG. 9, it was observed that the higher activity was obtained with the Seq2-Luc vector, under the control of CMV, the lowest activity was obtained with Seq5-Luc vector, under the control of the minimal portion of CMV or Core CMV. The Seq4-Luc vector, whose promoter is RegCG, is intermediate between the activity of Seq2-Luc and Seq5-Luc, indicating that the RegCG promoter of the Seq4-Luc vector is functional, reaching 24% of CMV activity.

An ASCII plain text file is accompanied by incorporation by reference herewith.

The invention claimed is:

1. A promoter for the expression of recombinant proteins (RP), comprising:
   a first promoter comprising the sequence of SEQ ID NO: 5 or a variant having the same function and more than 90% sequence identity;
   a second promoter comprising a cytomegalovirus (CMV) promoter comprising the sequence of SEQ ID NO: 3 or a variant having more than 90% sequence identity, located downstream of the first promoter, Wherein said second promoter has an enhancer comprising the sequence of SEQ ID NO: 29 and a core comprising the sequence of SEQ ID NO: 30; and
   a sequence comprising five (5) tandem glucocorticoid-responsive elements (GRE), said sequence comprising the sequence of SEQ ID NO: 8, located between said first and second promoters.

2. The promoter of claim 1, further comprising an additional sequence comprising five (5) tandem glucocorticoid-responsive elements (GRE), said sequence comprising the sequence of SEQ ID NO: 8, located between the enhancer and the core of the second promoter.

3. A vector comprising a promoter for the expression of recombinant proteins (RP), comprising:
   a first promoter comprising the sequence of SEQ ID NO: 5 or a variant having the same function and more than 90% sequence identity;
   a second promoter comprising a cytomegalovirus (CMV) promoter comprising the sequence of SEQ ID NO: 3 or a variant having more than 90% sequence identity, wherein said second promoter has an enhancer comprising the sequence of SEQ ID NO: 29 and a core comprising the sequence of SEQ ID NO: 30, located downstream of the first promoter; and
   a sequence comprising five (5) tandem glucocorticoid-responsive elements (GRE), said sequence comprising the sequence of SEQ ID NO: 8 located between said first and second promoters.

4. The vector of claim 3, wherein the vector comprises a sequence encoding a protein selected from the group consisting of an antibody and a chain of antibody.

5. The vector of claim 3, wherein the vector encodes an antibody heavy chain (Ab2) comprising the sequence of SEQ ID NO: 22 and an antibody light chain (Ab2) comprising the sequence of SEQ ID NO: 23.

6. The vector of claim 3, wherein the vector encodes an antibody heavy chain (Ab1) comprising the sequence of SEQ ID NO: 15 and an antibody light chain (Ab1) comprising the sequence of SEQ ID NO: 16.

7. The vector of claim 6, further comprising an IRES sequence comprising the sequence of SEQ ID NO: 17, located between the antibody heavy chain (Ab1) sequence and the antibody light chain (Ab1) sequence.

8. The vector of claim 3, wherein the vector comprises a sequence encoding dihydrofolate reductase (DHFR) comprising the sequence of SEQ ID NO: 26.

9. The vector of claim 8, wherein the vector responds in a dose-dependent manner when dexamethasone is present.

10. The vector of claim 3, wherein the promoter further comprises an additional sequence comprising five (5) tandem glucocorticoid-responsive elements (GRE), said sequence comprising the sequence of SEQ ID NO: 8, located between the enhancer and the core of the second promoter.

11. The vector of claim 5, further comprising an IRES sequence comprising the sequence of SEQ ID NO: 17, located between the antibody heavy chain (Ab2) sequence and the antibody light hair (Ab2) sequence.

12. A host cell, comprising the vector of claim 8.

13. The host cell of claim 12, wherein the host cell is a mammalian cell.

14. The host cell of claim 13, wherein the host cell is a Chinese hamster ovary cell (CHO).

15. A host cell, comprising the vector of claim 7.

16. A host cell, comprising the vector of claim 8.

17. A method for producing recombinant proteins (RP) comprising culturing in suspension a host cell comprising the vector of claim 3, wherein said vector further includes a sequence encoding a recombinant protein of interest.

18. A method for producing recombinant proteins (RP), comprising culturing in suspension the host cell of claim 15.

19. A method for producing recombinant proteins (RP), comprising culturing in suspension the host cell of claim 16.

* * * * *

SEQUENCE LISTING

```
<160> NUMBER OF SEQ ID NOS: 45

<210> SEQ ID NO 1
<211> LENGTH: 5599
<212> TYPE: DNA
<213> ORGANISM: Artificial Sequence
<220> FEATURE:
<223> OTHER INFORMATION: pGL4.17 vector encoding for the luciferase
      protein (Luc2)

<400> SEQUENCE: 1
ggcctaactg gccggtacct gagctcgcta gcctcgagga tatcaagatc tggcctcggc      60
ggccaagctt ggcaatccgg tactgttggt aaagccacca tggaagatgc caaaaacatt     120
aagaagggcc cagcgccatt ctacccactc gaagacggga ccgccggcga gcagctgcac     180
aaagccatga agcgctacgc cctggtgccc ggcaccatcg cctttaccga cgcacatatc     240
gaggtggaca ttacctacgc cgagtacttc gagatgagcg ttcggctggc agaagctatg     300
aagcgctatg ggctgaatac aaaccatcgg atcgtggtgt gcagcgagaa tagcttgcag     360
ttcttcatgc ccgtgttggg tgccctgttc atcggtgtgg ctgtggcccc agctaacgac     420
atctacaacg agcgcgagct gctgaacagc atgggcatca gccagcccac cgtcgtattc     480
gtgagcaaga aagggctgca aaagatcctc aacgtgcaaa agaagctacc gatcatacaa     540
aagatcatca tcatggatag caagaccgac taccagggct tccaaagcat gtacaccttc     600
gtgacttccc atttgccacc cggcttcaac gagtacgact tcgtgcccga gagcttcgac     660
cgggacaaaa ccatcgccct gatcatgaac agtagtggca gtaccggatt gcccaagggc     720
gtagccctac cgcaccgcac cgcttgtgtc cgattcagtc atgcccgcga ccccatcttc     780
ggcaaccaga tcatccccga caccgctatc ctcagcgtgg tgccatttca ccacggcttc     840
ggcatgttca ccacgctggg ctacttgatc tgcggctttc gggtcgtgct catgtaccgc     900
ttcgaggagg agctattctt gcgcagcttg caagactata agattcaatc tgccctgctg     960
gtgcccacac tatttagctt cttcgctaag agcactctca tcgacaagta cgacctaagc    1020
aacttgcacg agatcgccag cggcggggcg ccgtcagca aggaggtagg tgaggccgtg    1080
gccaaacgct tccacctacc aggcatccgc cagggctacg gcctgacaga aacaaccagc    1140
```

-continued

```
gccattctga tcaccccga agggacgac aagcctggcg cagtaggcaa ggtggtgccc      1200
ttcttcgagg ctaaggtggt ggacttggac accggtaaga cactgggtgt gaaccagcgc      1260
ggcgagctgt gcgtccgtgg ccccatgatc atgagcggct acgttaacaa ccccgaggct      1320
acaaacgctc tcatcgacaa ggacggctgg ctgcacagcg cgacatcgc ctactgggac      1380 gaggacgagc acttcttcat cgtggaccgg ctgaagagcc tgatcaaata caagggctac      1440
caggtagccc cagccgaact ggagagcatc ctgctgcaac accccaacat cttcgacgcc      1500
ggggtcgccg gcctgcccga cgacgatgcc ggcgagctgc ccgccgcagt cgtcgtgctg      1560
gaacacggta aaaccatgac cgagaaggag atcgtggact atgtggccag ccaggttaca      1620
accgccaaga agctgcgcgg tggtgttgtg ttcgtggacg aggtgcctaa aggactgacc      1680
ggcaagttgg acgcccgcaa gatccgcgag attctcatta aggccaagaa gggcggcaag      1740
atcgccgtgt aataattcta gagtcggggc ggccggccgc ttcgagcaga catgataaga      1800
tacattgatg agtttggaca aaccacaact agaatgcagt gaaaaaaatg ctttatttgt      1860
gaaatttgtg atgctattgc tttatttgta accattataa gctgcaataa acaagttaac      1920
aacaacaatt gcattcattt tatgtttcag gttcaggggg aggtgtggga ggttttttaa      1980
agcaagtaaa acctctacaa atgtggtaaa atcgataagg atccgtttgc gtattgggcg      2040
ctcttccgct gatctgcgca gcaccatggc ctgaaataac ctctgaaaga gaacttggt       2100 tagctacctt ctgaggcgga aagaaccagc tgtggaatgt gtgtcagtta gggtgtggaa      2160
agtccccagg ctccccagca ggcagaagta tgcaaagcat gcatctcaat tagtcagcaa      2220
ccaggtgtgg aaagtcccca ggctccccag caggcagaag tatgcaaagc atgcatctca      2280
attagtcagc aaccatagtc ccgcccctaa ctccgcccat cccgccccta actccgccca      2340
gttccgccca ttctccgccc catggctgac taatttttt tatttatgca gaggccgagg      2400
ccgcctctgc ctctgagcta ttccagaagt agtgaggagg ctttttgga ggcctaggct       2460 tttgcaaaaa gctcgattct tctgacacta gcgccaccat gatcgaacaa gacggcctcc      2520
atgctggcag tcccgcagct tgggtcgaac gcttgttcgg gtacgactgg gcccagcaga      2580
ccatcggatg tagcgatgcg gccgtgttcc gtctaagcgc tcaaggccgg cccgtgctgt      2640
tcgtgaagac cgacctgagc ggcgccctga acgagcttca agacgaggct gcccgcctga      2700
gctggctggc caccaccggc gtaccctgcg ccgctgtgtt ggatgttgtg accgaagccg      2760
gccgggactg gctgctgctg ggcgaggtcc ctggccagga tctgctgagc agccaccttg      2820
cccccgctga gaaggtttct atcatggccg atgcaatgcg cgcgcctgcac accctggacc      2880 ccgctacctg cccccttcgac caccaggcta agcatcggat cgagcgtgct cggacccgca      2940
tggaggccgg cctggtggac caggacgacc tggacgagga gcatcagggc ctggcccccg      3000
ctgaactgtt cgcccgactg aaagcccgca tgccggacgg tgaggacctg gttgtcacac      3060
acggagatgc ctgcctccct aacatcatgg tcgagaatgg ccgcttctcc ggcttcatcg      3120
actgcggtcg cctaggagtt gccgaccgct accaggacat cgccctggcc acccgcgaca      3180
tcgctgagga gcttggcggc gagtgggccg accgcttctt agtcttgtac ggcatcgcag      3240
ctcccgacag ccagcgcatc gccttctacc gcttgctcga cgagttcttt taatgatcta      3300
gaaccggtca tggccgcaat aaaatatctt tattttcatt acatctgtgt gttggttttt      3360
tgtgtgttcg aactagatgc tgtcgaccga tgcccttgag agccttcaac ccagtcagct      3420
ccttccggtg ggcgcgggc atgactatcg tcgccgcact tatgactgtc ttctttatca      3480
tgcaactcgt aggacaggtg ccggcagcgc tcttccgctt cctcgctcac tgactcgctg      3540
```

```
cgctcggtcg ttcggctgcg gcgagcggta tcagctcact caaaggcggt aatacggtta    3600
tccacagaat caggggataa cgcaggaaag aacatgtgag caaaaggcca gcaaaaggcc    3660
aggaaccgta aaaaggccgc gttgctggcg ttttttccata ggctccgccc ccctgacgag    3720
catcacaaaa atcgacgctc aagtcagagg tggcgaaacc cgacaggact ataaagatac    3780
caggcgtttc ccctggaag ctccctcgtg cgctctcctg ttccgaccct gccgcttacc    3840
ggatacctgt ccgcctttct cccttcggga agcgtggcgc tttctcatag ctcacgctgt    3900
aggtatctca gttcggtgta ggtcgttcgc tccaagctgg gctgtgtgca cgaaccccc    3960 gttcagcccg accgctgcgc cttatccggt aactatcgtc ttgagtccaa cccggtaaga    4020
cacgacttat cgccactggc agcagccact ggtaacagga ttagcagagc gaggtatgta    4080
ggcggtgcta cagagttctt gaagtggtgg cctaactacg gctacactag aagaacagta    4140
tttggtatct gcgctctgct gaagccagtt accttcggaa aaagagttgg tagctcttga    4200
tccggcaaac aaaccaccgc tggtagcggt ggttttttg tttgcaagca gcagattacg    4260
cgcagaaaaa aaggatctca agaagatcct ttgatctttt ctacggggtc tgacgctcag    4320
tggaacgaaa actcacgtta agggattttg gtcatgagat tatcaaaaag gatcttcacc    4380
tagatccttt taaattaaaa atgaagtttt aaatcaatct aaagtatata tgagtaaact    4440
tggtctgaca gcggccgcaa atgctaaacc actgcagtgg ttaccagtgc ttgatcagtg    4500
aggcaccgat ctcagcgatc tgcctatttc gttcgtccat agtggcctga ctccccgtcg    4560
tgtagatcac tacgattcgt gagggcttac catcaggccc cagcgcagca atgatgccgc    4620
gagagccgcg ttcaccggcc ccgatttgt cagcaatgaa ccagccagca gggagggccg    4680
agcgaagaag tggtcctgct actttgtccg cctccatcca gtctatgagc tgctgtcgtg    4740
atgctagagt aagaagttcg ccagtgagta gtttccgaag agttgtggcc attgctactg    4800
gcatcgtggt atcacgctcg tcgttcggta tggcttcgtt caactctggt tcccagcggt    4860
caagccgggt cacatgatca cccatattat gaagaaatgc agtcagctcc ttagggcctc    4920
cgatcgttgt cagaagtaag ttggccgcgg tgttgtcgct catggtaatg gcagcactac    4980
acaattctct taccgtcatg ccatccgtaa gatgcttttc cgtgaccggc gagtactcaa    5040
ccaagtcgtt ttgtgagtag tgtatacggc gaccaagctg ctcttgcccg gcgtctatac    5100
gggacaacac cgcgccacat agcagtactt tgaaagtgct catcatcggg aatcgttctt    5160
cggggcggaa agactcaagg atcttgccgc tattgagatc cagttcgata tagcccactc    5220
ttgcacccag ttgatcttca gcatctttta ctttcaccag cgtttcgggg tgtgcaaaaa    5280
caggcaagca aaatgccgca agaagggaa tgagtgcgac acgaaaatgt tggatgctca    5340
tactcgtcct ttttcaatat tattgaagca tttatcaggg ttactagtac gtctctcaag    5400
gataagtaag taatattaag gtacgggagg tattggacag gccgcaataa aatatcttta    5460
ttttcattac atctgtgtgt tggtttttg tgtgaatcga tagtactaac atacgctctc    5520
catcaaaaca aaacgaaaca aacaaacta gcaaataggg ctgtccccag tgcaagtgca    5580
ggtgccagaa catttctct                                                 5599
```

<210> SEQ ID NO 2
<211> LENGTH: 6214
<212> TYPE: DNA
<213> ORGANISM: Artificial Sequence
<220> FEATURE:
<223> OTHER INFORMATION: Seq1-Luc vector

```
<400> SEQUENCE: 2
ggcctaactg gccggtacct gagctcgcta gcctcgagga tatcaagatc tgttgacatt      60
gattattgac tagttattaa tagtaatcaa ttacgggtc attagttcat agcccatata      120
tggagttccg cgttacataa cttacggtaa atggcccgcc tggctgaccg cccaacgacc      180
cccgcccatt gacgtcaata atgacgtatg ttcccatagt aacgccaata gggactttcc      240
attgacgtca atgggtggag tatttacggt aaactgccca cttggcagta catcaagtgt      300
atcatatgcc aagtacgccc cctattgacg tcaatgacgg taaatggccc gcctggcatt      360
atgcccagta catgacctta tgggactttc ctacttggca gtacatctac gtattagtca      420
tcgctattac catggtgatg cggttttggc agtacatcaa tgggcgtgga tagcggtttg      480
actcacgggg atttccaagt ctccacccca ttgacgtcaa tgggagtttg ttttggcacc      540
aaaatcaacg ggactttcca aatgtcgta acaactccgc cccattgacg caaatgggcg      600
gtaggcgtgt acggtgggag gtctatataa gcagagctct ctggctaact agagaaccca      660
ctgcttactg gcttatcgaa agcttggcaa tccggtactg ttggtaaagc caccatggaa      720
gatgccaaaa acattaagaa gggcccagcg ccattctacc cactcgaaga cgggaccgcc      780
ggcgagcagc tgcacaaagc catgaagcgc tacgccctgg tgcccggcac catcgccttt      840
accgacgcac atatcgaggt ggacattacc tacgccgagt acttcgagat gagcgttcgg      900
ctggcagaag ctatgaagcg ctatgggctg aatacaaacc atcggatcgt ggtgtgcagc      960
gagaatagct tgcagttctt catgcccgtg ttgggtgccc tgttcatcgg tgtggctgtg     1020
gccccagcta cgacatcta caacgagcgc gagctgctga acagcatggg catcagccag     1080
cccaccgtcg tattcgtgag caagaaaggg ctgcaaaaga tcctcaacgt gcaaagaag     1140 ctaccgatca tacaaaagat catcatcatg gatagcaaga ccgactacca gggcttccaa     1200
agcatgtaca ccttcgtgac ttcccatttg ccacccggct tcaacgagta cgacttcgtg     1260
cccgagagct tcgaccggga caaaaccatc gccctgatca tgaacagtag tggcagtacc     1320
ggattgccca agggcgtagc cctaccgcac cgcaccgctt gtgtccgatt cagtcatgcc     1380
cgcgacccca tcttcggcaa ccagatcatc cccgacaccg ctatcctcag cgtggtgcca     1440
tttcaccacg gcttcggcat gttcaccacg ctgggctact tgatctgcgg ctttcgggtc     1500
gtgctcatgt accgcttcga ggaggagcta ttcttgcgca gcttgcaaga ctataagatt     1560
caatctgccc tgctggtgcc cacactattt agcttcttcg ctaagagcac tctcatcgac     1620
aagtacgacc taagcaactt gcacgagatc gccagcggcg gggcgccgct cagcaaggag     1680
gtaggtgagg ccgtggccaa acgcttccac ctaccaggca tccgccaggg ctacggcctg     1740
acagaaacaa ccagcgccat tctgatcacc cccgaagggg acgacaagcc tggcgcagta     1800
ggcaaggtgg tgcccttctt cgaggctaag gtggtggact ggacaccgg taagacactg     1860 ggtgtgaacc agcgcggcga gctgtgcgtc cgtggcccca tgatcatgag cggctacgtt     1920
aacaaccccg aggctacaaa cgctctcatc gacaaggacg gctggctgca cagcggcgac     1980
atcgcctact gggacgagga cgagcacttc ttcatcgtgg accggctgaa gagcctgatc     2040
aaatacaagg gctaccaggt agccccagcc gaactggaga gcatcctgct gcaacacccc     2100
aacatcttcg acgccgggt cgccggcctg cccgacgacg atgccggcga gctgcccgcc     2160
gcagtcgtcg tgctggaaca cggtaaaacc atgaccgaga aggagatcgt ggactatgtg     2220
gccagccagg ttacaaccgc caagaagctg cgcggtggtg ttgtgttcgt ggacgaggtg     2280
cctaaaggac tgaccggcaa gttggacgcc cgcaagatcc gcgagattct cattaaggcc     2340
```

```
aagaagggcg gcaagatcgc cgtgtaataa ttctagagtc ggggcggccg gccgcttcga    2400
gcagacatga taagatacat tgatgagttt ggacaaacca caactagaat gcagtgaaaa    2460
aaatgcttta tttgtgaaat ttgtgatgct attgctttat tgtaaccat tataagctgc     2520 aataaacaag ttaacaacaa caattgcatt cattttatgt ttcaggttca ggggaggtg    2580 tgggaggttt tttaaagcaa gtaaaacctc tacaaatgtg gtaaaatcga taaggatccg    2640
tttgcgtatt gggcgctctt ccgctgatct gcgcagcacc atggcctgaa ataacctctg    2700
aaagaggaac ttggttagct accttctgag gcggaaagaa ccagctgtgg aatgtgtgtc    2760
agttagggtg tggaaagtcc ccaggctccc cagcaggcag aagtatgcaa agcatgcatc    2820
tcaattagtc agcaaccagg tgtggaaagt ccccaggctc cccagcaggc agaagtatgc    2880
aaagcatgca tctcaattag tcagcaacca tagtcccgcc cctaactccg cccatcccgc    2940
ccctaactcc gcccagttcc gcccattctc cgccccatgg ctgactaatt ttttttattt    3000
atgcagaggc cgaggccgcc tctgcctctg agctattcca gaagtagtga ggaggctttt    3060
ttggaggcct aggcttttgc aaaaagctcg attcttctga cactagcgcc accatgatcg    3120
aacaagacgg cctccatgct ggcagtcccg cagcttgggt cgaacgcttg ttcgggtacg    3180
actgggccca gcagaccatc ggatgtagcg atgcggccgt gttccgtcta agcgctcaag    3240
gccggcccgt gctgttcgtg aagaccgacc tgagcggcgc cctgaacgag cttcaagacg    3300
aggctgcccg cctgagctgg ctggccacca ccggcgtacc ctgcgccgct gtgttggatg    3360
ttgtgaccga agccggccgg gactggctgc tgctgggcga ggtccctggc caggatctgc    3420
tgagcagcca ccttgccccc gctgagaagg tttctatcat ggccgatgca atgcggcgcc    3480
tgcacaccct ggaccccgct acctgcccct tcgaccacca ggctaagcat cggatcgagc    3540
gtgctcggac ccgcatggag gccggcctgg tggaccagga cgacctggac gaggagcatc    3600
agggcctggc ccccgctgaa ctgttcgccc gactgaaagc ccgcatgccg gacggtgagg    3660
acctggttgt cacacacgga gatgcctgcc tccctaacat catggtcgag aatggccgct    3720
tctccggctt catcgactgc ggtcgcctag gagttgccga ccgctaccag gacatcgccc    3780
tggccacccg cgacatcgct gaggagcttg gcggcgagtg ggccgaccgc ttcttagtct    3840
tgtacggcat cgcagctccc gacagccagc gcatcgcctt ctaccgcttg ctcgacgagt    3900
tcttttaatg atctagaacc ggtcatggcc gcaataaaat atctttattt tcattacatc    3960
tgtgtgttgg ttttttgtgt gttcgaacta gatgctgtcg accgatgccc ttgagagcct    4020
tcaacccagt cagctccttc cggtgggcgc ggggcatgac tatcgtcgcc gcacttatga    4080
ctgtcttctt tatcatgcaa ctcgtaggac aggtgccggc agcgctcttc cgcttcctcg    4140
ctcactgact cgctgcgctc ggtcgttcgg ctgcggcgag cggtatcagc tcactcaaag    4200
gcggtaatac ggttatccac agaatcaggg gataacgcag gaaagaacat gtgagcaaaa    4260
ggccagcaaa aggccaggaa ccgtaaaaag gccgcgttgc tggcgttttt ccataggctc    4320
cgcccccctg acgagcatca caaaaatcga cgctcaagtc agaggtggcg aaacccgaca    4380
ggactataaa gataccaggc gtttccccct ggaagctccc tcgtgcgctc tcctgttccg    4440
accctgccgc ttaccggata cctgtccgcc tttctccctt cggaagcgt ggcgctttct    4500 catagctcac gctgtaggta tctcagttcg gtgtaggtcg ttcgctccaa gctgggctgt    4560
gtgcacgaac cccccgttca gcccgaccgc tgcgccttat ccggtaacta tcgtcttgag    4620
tccaacccgg taagacacga cttatcgcca ctggcagcag ccactggtaa caggattagc    4680
```

```
agagcgaggt atgtaggcgg tgctacagag ttcttgaagt ggtggcctaa ctacggctac    4740
actagaagaa cagtatttgg tatctgcgct ctgctgaagc cagttacctt cggaaaaaga    4800
gttggtagct cttgatccgg caaacaaacc accgctggta gcggtggttt ttttgtttgc    4860
aagcagcaga ttacgcgcag aaaaaaagga tctcaagaag atcctttgat cttttctacg    4920
gggtctgacg ctcagtggaa cgaaaactca cgttaaggga ttttggtcat gagattatca    4980
aaaaggatct tcacctagat ccttttaaat taaaaatgaa gttttaaatc aatctaaagt    5040
atatatgagt aaacttggtc tgacagcggc cgcaaatgct aaaccactgc agtggttacc    5100
agtgcttgat cagtgaggca ccgatctcag cgatctgcct atttcgttcg tccatagtgg    5160
cctgactccc cgtcgtgtag atcactacga ttcgtgaggg cttaccatca ggccccagcg    5220
cagcaatgat gccgcgagag ccgcgttcac cggcccccga tttgtcagca atgaaccagc    5280
cagcagggag ggccgagcga agaagtggtc ctgctacttt gtccgcctcc atccagtcta    5340
tgagctgctg tcgtgatgct agagtaagaa gttcgccagt gagtagtttc gaagagttg    5400 tggccattgc tactggcatc gtggtatcac gctcgtcgtt cggtatggct tcgttcaact    5460
ctggttccca gcggtcaagc cgggtcacat gatcacccat attatgaaga aatgcagtca    5520
gctccttagg gcctccgatc gttgtcagaa gtaagttggc cgcggtgttg tcgctcatgg    5580
taatggcagc actacacaat tctcttaccg tcatgccatc cgtaagatgc ttttccgtga    5640
ccggcgagta ctcaaccaag tcgttttgtg agtagtgtat acggcgacca agctgctctt    5700
gcccggcgtc tatacgggac aacaccgcgc cacatagcag tactttgaaa gtgctcatca    5760
tcgggaatcg ttcttcgggg cggaaagact caaggatctt gccgctattg agatccagtt    5820
cgatatagcc cactcttgca cccagttgat cttcagcatc ttttactttc accagcgttt    5880
cggggtgtgc aaaaacaggc aagcaaaatg ccgcaaagaa gggaatgagt gcgacacgaa    5940
aatgttggat gctcatactc gtccttttc aatattattg aagcatttat cagggttact    6000
agtacgtctc tcaaggataa gtaagtaata ttaaggtacg ggaggtattg gacaggccgc    6060
aataaaatat ctttattttc attacatctg tgtgttggtt ttttgtgtga atcgatagta    6120
ctaacatacg ctctccatca aaacaaaacg aaacaaaaca aactagcaaa ataggctgtc    6180
cccagtgcaa gtgcaggtgc cagaacattt ctct                                6214
```

<210> SEQ ID NO 3
<211> LENGTH: 628
<212> TYPE: DNA
<213> ORGANISM: Artificial Sequence
<220> FEATURE:
<223> OTHER INFORMATION: Promoter region CMV

<400> SEQUENCE: 3

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
```

```
aaatgggcgg taggcgtgta cggtgggagg tctatataag cagagctctc tggctaacta      600
gagaacccac tgcttactgg cttatcga                                         628

<210> SEQ ID NO 4
<211> LENGTH: 7376
<212> TYPE: DNA
<213> ORGANISM: Artificial Sequence
<220> FEATURE:
<223> OTHER INFORMATION: Seq2-Luc vector

<400> SEQUENCE: 4
ggcctaactg gccggtaccg gagaggggt aaaaaaatgc tgcactgtgc ggctaggccg       60
gtgagtgagc ggcgcggagc caatcagcgc tcgccgttcc gaaagttgcc ttttatggct     120
cgagtggccg ctgtggcgtc ctataaaacc cggcggcgca acgcgcagcc actgtcgagt     180
ccgcgtccac ccgcgagcac aggccttcg cagctctttc ttcgccgctc cacacccgcc     240
accaggtaag cagggacaac aggcccagcc ggccacagcc ctcccgtggg cagtgaccgc     300 gctgcaggt cgcggggac actcggcgcg acaccgggg aaggctggag ggtggtgccg       360
ggccgcggag cggacacttt cagatccaac tttcagtcca gggtgtagac cctttacagc     420
cgcattgcca cggtgtagac accggtggac ccgctctggc tcagagcacg cggcttgggg     480
gaacccatta gggtcgcagt gtgggcgcta tgagagccga tgcagctttc gggtgttgaa     540
ccgtatctgc ccaccttggg gggaggacac aaggtcggga gccaaacgcc acgatcatgc     600
cttggtggcc catgggtctt tgtctaaacc ggtttgccca tttggcttgc cgggcgggcg     660
ggcgcggcgg gcccggctcg gccgggttgg gggctgggtt gccactgcgc ttgcgcgctc     720
tatggctggg tattgggcg cgtgcacgct ggggagggag ccttcctct tcccctctc       780 ccaagttaaa cttgcgcgtg cgtattgaga cttggagcgc ggccaccggg gttgggcgag     840
ggcggggccg ttgtccggaa ggggcggggt cgcagcggct tcgggcgcc tgctcgcgct     900 tcctgctggg tgtggtcgcc tcccgcgcgc gcactagccg cccgccggcg gggcgaaggc     960
ggggcttgcg cccgtttggg gaggggcgg aggcctggct tcctgccgtg gggccgcctc    1020
cggaccagcg tttgcctctt atggtaataa cgcggccggc ctgggcttcc tttgtcccct    1080
gagtttgggc gcgcgccccc tggcggcccg aggccgcggc ttgccggaag tgggcagggc    1140
ggcagcggct gcgcctagtg gcccgccagt gaccgcgacc ctcttttgtg ccctgatata    1200
gttcgccaga tctgttgaca ttgattattg actagttatt aatagtaatc aattacgggg    1260
tcattagttc atagcccata tatggagttc cgcgttacat aacttacggt aaatggcccg    1320
cctggctgac cgcccaacga cccccgccca ttgacgtcaa taatgacgta tgttcccata    1380
gtaacgccaa tagggacttt ccattgacgt caatgggtgg agtatttacg gtaaactgcc    1440
cacttggcag tacatcaagt gtatcatatg ccaagtacgc ccctattga cgtcaatgac    1500 ggtaaatggc ccgcctggca ttatgcccag tacatgacct tatgggactt tcctacttgg    1560
cagtacatct acgtattagt catcgctatt accatggtga tgcggttttg gcagtacatc    1620
aatgggcgtg atagcggtt tgactcacgg ggatttccaa gtctccaccc cattgacgtc    1680
aatgggagtt tgttttggca ccaaaatcaa cgggactttc caaaatgtcg taacaactcc    1740
gccccattga cgcaaatggg cggtaggcgt gtacggtggg aggtctatat aagcagagct    1800
ctctggctaa ctagagaacc cactgcttac tggcttatcg aaagcttggc aatccggtac    1860
tgttggtaaa gccaccatgg aagatgccaa aaacattaag aagggcccag cgccattcta    1920
```

```
cccactcgaa gacgggaccg ccggcgagca gctgcacaaa gccatgaagc gctacgccct      1980
ggtgcccggc accatcgcct ttaccgacgc acatatcgag gtggacatta cctacgccga      2040
gtacttcgag atgagcgttc ggctggcaga agctatgaag cgctatgggc tgaatacaaa      2100
ccatcggatc gtggtgtgca gcgagaatag cttgcagttc ttcatgcccg tgttgggtgc      2160
cctgttcatc ggtgtggctg tggccccagc taacgacatc tacaacgagc gcgagctgct      2220
gaacagcatg gcatcagcc agcccaccgt cgtattcgtg agcaagaaag gctgcaaaa       2280
gatcctcaac gtgcaaaaga agctaccgat catacaaaag atcatcatca tggatagcaa      2340
gaccgactac cagggcttcc aaagcatgta caccttcgtg acttcccatt gccacccgg       2400
cttcaacgag tacgacttcg tgcccgagag cttcgaccgg gacaaaacca tcgccctgat      2460
catgaacagt agtggcagta ccggattgcc caagggcgta gccctaccgc accgcaccgc      2520
ttgtgtccga ttcagtcatg cccgcgaccc catcttcggc aaccagatca tccccgacac      2580
cgctatcctc agcgtggtgc catttcacca cggcttcggc atgttcacca cgctgggcta      2640
cttgatctgc ggctttcggg tcgtgctcat gtaccgcttc gaggaggagc tattcttgcg      2700
cagcttgcaa gactataaga ttcaatctgc cctgctggtg cccacactat ttagcttctt      2760
cgctaagagc actctcatcg acaagtacga cctaagcaac ttgcacgaga tcgccagcgg      2820
cggggcgccg ctcagcaagg aggtaggtga ggccgtggcc aaacgcttcc acctaccagg      2880
catccgccag ggctacggcc tgacagaaac aaccagcgcc attctgatca ccccgaaagg      2940
ggacgacaag cctggcgcag taggcaaggt ggtgcccttc ttcgaggcta aggtggtgga      3000
cttggacacc ggtaagacac tgggtgtgaa ccagcgcggc gagctgtgcg tccgtggccc      3060
catgatcatg agcggctacg ttaacaaccc cgaggctaca aacgctctca tcgacaagga      3120
cggctggctg cacagcggcg acatcgccta ctgggacgag gacgagcact tcttcatcgt      3180
ggaccggctg aagagcctga tcaaatacaa gggctaccag gtagccccag ccgaactgga      3240
gagcatcctg ctgcaacacc ccaacatctt cgacgccggg gtcgccggcc tgcccgacga      3300
cgatgccggc gagctgcccg ccgcagtcgt cgtgctggaa cacggtaaaa ccatgaccga      3360
gaaggagatc gtggactatg tggccagcca ggttacaacc gccaagaagc tgcgcggtgg      3420
tgttgtgttc gtggacgagg tgcctaaagg actgaccggc aagttggacg cccgcaagat      3480
ccgcgagatt ctcattaagg ccaagaaggg cggcaagatc gccgtgtaat aattctagag      3540
tcggggcggc cggccgcttc gagcagacat gataagatac attgatgagt ttggacaaac      3600
cacaactaga atgcagtgaa aaaaatgctt tatttgtgaa atttgtgatg ctattgcttt      3660
atttgtaacc attataagct gcaataaaca agttaacaac aacaattgca ttcattttat      3720
gtttcaggtt cagggggagg tgtgggaggt tttttaaagc aagtaaaacc tctacaaatg      3780
tggtaaaatc gataaggatc cgtttgcgta ttgggcgctc ttccgctgat ctgcgcagca      3840
ccatggcctg aaataacctc tgaaagagga acttggttag ctaccttctg aggcggaaag      3900
aaccagctgt ggaatgtgtg tcagttaggg tgtggaaagt ccccaggctc cccagcaggc      3960
agaagtatgc aaagcatgca tctcaattag tcagcaacca ggtgtggaaa gtccccaggc      4020
tccccagcag gcagaagtat gcaaagcatg catctcaatt agtcagcaac catagtcccg      4080
cccctaactc cgcccatccc gcccctaact ccgcccagtt ccgcccattc tccgccccat      4140
ggctgactaa ttttttttat ttatgcagag gccgaggccg cctctgcctc tgagctattc      4200
cagaagtagt gaggaggctt ttttggaggc ctaggctttt gcaaaaagct cgattcttct      4260
gacactagcg ccaccatgat cgaacaagac ggcctccatg ctggcagtcc cgcagcttgg      4320
```

```
gtcgaacgct tgttcgggta cgactgggcc cagcagacca tcggatgtag cgatgcggcc    4380
gtgttccgtc taagcgctca aggccggccc gtgctgttcg tgaagaccga cctgagcggc    4440
gccctgaacg agcttcaaga cgaggctgcc cgcctgagct ggctggccac caccggcgta    4500
ccctgcgccg ctgtgttgga tgttgtgacc gaagccggcc gggactggct gctgctgggc    4560
gaggtccctg ccaggatct gctgagcagc caccttgccc ccgctgagaa ggtttctatc    4620
atggccgatg caatgcggcg cctgcacacc ctggaccccg ctacctgccc cttcgaccac    4680
caggctaagc atcggatcga gcgtgctcgg acccgcatgg aggccggcct ggtggaccag    4740
gacgacctgg acgaggagca tcagggcctg gcccccgctg aactgttcgc ccgactgaaa    4800
gcccgcatgc cggacggtga ggacctggtt gtcacacacg gagatgcctg cctccctaac    4860
atcatggtcg agaatggccg cttctccggc ttcatcgact gcggtcgcct aggagttgcc    4920
gaccgctacc aggacatcgc cctggccacc cgcgacatcg ctgaggagct ggcggcgag    4980 tgggccgacc gcttcttagt cttgtacgg atcgcagctc ccgacagcca gcgcatcgcc    5040
ttctaccgct tgctcgacga gttcttttaa tgatctagaa ccggtcatgg ccgcaataaa    5100
atatctttat tttcattaca tctgtgtgtt ggttttttgt gtgttcgaac tagatgctgt    5160
cgaccgatgc ccttgagagc cttcaaccca gtcagctcct tccggtgggc gcggggcatg    5220
actatcgtcg ccgcacttat gactgtcttc tttatcatgc aactcgtagg acaggtgccg    5280
gcagcgctct tccgcttcct cgctcactga ctcgctgcgc tcggtcgttc ggctgcggcg    5340
agcggtatca gctcactcaa aggcggtaat acggttatcc acagaatcag gggataacgc    5400
aggaaagaac atgtgagcaa aaggccagca aaaggccagg aaccgtaaaa aggccgcgtt    5460
gctggcgttt ttccataggc tccgcccccc tgacgagcat cacaaaaatc gacgctcaag    5520
tcagaggtgg cgaaacccga caggactata aagataccag gcgtttcccc ctggaagctc    5580
cctcgtgcgc tctcctgttc cgaccctgcc gcttaccgga tacctgtccg cctttctccc    5640
ttcgggaagc gtggcgcttt ctcatagctc acgctgtagg tatctcagtt cggtgtaggt    5700
cgttcgctcc aagctgggct gtgtgcacga accccccgtt cagcccgacc gctgcgcctt    5760
atccggtaac tatcgtcttg agtccaaccc ggtaagacac gacttatcgc cactggcagc    5820
agccactggt aacaggatta gcagagcgag gtatgtaggc ggtgctacag agttcttgaa    5880
gtggtggcct aactacggct acactagaag aacagtattt ggtatctgcg ctctgctgaa    5940
gccagttacc ttcggaaaaa gagttggtag ctcttgatcc ggcaaacaaa ccaccgctgg    6000
tagcggtggt ttttttgttt gcaagcagca gattacgcgc agaaaaaaag gatctcaaga    6060
agatcctttg atcttttcta cggggtctga cgctcagtgg aacgaaaact cacgttaagg    6120
gattttggtc atgagattat caaaaaggat cttcacctag atccttttaa attaaaaatg    6180
aagttttaaa tcaatctaaa gtatatatga gtaaacttgg tctgacagcg ccgcaaatg    6240 ctaaaccact gcagtggtta ccagtgcttg atcagtgagg caccgatctc agcgatctgc    6300
ctatttcgtt cgtccatagt ggcctgactc cccgtcgtgt agatcactac gattcgtgag    6360
ggcttaccat caggcccag cgcagcaatg atgccgcgag agccgcgttc accggccccc    6420
gatttgtcag caatgaacca gccagcaggg agggccgagc gaagaagtgg tcctgctact    6480
ttgtccgcct ccatccagtc tatgagctgc tgtcgtgatg ctagagtaag aagttcgcca    6540
gtgagtagtt tccgaagagt tgtggccatt gctactggca tcgtggtatc acgtcgtcg    6600 ttcggtatgg cttcgttcaa ctctggttcc cagcggtcaa gccgggtcac atgatcaccc    6660
```

| | |
|---|---:|
| atattatgaa gaaatgcagt cagctcctta gggcctccga tcgttgtcag aagtaagttg | 6720 |
| gccgcggtgt tgtcgctcat ggtaatggca gcactacaca attctcttac cgtcatgcca | 6780 |
| tccgtaagat gcttttccgt gaccggcgag tactcaacca agtcgttttg tgagtagtgt | 6840 |
| atacggcgac caagctgctc ttgcccggcg tctatacggg acaacaccgc gccacatagc | 6900 |
| agtactttga aagtgctcat catcgggaat cgttcttcgg ggcggaaaga ctcaaggatc | 6960 |
| ttgccgctat tgagatccag ttcgatatag cccactcttg cacccagttg atcttcagca | 7020 |
| tcttttactt tcaccagcgt ttcggggtgt gcaaaaacag gcaagcaaaa tgccgcaaag | 7080 |
| aagggaatga gtgcgacacg aaaatgttgg atgctcatac tcgtccttt tcaatattat | 7140 |
| tgaagcattt atcagggtta ctagtacgtc tctcaaggat aagtaagtaa tattaaggta | 7200 |
| cgggaggtat tggacaggcc gcaataaaat atctttattt tcattacatc tgtgtgttgg | 7260 |
| tttttttgtgt gaatcgatag tactaacata cgctctccat caaaacaaaa cgaaacaaaa | 7320 |
| caaactagca aaataggctg tccccagtgc aagtgcaggt gccagaacat ttctct | 7376 |

<210> SEQ ID NO 5
<211> LENGTH: 1188
<212> TYPE: DNA
<213> ORGANISM: Artificial Sequence
<220> FEATURE:
<223> OTHER INFORMATION: RegCG
<220> FEATURE:
<221> NAME/KEY: promoter
<222> LOCATION: (1)..(1188)

<400> SEQUENCE: 5

| | |
|---|---:|
| ggagaggggg taaaaaaatg ctgcactgtg cggctaggcc ggtgagtgag cggcgcggag | 60 |
| ccaatcagcg ctcgccgttc cgaaagttgc cttttatggc tcgagtggcc gctgtggcgt | 120 |
| cctataaaac ccggcggcgc aacgcgcagc cactgtcgag tccgcgtcca cccgcgagca | 180 |
| caggcctttc gcagctcttt cttcgccgct ccacacccgc caccaggtaa gcagggacaa | 240 |
| caggcccagc cggccacagc cctcccgtgg gcagtgaccg cgctgcaggg tcgcggggga | 300 |
| cactcggcgc ggacaccggg gaaggctgga gggtggtgcc gggccgcgga gcggacactt | 360 |
| tcagatccaa ctttcagtcc agggtgtaga cccttacag ccgcattgcc acggtgtaga | 420 |
| caccggtgga cccgctctgg ctcagagcac gcggcttggg ggaacccatt agggtcgcag | 480 |
| tgtgggcgct atgagagccg atgcagcttt cgggtgttga accgtatctg cccaccttgg | 540 |
| ggggaggaca caaggtcggg agccaaacgc cacgatcatg ccttggtggc ccatgggtct | 600 |
| ttgtctaaac cggtttgccc atttggcttg ccgggcgggc gggcgcggcg ggcccggctc | 660 |
| ggccgggttg ggggctgggt tgccactgcg cttgcgcgct ctatggctgg gtattggggc | 720 |
| gcgtgcacgc tggggaggga gcccttcctc ttccccctct cccaagttaa acttgcgcgt | 780 |
| gcgtattgag acttggagcg cggccaccgg ggttgggcga gggcggggcc gttgtccgga | 840 |
| aggggcgggg tcgcagcggc ttcggggcgc ctgctcgcgc ttcctgctgg gtgtggtcgc | 900 |
| ctcccgcgcg cgcactagcc gcccgccggc ggggcgaagg cggggcttgc gcccgtttgg | 960 |
| ggaggggcg gaggcctggc ttcctgccgt ggggccgcct ccggaccagc gtttgcctct | 1020 |
| tatggtaata cgcggccgg cctggcttc cttttgtcccc tgagtttggg cgcgcgcccc | 1080 |
| ctggcggccc gaggccgcgg cttgccggaa gtgggcaggg cggcagcggc tgcgcctagt | 1140 |
| ggcccgccag tgaccgcgac cctctttttgt gccctgatat agttcgcc | 1188 |

<210> SEQ ID NO 6

```
<211> LENGTH: 1822
<212> TYPE: DNA
<213> ORGANISM: Artificial Sequence
<220> FEATURE:
<223> OTHER INFORMATION: RegCG-CMV promoter

<400> SEQUENCE: 6 ggagagggggg taaaaaaatg ctgcactgtg cggctaggcc ggtgagtgag cggcgcggag        60
ccaatcagcg ctcgccgttc cgaaagttgc cttttatggc tcgagtggcc gctgtggcgt       120
cctataaaac ccggcggcgc aacgcgcagc cactgtcgag tccgcgtcca cccgcgagca       180
caggcctttc gcagctcttt cttcgccgct ccacacccgc caccaggtaa gcagggacaa       240
caggcccagc cggccacagc cctcccgtgg gcagtgaccg cgctgcaggg tcgcggggga       300
cactcggcgc ggacaccggg gaaggctgga gggtggtgcc gggccgcgga gcggacactt       360
tcagatccaa ctttcagtcc agggtgtaga ccctttacag ccgcattgcc acggtgtaga       420
caccggtgga cccgctctgg ctcagagcac gcggcttggg ggaacccatt agggtcgcag       480
tgtgggcgct atgagagccg atgcagcttt cgggtgttga accgtatctg cccaccttgg       540
ggggaggaca caaggtcggg agccaaacgc cacgatcatg ccttggtggc ccatgggtct       600
ttgtctaaac cggtttgccc atttggcttg ccgggcgggc gggcgcggcg ggcccggctc       660
ggccgggttg ggggctgggt tgccactgcg cttgcgcgct ctatggctgg gtattggggc       720
gcgtgcacgc tggggaggga gcccttcctc ttcccctct cccaagttaa acttgcgcgt       780
gcgtattgag acttggagcg cggccaccgg ggttgggcga gggcggggcc gttgtccgga       840
aggggcgggg tcgcagcggc ttcggggcgc ctgctcgcgc ttcctgctgg gtgtggtcgc       900
ctcccgcgcg cgcactagcc gcccgccggc ggggcgaagg cggggcttgc gcccgtttgg       960 ggaggggcg gaggcctggc ttcctgccgt ggggccgcct ccggaccagc gtttgcctct      1020
tatggtaata acgcggccgg cctgggcttc ctttgtcccc tgagtttggg cgcgcgcccc      1080
ctggcggccc gaggccgcgg cttgccggaa gtgggcaggg cggcagcggc tgcgcctagt      1140
ggcccgccag tgaccgcgac cctcttttgt gccctgatat agttcgccag atctgttgac      1200
attgattatt gactagttat taatagtaat caattacggg gtcattagtt catagcccat      1260
atatggagtt ccgcgttaca taacttacgg taaatggccc gcctggctga ccgcccaacg      1320 accccccgccc attgacgtca ataatgacgt atgttcccat agtaacgcca atagggactt      1380
tccattgacg tcaatgggtg gagtatttac ggtaaactgc ccacttggca gtacatcaag      1440
tgtatcatat gccaagtacg ccccctattg acgtcaatga cggtaaatgg cccgcctggc      1500
attatgccca gtacatgacc ttatgggact ttcctacttg gcagtacatc tacgtattag      1560
tcatcgctat taccatggtg atgcggtttt ggcagtacat caatgggcgt ggatagcggt      1620
ttgactcacg gggatttcca agtctccacc ccattgacgt caatgggagt ttgttttggc      1680
accaaaatca acgggacttt ccaaaatgtc gtaacaactc cgccccattg acgcaaatgg      1740
gcggtaggcg tgtacggtgg gaggtctata taagcagagc tctctggcta actagagaac      1800
ccactgctta ctggcttatc ga                                              1822

<210> SEQ ID NO 7
<211> LENGTH: 7565
<212> TYPE: DNA
<213> ORGANISM: Artificial Sequence
<220> FEATURE:
<223> OTHER INFORMATION: Seq3a- Luc vector

<400> SEQUENCE: 7
```

-continued

```
ggcctaactg gccggtaccg gagagggggt aaaaaaatgc tgcactgtgc ggctaggccg      60
gtgagtgagc ggcgcggagc caatcagcgc tcgccgttcc gaaagttgcc ttttatggct     120
cgagtggccg ctgtggcgtc ctataaaacc cggcggcgca acgcgcagcc actgtcgagt     180
ccgcgtccac ccgcgagcac aggcctttcg cagctctttc ttcgccgctc cacacccgcc     240
accaggtaag cagggacaac aggcccagcc ggccacagcc ctcccgtggg cagtgaccgc     300
gctgcagggt cgcgggggac actcggcgcg gacaccgggg aaggctggag ggtggtgccg     360
ggccgcggag cggacacttt cagatccaac tttcagtcca gggtgtagac cctttacagc     420
cgcattgcca cggtgtagac accggtggac ccgctctggc tcagagcacg cggcttgggg     480
gaacccatta gggtcgcagt gtgggcgcta tgagagccga tgcagctttc gggtgttgaa     540
ccgtatctgc ccaccttggg gggaggacac aaggtcggga gccaaacgcc acgatcatgc     600
cttggtggcc catgggtctt tgtctaaacc ggtttgccca tttggcttgc gggcgggcg      660
ggcgcggcgg gccggctcg gccgggttgg ggctgggtt ccactgcgc ttgcgcgctc      720
tatgctgggt tattggggcg cgtgcacgct ggggagggag ccttcctct tcccctctc      780
ccaagttaaa cttgcgcgtg cgtattgaga cttggagcgc ggccaccggg gttgggcgag     840
ggcggggccg ttgtccggaa ggggcggggt cgcagcggct tcggggcgcc tgctcgcgct     900
tcctgctggg tgtggtcgcc tcccgcgcgc gcactagccg cccgccggcg gggcgaaggc     960
ggggcttgcg cccgtttggg gaggggggcgg aggcctggct tcctgccgtg gggccgcctc    1020
cggaccagcg tttgcctctt atggtaataa cgccggccgc ctgggcttcc tttgtcccct    1080
gagtttgggc gcgcgccccc tggcggcccg aggccgcggc ttgccggaag tgggcagggc    1140
ggcagcggct gcgcctagtg gccgccagt gaccgcgacc ctcttttgtg ccctgatata    1200
gttcgccgaa ttcgctagca gaacaggatg ttctgatcaa agagatccaa agtcagaaca    1260
cgttgttcta gctaaaataa cacattcaga gaacatgctg ttctgatcaa agagatccaa    1320
agtcagaaca aggtgttcta gctaaaataa cacattcaga gaacatgatg ttctgatcaa    1380
agagatccaa agtcgcggcc gcgttgacat tgattattga ctagttatta atagtaatca    1440
attacgggt cattagttca tagcccatat atggagttcc gcgttacata acttacggta    1500
aatggcccgc ctggctgacc gcccaacgac ccccgcccat tgacgtcaat aatgacgtat    1560
gttcccatag taacgccaat agggactttc cattgacgtc aatgggtgga gtatttacgg    1620
taaactgccc acttggcagt acatcaagtg tatcatatgc caagtacgcc ccctattgac    1680
gtcaatgacg gtaaatggcc cgcctggcat tatgcccagt acatgacctt atgggacttt    1740
cctacttggc agtacatcta cgtattagtc atcgctatta ccatggtgat gcggttttgg    1800
cagtacatca atgggcgtgg atagcggttt gactcacggg gatttccaag tctccacccc    1860
attgacgtca atgggagttt gttttggcac caaaatcaac gggactttcc aaaatgtcgt    1920
aacaactccg ccccattgac gcaaatgggc ggtaggcgtg tacggtggga ggtctatata    1980
agcagagctc tctggctaac tagagaaccc actgcttact ggcttatcga aagcttggca    2040
atccggtact gttggtaaag ccaccatgga agatgccaaa acattaagag agggcccagc    2100
gccattctac ccactcgaag acgggaccgc cggcgagcag ctgcacaaag ccatgaagcg    2160
ctacgccctg gtgcccggca ccatcgcctt taccgacgca catatcgagg tggacattac    2220
ctacgccgag tacttcgaga tgagcgttcg gctggcagaa gctatgaagc gctatgggct    2280
gaatacaaac catcggatcg tggtgtgcag cgagaatagc ttgcagttct tcatgccgt     2340
```

```
gttgggtgcc ctgttcatcg gtgtggctgt ggccccagct aacgacatct acaacgagcg    2400
cgagctgctg aacagcatgg gcatcagcca gcccaccgtc gtattcgtga gcaagaaagg    2460
gctgcaaaag atcctcaacg tgcaaaagaa gctaccgatc atacaaaaga tcatcatcat    2520
ggatagcaag accgactacc agggcttcca aagcatgtac accttcgtga cttcccattt    2580
gccacccggc ttcaacgagt acgacttcgt gcccgagagc ttcgaccggg acaaaaccat    2640
cgccctgatc atgaacagta gtggcagtac cggattgccc aagggcgtag ccctaccgca    2700
ccgcaccgct tgtgtccgat tcagtcatgc ccgcgacccc atcttcggca accagatcat    2760
ccccgacacc gctatcctca gcgtggtgcc atttcaccac ggcttcggca tgttcaccac    2820
gctgggctac ttgatctgcg gctttcgggt cgtgctcatg taccgcttcg aggaggagct    2880
attcttgcgc agcttgcaag actataagat tcaatctgcc ctgctggtgc ccacactatt    2940
tagcttcttc gctaagagca ctctcatcga caagtacgac ctaagcaact tgcacgagat    3000
cgccagcggc ggggcgccgc tcagcaagga ggtaggtgag gccgtggcca acgcttcca    3060 cctaccaggc atccgccagg gctacggcct gacagaaaca accagcgcca ttctgatcac    3120
ccccgaaggg gacgacaagc ctggcgcagt aggcaaggtg gtgcccttct tcgaggctaa    3180
ggtggtggac ttggacaccg gtaagacact gggtgtgaac cagcgcggcg agctgtgcgt    3240
ccgtggcccc atgatcatga gcggctacgt taacaacccc gaggctacaa acgctctcat    3300
cgacaaggac ggctggctgc acagcggcga catcgcctac tgggacgagg acgagcactt    3360
cttcatcgtg gaccggctga agagcctgat caaatacaag ggctaccagg tagccccagc    3420
cgaactggag agcatcctgc tgcaacaccc caacatcttc gacgccgggg tcgccggcct    3480
gcccgacgac gatgccggcg agctgcccgc cgcagtcgtc gtgctggaac acggtaaaac    3540
catgaccgag aaggagatcg tggactatgt ggccagccag gttacaaccg ccaagaagct    3600
gcgcggtggt gttgtgttcg tggacgaggt gcctaaagga ctgaccggca gttggacgc    3660 ccgcaagatc cgcgagattc tcattaaggc caagaagggc ggcaagatcg ccgtgtaata    3720
attctagagt cggggcggcc ggccgcttcg agcagacatg ataagataca ttgatgagtt    3780
tggacaaacc acaactagaa tgcagtgaaa aaaatgcttt atttgtgaaa tttgtgatgc    3840
tattgcttta tttgtaacca ttataagctg caataaacaa gttaacaaca caattgcat    3900 tcattttatg tttcaggttc agggggaggt gtgggaggtt ttttaaagca agtaaaacct    3960
ctacaaatgt ggtaaaatcg ataaggatcc gtttgcgtat gggcgctct tccgctgatc    4020 tgcgcagcac catggcctga ataacctct gaaagaggaa cttggttagc taccttctga    4080
ggcggaaaga accagctgtg aatgtgtgt cagttagggt gtggaaagtc cccaggctcc    4140
ccagcaggca gaagtatgca aagcatgcat ctcaattagt cagcaaccag gtgtggaaag    4200
tccccaggct ccccagcagg cagaagtatg caaagcatgc atctcaatta gtcagcaacc    4260
atagtcccgc ccctaactcc gcccatcccg ccctaactc cgcccagttc cgcccattct    4320
ccgccccatg gctgactaat ttttttatt tatgcagagg ccgaggccgc ctctgcctct    4380
gagctattcc agaagtagtg aggaggcttt tttggaggcc taggcttttg caaaaagctc    4440
gattcttctg acactagcgc caccatgatc gaacaagacg gcctccatgc tggcagtccc    4500
gcagcttggg tcgaacgctt gttcgggtac gactgggccc agcagaccat cggatgtagc    4560
gatgcggccg tgttccgtct aagcgctcaa ggccggcccg tgctgttcgt gaagaccgac    4620
ctgagcggcg ccctgaacga gcttcaagac gaggctgccc gctgagctg ctgccacc    4680 accggcgtac cctgcgccgc tgtgttggat gttgtgaccg aagccggccg ggactggctg    4740
```

```
ctgctgggcg aggtccctgg ccaggatctg ctgagcagcc accttgcccc cgctgagaag    4800
gtttctatca tggccgatgc aatgcggcgc ctgcacaccc tggaccccgc tacctgcccc    4860
ttcgaccacc aggctaagca tcggatcgag cgtgctcgga cccgcatgga ggccggcctg    4920
gtggaccagg acgacctgga cgaggagcat cagggcctgg cccccgctga actgttcgcc    4980
cgactgaaag cccgcatgcc ggacggtgag gacctggttg tcacacacgg agatgcctgc    5040
ctccctaaca tcatggtcga gaatggccgc ttctccggct tcatcgactg cggtcgccta    5100
ggagttgccg accgctacca ggacatcgcc ctggccaccc gcgacatcgc tgaggagctt    5160
ggcggcgagt gggccgaccg cttcttagtc ttgtacggca tcgcagctcc cgacagccag    5220
cgcatcgcct tctaccgctt gctcgacgag ttcttttaat gatctagaac cggtcatggc    5280
cgcaataaaa tatctttatt ttcattacat ctgtgtgttg gttttttgtg tgttcgaact    5340
agatgctgtc gaccgatgcc cttgagagcc ttcaacccag tcagctcctt ccggtgggcg    5400
cggggcatga ctatcgtcgc cgcacttatg actgtcttct ttatcatgca actcgtagga    5460
caggtgccgg cagcgctctt ccgcttcctc gctcactgac tcgctgcgct cggtcgttcg    5520
gctgcggcga gcggtatcag ctcactcaaa ggcggtaata cggttatcca cagaatcagg    5580
ggataacgca ggaaagaaca tgtgagcaaa aggccagcaa aaggccagga accgtaaaaa    5640
ggccgcgttg ctggcgtttt tccataggct ccgcccccct gacgagcatc acaaaaatcg    5700
acgctcaagt cagaggtggc gaaacccgac aggactataa agataccagg cgtttccccc    5760
tggaagctcc ctcgtgcgct ctcctgttcc gaccctgccg cttaccggat acctgtccgc    5820 cttctccct tcgggaagcg tggcgctttc tcatagctca cgctgtaggt atctcagttc    5880
ggtgtaggtc gttcgctcca agctgggctg tgtgcacgaa ccccccgttc agcccgaccg    5940
ctgcgcctta tccggtaact atcgtcttga gtccaacccg gtaagacacg acttatcgcc    6000
actggcagca gccactggta acaggattag cagagcgagg tatgtaggcg gtgctacaga    6060
gttcttgaag tggtggccta actacggcta cactagaaga acagtatttg gtatctgcgc    6120
tctgctgaag ccagttacct tcggaaaaag agttggtagc tcttgatccg gcaaacaaac    6180
caccgctggt agcggtggtt tttttgtttg caagcagcag attacgcgca gaaaaaaagg    6240
atctcaagaa gatcctttga tcttttctac ggggtctgac gctcagtgga acgaaaactc    6300
acgttaaggg attttggtca tgagattatc aaaaaggatc ttcacctaga tccttttaaa    6360
ttaaaaatga agttttaaat caatctaaag tatatatgag taaacttggt ctgacagcgg    6420
ccgcaaatgc taaaccactg cagtggttac cagtgcttga tcagtgaggc accgatctca    6480
gcgatctgcc tatttcgttc gtccatagtg gcctgactcc ccgtcgtgta gatcactacg    6540
attcgtgagg gcttaccatc aggccccagc gcagcaatga tgccgcgaga gccgcgttca    6600
ccggcccccg atttgtcagc aatgaaccag ccagcaggga gggccgagcg aagaagtggt    6660
cctgctactt tgtccgcctc catccagtct atgagctgct gtcgtgatgc tagagtaaga    6720
agttcgccag tgagtagttt ccgaagagtt gtggccattg ctactggcat cgtggtatca    6780
cgctcgtcgt tcggtatggc ttcgttcaac tctggttccc agcggtcaag ccgggtcaca    6840
tgatcaccca tattatgaag aaatgcagtc agctccttag ggcctccgat cgttgtcaga    6900
agtaagttgg ccgcggtgtt gtcgctcatg gtaatggcag cactacacaa ttctcttacc    6960
gtcatgccat ccgtaagatg cttttccgtg accggcgagt actcaaccaa gtcgttttgt    7020
gagtagtgta tacggcgacc aagctgctct tgcccggcgt ctatacggga caacaccgcg    7080
```

| | |
|---|---|
| ccacatagca gtactttgaa agtgctcatc atcgggaatc gttcttcggg gcggaaagac | 7140 |
| tcaaggatct tgccgctatt gagatccagt tcgatatagc ccactcttgc acccagttga | 7200 |
| tcttcagcat cttttacttt caccagcgtt tcggggtgtg caaaaacagg caagcaaaat | 7260 |
| gccgcaaaga agggaatgag tgcgacacga aaatgttgga tgctcatact cgtccttttt | 7320 |
| caatattatt gaagcattta tcagggttac tagtacgtct ctcaaggata agtaagtaat | 7380 |
| attaaggtac gggaggtatt ggacaggccg caataaaata tctttatttt cattacatct | 7440 |
| gtgtgttggt tttttgtgtg aatcgatagt actaacatac gctctccatc aaaacaaaac | 7500 |
| gaaacaaaac aaactagcaa aataggctgt ccccagtgca agtgcaggtg ccagaacatt | 7560 |
| tctct | 7565 |

<210> SEQ ID NO 8
<211> LENGTH: 175
<212> TYPE: DNA
<213> ORGANISM: Artificial Sequence
<220> FEATURE:
<223> OTHER INFORMATION: Tandem of glucocorticoid response elements
      (GRE)

<400> SEQUENCE: 8

| | |
|---|---|
| agaacaggat gttctgatca aagagatcca aagtcagaac acgttgttct agctaaaata | 60 |
| acacattcag agaacatgct gttctgatca aagagatcca aagtcagaac aaggtgttct | 120 |
| agctaaaata acacattcag agaacatgat gttctgatca aagagatcca aagtc | 175 |

<210> SEQ ID NO 9
<211> LENGTH: 2011
<212> TYPE: DNA
<213> ORGANISM: Artificial Sequence
<220> FEATURE:
<223> OTHER INFORMATION: RegCG-GRE-CMV promoter

<400> SEQUENCE: 9

| | |
|---|---|
| ggagaggggg taaaaaaatg ctgcactgtg cggctaggcc ggtgagtgag cggcgcggag | 60 |
| ccaatcagcg ctcgccgttc cgaaagttgc cttttatggc tcgagtggcc gctgtggcgt | 120 |
| cctataaaac ccggcggcgc aacgcgcagc cactgtcgag tccgcgtcca cccgcgagca | 180 |
| caggcctttc gcagctcttt cttcgccgct ccacacccgc caccaggtaa gcagggacaa | 240 |
| caggcccagc cggccacagc cctcccgtgg gcagtgaccg cgctgcaggg tcgcggggga | 300 |
| cactcggcgc ggacaccggg gaaggctgga gggtggtgcc gggccgcgga gcggacactt | 360 |
| tcagatccaa ctttcagtcc agggtgtaga cccttacag ccgcattgcc acggtgtaga | 420 |
| caccggtgga cccgctctgg ctcagagcac gcggcttggg ggaacccatt agggtcgcag | 480 |
| tgtgggcgct atgagagccg atgcagcttt cgggtgttga accgtatctg cccaccttgg | 540 |
| ggggaggaca caaggtcggg agccaaacgc cacgatcatg ccttggtggc ccatgggtct | 600 |
| ttgtctaaac cggtttgccc atttggcttg ccggcgggg gggcgcggcg ggcccggctc | 660 |
| ggccgggttg ggggctgggt tgccactgcg cttgcgcgct ctatggctgg gtattgggc | 720 |
| gcgtgcacgc tggggaggga gcccttcctc ttccccctct cccaagttaa acttgcgcgt | 780 |
| gcgtattgag acttggagcg cggccaccgg ggttgggcga gggcggggcc gttgtccgga | 840 |
| aggggcgggg tcgcagcggc ttcgggcgc ctgctcgcgc ttcctgctgg gtgtggtcgc | 900 |
| ctcccgcgcg cgcactagcc gcccgccggc ggggcgaagg cggggcttgc gcccgtttgg | 960 |
| ggaggggggcg gaggcctggc ttcctgccgt ggggccgcct ccggaccagc gtttgcctct | 1020 |

| | | |
|---|---|---|
| tatggtaata acgcggccgg cctgggcttc ctttgtcccc tgagtttggg cgcgcgcccc | 1080 | |
| ctggcggccc gaggccgcgg cttgccggaa gtgggcaggg cggcagcggc tgcgcctagt | 1140 | |
| ggcccgccag tgaccgcgac cctcttttgt gccctgatat agttcgccga attcgctagc | 1200 | |
| agaacaggat gttctgatca aagagatcca aagtcagaac acgttgttct agctaaaata | 1260 | |
| acacattcag agaacatgct gttctgatca aagagatcca aagtcagaac aaggtgttct | 1320 | |
| agctaaaata acacattcag agaacatgat gttctgatca aagagatcca aagtcgcggc | 1380 | |
| cgcgttgaca ttgattattg actagttatt aatagtaatc aattacgggg tcattagttc | 1440 | |
| atagcccata tatggagttc cgcgttacat aacttacggt aaatggcccg cctggctgac | 1500 | |
| cgcccaacga ccccccgccca ttgacgtcaa taatgacgta tgttcccata gtaacgccaa | 1560 | |
| tagggacttt ccattgacgt caatgggtgg agtatttacg gtaaactgcc cacttggcag | 1620 | |
| tacatcaagt gtatcatatg ccaagtacgc cccctattga cgtcaatgac ggtaaatggc | 1680 | |
| ccgcctggca ttatgcccag tacatgacct tatgggactt tcctacttgg cagtacatct | 1740 | |
| acgtattagt catcgctatt accatggtga tgcggttttg gcagtacatc aatgggcgtg | 1800 | |
| gatagcggtt tgactcacgg ggatttccaa gtctccaccc cattgacgtc aatgggagtt | 1860 | |
| tgttttggca ccaaaatcaa cgggactttc caaaatgtcg taacaactcc gccccattga | 1920 | |
| cgcaaatggg cggtaggcgt gtacggtggg aggtctatat aagcagagct ctctggctaa | 1980 | |
| ctagagaacc cactgcttac tggcttatcg a | 2011 | |

<210> SEQ ID NO 10
<211> LENGTH: 7609
<212> TYPE: DNA
<213> ORGANISM: Artificial Sequence
<220> FEATURE:
<223> OTHER INFORMATION: Seq3b-Luc vector

<400> SEQUENCE: 10

| | | |
|---|---|---|
| ggcctaactg gccggtacct gagctcgcta gcggagaggg ggtaaaaaaa tgctgcactg | 60 | |
| tgcggctagg ccggtgagtg agcggcgcgg agccaatcag cgctcgccgt tccgaaagtt | 120 | |
| gcctttatg gctcgagtgg ccgctgtggc gtcctataaa accggcggc gcaacgcgca | 180 | |
| gccactgtcg agtccgcgtc cacccgcgag cacaggcctt tcgcagctct tcttcgccg | 240 | |
| ctccacaccc gccaccaggt aagcagggac aacaggccca gccggccaca gccctcccgt | 300 | |
| gggcagtgac cgcgctgcag ggtcgcgggg gacactcggc gcggacaccg gggaaggctg | 360 | |
| gagggtggtg ccgggccgcg gagcggacac tttcagatcc aactttcagt ccagggtgta | 420 | |
| gacccttta c agccgcattg ccacggtgta gacaccggtg gacccgctct ggctcagagc | 480 | |
| acgcggcttg ggggaaccca ttagggtcgc agtgtgggcg ctatgagagc cgatgcagct | 540 | |
| ttcgggtgtt gaaccgtatc tgcccacctt ggggggagga cacaaggtcg ggagccaaac | 600 | |
| gccacgatca tgccttggtg gcccatgggt ctttgtctaa accggtttgc ccatttggct | 660 | |
| tgccgggcgg gcgggcgcgg cgggcccggc tcggccgggt tggggctgg gttgccactg | 720 | |
| cgcttgcgcg ctctatggct gggtattggg gcgcgtgcac gctggggagg gagcccttcc | 780 | |
| tcttcccct ctcccaagtt aaacttgcgc gtgcgtattg agactggag gcggccacc | 840 | |
| ggggttgggc gagggcgggg ccgttgtccg gaaggggcgg ggtcgcagcg gcttcgggc | 900 | |
| gcctgctcgc gcttcctgct gggtgtggtc gcctccgcg cgcgcactag ccgcccgccg | 960 | |
| gcggggcgaa ggcggggctt gcgcccgttt ggggagggg cggaggcctg gcttcctgcc | 1020 | |
| gtggggccgc ctccggacca gcgtttgcct cttatggtaa taacgcggcc ggcctgggct | 1080 | |

```
tcctttgtcc cctgagtttg ggcgcgcgcc cctggcggc ccgaggccgc ggcttgccgg    1140
aagtgggcag ggcggcagcg gctgcgccta gtggcccgcc agtgaccgcg accctctttt    1200
gtgccctgat atagttcgcc gaattctttt ttgcggccgc gttgacattg attattgact    1260
agttattaat agtaatcaat tacggggtca ttagttcata gcccatatat ggagttccgc    1320
gttacataac ttacggtaaa tggcccgcct ggctgaccgc ccaacgaccc ccgcccattg    1380
acgtcaataa tgacgtatgt tcccatagta acgccaatag ggactttcca ttgacgtcaa    1440
tgggtggagt atttacggta aactgcccac ttggcagtac atcaagtgta tcatatgcca    1500
agtacgcccc ctattgacgt caatgacggt aaatggcccg cctggcatta tgcccagtac    1560
atgaccttat gggactttcc tacttggcag tacatctacg tattagtcat cgctattacc    1620
atggtgatgc ggttttggca gtacatcaat gggcgtggat agcggtttga ctcacgggga    1680
tttccaagtc tccaccccat tgacgtcaat gggagtttgt tttggcacca aaatcaacgg    1740
gactttccaa aatgtcgtaa caactccgcc ccattgacgg ctagcagaac aggatgttct    1800
gatcaaagag atccaaagtc agaacacgtt gttctagcta aaataacaca ttcagagaac    1860
atgctgttct gatcaaagag atccaaagtc agaacaaggt gttctagcta aaataacaca    1920
ttcagagaac atgatgttct gatcaaagag atccaaagtc ctcgaggata tcaagatctg    1980
caaatcaaat gggcggtagg cgtgtacggt gggaggtcta taagcaga gctctctggc    2040 taactagaga acccactgct tactggctta tcgaaagctt ggcaatccgg tactgttggt    2100
aaagccacca tggaagatgc caaaaacatt aagaagggcc cagcgccatt ctacccactc    2160
gaagacggga ccgccggcga gcagctgcac aaagccatga agcgctacgc cctggtgccc    2220
ggcaccatcg cctttaccga cgcacatatc gaggtggaca ttacctacgc cgagtacttc    2280
gagatgagcg ttcggctggc agaagctatg aagcgctatg gctgaatac aaaccatcgg    2340 atcgtggtgt gcagcgagaa tagcttgcag ttcttcatgc ccgtgttggg tgccctgttc    2400
atcggtgtgg ctgtggcccc agctaacgac atctacaacg agcgcgagct gctgaacagc    2460
atgggcatca gccagcccac cgtcgtattc gtgagcaaga agggctgca aaagatcctc    2520 aacgtgcaaa agaagctacc gatcatacaa agatcatca tcatggatag caagaccgac    2580
taccagggct tccaaagcat gtacaccttc gtgacttccc atttgccacc cggcttcaac    2640
gagtacgact tcgtgcccga gagcttcgac cgggacaaaa ccatcgccct gatcatgaac    2700
agtagtggca gtaccggatt gcccaagggc gtagccctac cgcaccgcac cgcttgtgtc    2760
cgattcagtc atgcccgcga ccccatcttc ggcaaccaga tcatccccga caccgctatc    2820
ctcagcgtgg tgccatttca ccacggcttc ggcatgttca ccacgctggg ctacttgatc    2880
tgcggctttc gggtcgtgct catgtaccgc ttcgaggagg agctattctt gcgcagcttg    2940
caagactata agattcaatc tgccctgctg gtgcccacac tatttagctt cttcgctaag    3000
agcactctca tcgacaagta cgacctaagc aacttgcacg agatcgccag cggcggggcg    3060
ccgctcagca aggaggtagg tgaggccgtg gccaaacgct tccacctacc aggcatccgc    3120
cagggctacg gcctgacaga aacaaccagc gccattctga tcaccccgga aggggacgac    3180
aagcctggcg cagtaggcaa ggtggtgccc ttcttcgagg ctaaggtggt ggacttggac    3240
accggtaaga cactgggtgt gaaccagcgc ggcgagctgt gcgtccgtgg ccccatgatc    3300
atgagcggct acgttaacaa ccccgaggct acaaacgctc tcatcgacaa ggacggctgg    3360
ctgcacagcg gcgacatcgc ctactgggac gaggacgagc acttcttcat cgtggaccgg    3420
```

```
ctgaagagcc tgatcaaata caagggctac caggtagccc cagccgaact ggagagcatc     3480
ctgctgcaac accccaacat cttcgacgcc ggggtcgccg gcctgcccga cgacgatgcc     3540
ggcgagctgc ccgccgcagt cgtcgtgctg gaacacggta aaaccatgac cgagaaggag     3600
atcgtggact atgtgccagc ccaggttaca accgccaaga agctgcgcgg tggtgttgtg     3660
ttcgtggacg aggtgcctaa aggactgacc ggcaagttgg acgcccgcaa gatccgcgag     3720
attctcatta aggccaagaa gggcggcaag atcgccgtgt aataattcta gagtcggggc     3780
ggccggccgc ttcgagcaga catgataaga tacattgatg agtttggaca aaccacaact     3840
agaatgcagt gaaaaaaatg ctttatttgt gaaatttgtg atgctattgc tttatttgta     3900
accattataa gctgcaataa acaagttaac aacaacaatt gcattcattt tatgtttcag     3960
gttcaggggg aggtgtggga ggttttttaa agcaagtaaa acctctacaa atgtggtaaa     4020
atcgataagg atccgtttgc gtattgggcg ctcttccgct gatctgcgca gcaccatggc     4080
ctgaaataac ctctgaaaga ggaacttggt tagctaccct ctgaggcgga agaaccagc      4140 tgtggaatgt gtgtcagtta gggtgtggaa agtccccagg ctccccagca ggcagaagta     4200
tgcaaagcat gcatctcaat tagtcagcaa ccaggtgtgg aaagtcccca ggctccccag     4260
caggcagaag tatgcaaagc atgcatctca attagtcagc aaccatagtc ccgcccctaa     4320
ctccgcccat cccgcccta actccgccca gttccgccca ttctccgccc catggctgac      4380 taatttttttt tatttatgca gaggccgagg ccgcctctgc ctctgagcta ttccagaagt    4440
agtgaggagg ctttttttgga ggcctaggct tttgcaaaaa gctcgattct tctgacacta    4500
gcgccaccat gatcgaacaa gacggcctcc atgctggcag tcccgcagct gggtcgaac      4560 gcttgttcgg gtacgactgg gcccagcaga ccatcggatg tagcgatgcg gccgtgttcc     4620
gtctaagcgc tcaaggccgg cccgtgctgt tcgtgaagac cgacctgagc ggcgccctga     4680
acgagcttca agacgaggct gcccgcctga gctggctggc caccaccggc gtacctgcg     4740 ccgctgtgtt ggatgttgtg accgaagccg gcgggactg gctgctgctg ggcgaggtcc     4800
ctggccagga tctgctgagc agccaccttg cccccgctga aaggtttct atcatggccg     4860 atgcaatgcg gcgcctgcac accctggacc ccgctacctg cccccttcgac caccaggcta    4920 agcatcggat cgagcgtgct cggacccgca tggaggccgg cctggtggac caggacgacc    4980
tggacgagga gcatcagggc ctggccccg ctgaactgtt cgcccgactg aaagcccgca     5040
tgccggacgg tgaggacctg gttgtcacac acggagatgc ctgcctccct aacatcatgg    5100
tcgagaatgg ccgcttctcc ggcttcatcg actgcgggtcg cctaggagtt gccgaccgct    5160
accaggacat cgccctggcc acccgcgaca tcgctgagga gcttggcggc gagtgggccg    5220
accgcttctt agtcttgtac ggcatcgcag ctcccgacag ccagcgcatc gccttctacc    5280
gcttgctcga cgagttcttt taatgatcta gaaccggtca tggccgcaat aaaatatctt    5340
tattttcatt acatctgtgt gttggttttt tgtgtgttcg aactagatgc tgtcgaccga    5400
tgcccttgag agccttcaac ccagtcagct ccttccggtg ggcgcgggc atgactatcg      5460 tcgccgcact tatgactgtc ttctttatca tgcaactcgt aggacaggtg ccggcagcgc    5520
tcttccgctt cctcgctcac tgactcgctg cgctcggtcg ttcggctgcg gcgagcggta    5580
tcagctcact caaaggcggt aatacggtta tccacagaat caggggataa cgcaggaaag    5640
aacatgtgag caaaaggcca gcaaaaggcc aggaaccgta aaaaggccgc gttgctggcg    5700
tttttccata ggctccgccc ccctgacgag catcacaaaa atcgacgctc aagtcagagg    5760
tggcgaaacc cgacaggact ataaagatac caggcgtttc ccctggaag ctccctcgtg      5820
```

```
cgctctcctg ttccgaccct gccgcttacc ggatacctgt ccgcctttct cccttcggga    5880
agcgtggcgc tttctcatag ctcacgctgt aggtatctca gttcggtgta ggtcgttcgc    5940
tccaagctgg gctgtgtgca cgaaccccc  gttcagcccg accgctgcgc cttatccggt    6000
aactatcgtc ttgagtccaa cccggtaaga cacgacttat cgccactggc agcagccact    6060
ggtaacagga ttagcagagc gaggtatgta ggcggtgcta cagagttctt gaagtggtgg    6120
cctaactacg gctacactag aagaacagta tttggtatct gcgctctgct gaagccagtt    6180
accttcggaa aaagagttgg tagctcttga tccggcaaac aaaccaccgc tggtagcggt    6240
ggtttttttg tttgcaagca gcagattacg cgcagaaaaa aaggatctca agaagatcct    6300
ttgatctttt ctacggggtc tgacgctcag tggaacgaaa actcacgtta agggattttg    6360
gtcatgagat tatcaaaaag gatcttcacc tagatccttt taaattaaaa atgaagtttt    6420
aaatcaatct aaagtatata tgagtaaact tggtctgaca gcggccgcaa atgctaaacc    6480
actgcagtgg ttaccagtgc ttgatcagtg aggcaccgat ctcagcgatc tgcctatttc    6540
gttcgtccat agtggcctga ctccccgtcg tgtagatcac tacgattcgt gagggcttac    6600
catcaggccc cagcgcagca atgatgccgc gagagccgcg ttcaccggcc ccgatttgt    6660 cagcaatgaa ccagccagca gggagggccg agcgaagaag tggtcctgct actttgtccg    6720
cctccatcca gtctatgagc tgctgtcgtg atgctagagt aagaagttcg ccagtgagta    6780
gtttccgaag agttgtggcc attgctactg gcatcgtggt atcacgctcg tcgttcggta    6840
tggcttcgtt caactctggt tcccagcggt caagccgggt cacatgatca cccatattat    6900
gaagaaatgc agtcagctcc ttagggcctc cgatcgttgt cagaagtaag ttggccgcgg    6960
tgttgtcgct catggtaatg gcagcactac acaattctct taccgtcatg ccatccgtaa    7020
gatgcttttc cgtgaccggc gagtactcaa ccaagtcgtt ttgtgagtag tgtatacggc    7080
gaccaagctg ctcttgcccg gcgtctatac gggacaacac cgcgccacat agcagtactt    7140
tgaaagtgct catcatcggg aatcgttctt cggggcggaa agactcaagg atcttgccgc    7200
tattgagatc cagttcgata tagcccactc ttgcacccag ttgatcttca gcatctttta    7260
cttccaccag cgtttcgggg tgtgcaaaaa caggcaagca aaatgccgca agaagggaa    7320 tgagtgcgac acgaaaatgt tggatgctca tactcgtcct ttttcaatat tattgaagca    7380
tttatcaggg ttactagtac gtctctcaag gataagtaag taatattaag gtacgggagg    7440
tattggacag gccgcaataa aatatcttta ttttcattac atctgtgtgt tggtttttg    7500 tgtgaatcga tagtactaac atacgctctc atcaaaaca  aaacgaaaca aaacaaacta    7560
gcaaaatagg ctgtccccag tgcaagtgca ggtgccagaa catttctct               7609
```

<210> SEQ ID NO 11
<211> LENGTH: 2042
<212> TYPE: DNA
<213> ORGANISM: Artificial Sequence
<220> FEATURE:
<223> OTHER INFORMATION: RegCG-CMV-GRE promoter

<400> SEQUENCE: 11

```
ggagaggggg taaaaaaatg ctgcactgtg cggctaggcc ggtgagtgag cggcgcggag      60
ccaatcagcg ctcgccgttc cgaaagttgc cttttatggc tcgagtggcc gctgtggcgt     120
cctataaaac ccggcggcgc aacgcgcagc cactgtcgag tccgcgtcca cccgcgagca     180
caggcctttc gcagctcttt cttcgccgct ccacacccgc caccaggtaa gcagggacaa     240
```

```
caggcccagc cggccacagc cctcccgtgg gcagtgaccg cgctgcaggg tcgcggggga    300
cactcggcgc ggacaccggg gaaggctgga gggtggtgcc gggccgcgga gcggacactt    360
tcagatccaa cttcagtcc agggtgtaga ccctttacag ccgcattgcc acggtgtaga    420
caccggtgga cccgctctgg ctcagagcac gcggcttggg ggaacccatt agggtcgcag    480
tgtgggcgct atgagagccg atgcagcttt cgggtgttga accgtatctg cccaccttgg    540
ggggaggaca caaggtcggg agccaaacgc cacgatcatg ccttggtggc ccatgggtct    600
ttgtctaaac cggtttgccc atttggcttg ccgggcgggc gggcgcggcg ggcccggctc    660
ggccgggttg ggggctgggt tgccactgcg cttgcgcgct ctatggctgg gtattggggc    720
gcgtgcacgc tggggaggga gcccttcctc ttccccctct cccaagttaa acttgcgcgt    780
gcgtattgag acttggagcg cggccaccgg ggttgggcga gggcggggcc gttgtccgga    840
aggggcgggg tcgcagcggc ttcggggcgc ctgctcgcgc ttcctgctgg gtgtggtcgc    900
ctcccgcgcg cgcactagcc gcccgccggc ggggcgaagg cggggcttgc gcccgtttgg    960
ggaggggcg gaggcctggc ttcctgccgt ggggccgcct ccggaccagc gtttgcctct   1020
tatggtaata acgcggccgg cctgggcttc ctttgtcccc tgagtttggg cgcgcgcccc   1080
ctggcggccc gaggccgcgg cttgccgaaa gtgggcaggg cggcagcggc tgcgcctagt   1140
ggcccgccag tgaccgcgac cctcttttgt gccctgatat agttcgccga attctttttt   1200
gcggccgcgt tgacattgat tattgactag ttattaatag taatcaatta cggggtcatt   1260
agttcatagc ccatatatgg agttccgcgt tacataactt acggtaaatg gcccgcctgg   1320
ctgaccgccc aacgacccc gcccattgac gtcaataatg acgtatgttc ccatagtaac   1380
gccaataggg actttccatt gacgtcaatg ggtggagtat ttacggtaaa ctgcccactt   1440
ggcagtacat caagtgtatc atatgccaag tacgccccct attgacgtca atgacggtaa   1500
atggcccgcc tggcattatg cccagtacat gaccttatgg gactttccta cttggcagta   1560
catctacgta ttagtcatcg ctattaccat ggtgatgcgg ttttggcagt acatcaatgg   1620
gcgtggatag cggtttgact cacggggatt tccaagtctc caccccattg acgtcaatgg   1680
gagtttgttt tggcaccaaa atcaacggga ctttccaaaa tgtcgtaaca actccgcccc   1740
attgacggct agcagaacag gatgttctga tcaaagagat ccaaagtcag aacacgttgt   1800
tctagctaaa ataacacatt cagagaacat gctgttctga tcaaagagat ccaaagtcag   1860
aacaaggtgt tctagctaaa ataacacatt cagagaacat gatgttctga tcaaagagat   1920
ccaaagtcct cgaggatatc aagatctgca aatcaaatgg gcggtaggcg tgtacggtgg   1980
gaggtctata taagcagagc tctctggcta actagagaac ccactgctta ctggcttatc   2040
ga                                                                 2042
```

<210> SEQ ID NO 12
<211> LENGTH: 7786
<212> TYPE: DNA
<213> ORGANISM: Artificial Sequence
<220> FEATURE:
<223> OTHER INFORMATION: Seq3c-Luc vector

<400> SEQUENCE: 12

```
ggcctaactg gccggtacct gagctcgcta gcggagaggg ggtaaaaaaa tgctgcactg     60
tgcggctagg ccggtgagtg agcggcgcgg agccaatcag cgctcgccgt tccgaaagtt    120
gccttttatg gctcgagtgg ccgctgtggc gtcctataaa acccggcggc gcaacgcgca    180
gccactgtcg agtccgcgtc cacccgcgag cacaggcctt tcgcagctct ttcttcgccg    240
```

```
ctccacaccc gccaccaggt aagcagggac aacaggccca gccggccaca gccctcccgt    300
gggcagtgac cgcgctgcag ggtcgcgggg gacactcggc gcggacaccg gggaaggctg    360
gagggtggtg ccgggccgcg gagcggacac tttcagatcc aactttcagt ccagggtgta    420 gacccttta c agccgcattg ccacggtgta gacaccggtg gacccgctct ggctcagagc    480
acgcggcttg ggggaaccca ttagggtcgc agtgtgggcg ctatgagagc cgatgcagct    540
ttcgggtgtt gaaccgtatc tgcccacctt ggggggagga cacaaggtcg ggagccaaac    600
gccacgatca tgccttggtg gcccatgggt ctttgtctaa accggtttgc ccatttggct    660
tgccgggcgg gcgggcgcgg cgggcccggc tcggccgggt tggggctgg gttgccactg    720 cgcttgcgcg ctctatggct gggtattggg gcgcgtgcac gctggggagg gagcccttcc    780 tcttcccct ctcccaagtt aaacttgcgc gtgcgtattg agacttggag cgcggccacc    840
ggggttgggc gagggcgggg ccgttgtccg aaggggcgg ggtcgcagcg gcttcggggc    900
gcctgctcgc gcttcctgct gggtgtggtc gcctcccgcg cgcgcactag ccgcccgccg    960
gcggggcgaa ggcggggctt cgcccgtttt ggggagggg cggaggcctg gcttcctgcc   1020
gtggggccgc ctccggacca gcgtttgcct cttatggtaa taacgcggcc ggcctgggct   1080
tcctttgtcc cctgagtttg ggcgcgcgcc ccctggcggc ccgaggccgc ggcttgccgg   1140
aagtgggcag ggcggcagcg gctgcgccta gtggcccgcc agtgaccgcg accctctttt   1200
gtgccctgat atagttcgcc gaattcagaa caggatgttc tgatcaaaga gatccaaagt   1260
cagaacacgt tgttctagct aaaataacac attcagagaa catgctgttc tgatcaaaga   1320
gatccaaagt cagaacaagg tgttctagct aaaataacac attcagagaa catgatgttc   1380
tgatcaaaga gatccaaagt cctcgaggat atcagcggcc gcgttgacat tgattattga   1440
ctagttatta atagtaatca attacgggt cattagttca tagcccatat atggagttcc   1500
gcgttacata acttacggta aatggcccgc ctggctgacc gcccaacgac ccccgcccat   1560
tgacgtcaat aatgacgtat gttcccatag taacgccaat agggactttc cattgacgtc   1620
aatgggtgga gtatttacgg taaactgccc acttggcagt acatcaagtg tatcatatgc   1680
caagtacgcc ccctattgac gtcaatgacg gtaaatggcc cgcctggcat tatgcccagt   1740
acatgacctt atgggacttt cctacttggc agtacatcta cgtattagtc atcgctatta   1800
ccatggtgat gcggttttgg cagtacatca atgggcgtgg atagcggttt gactcacggg   1860
gatttccaag tctccacccc attgacgtca atgggagttt gttttggcac caaaatcaac   1920
gggactttcc aaaatgtcgt aacaactccg ccccattgac ggctagcaga acaggatgtt   1980
ctgatcaaag atccaaag tcagaacacg ttgttctagc taaaataaca cattcagaga   2040
acatgctgtt ctgatcaaag atccaaagt cagaacaag gtgttctagc taaaataaca   2100
cattcagaga acatgatgtt ctgatcaaag atccaaagt cctcgaggat atcaagatc   2160 tgcaaatggg cggtaggcgt gtacggtggg aggtctatat aagcagagct ctctggctaa   2220
ctagagaacc cactgcttac tggcttatcg aaagcttggc aatccggtac tgttggtaaa   2280
gccaccatgg aagatgccaa aacattaag aagggcccag cgccattcta cccactcgaa   2340
gacgggaccg ccggcgagca gctgcacaaa gccatgaagc gctacgccct ggtgcccggc   2400
accatcgcct ttaccgacgc acatatcgag gtggacatta cctacgccga gtacttcgag   2460
atgagcgttc ggctgcaga agctatgaag cgctatgggc tgaatacaaa ccatcggatc   2520
gtggtgtgca gcgagaatag cttgcagttc ttcatgcccg tgttgggtgc cctgttcatc   2580
```

```
ggtgtggctg tggccccagc taacgacatc tacaacgagc gcgagctgct gaacagcatg    2640
ggcatcagcc agcccaccgt cgtattcgtg agcaagaaag ggctgcaaaa gatcctcaac    2700
gtgcaaaaga agctaccgat catacaaaag atcatcatca tggatagcaa gaccgactac    2760
cagggcttcc aaagcatgta caccttcgtg acttcccatt tgccaccgg cttcaacgag     2820 tacgacttcg tgcccgagag cttcgaccgg gacaaaacca tcgccctgat catgaacagt    2880
agtggcagta ccggattgcc caagggcgta gccctaccgc accgcaccgc ttgtgtccga    2940
ttcagtcatg cccgcgaccc catcttcggc aaccagatca tccccgacac cgctatcctc    3000
agcgtggtgc catttcacca cggcttcggc atgttcacca cgctgggcta cttgatctgc    3060
ggctttcggg tcgtgctcat gtaccgcttc gaggaggagc tattcttgcg cagcttgcaa    3120
gactataaga ttcaatctgc cctgctggtg cccacactat ttagcttctt cgctaagagc    3180
actctcatcg acaagtacga cctaagcaac ttgcacgaga tcgccagcgg cggggcgccg    3240
ctcagcaagg aggtaggtga ggccgtggcc aaacgcttcc acctaccagg catccgccag    3300
ggctacggcc tgacagaaac aaccagcgcc attctgatca cccccgaagg ggacgacaag    3360
cctggcgcag taggcaaggt ggtgcccttc ttcgaggcta aggtggtgga cttggacacc    3420
ggtaagacac tgggtgtgaa ccagcgcggc gagctgtgcg tccgtggccc catgatcatg    3480
agcggctacg ttaacaaccc cgaggctaca aacgctctca tcgacaagga cggctggctg    3540
cacagcggcg acatcgccta ctgggacgag gacgagcact tcttcatcgt ggaccggctg    3600
aagagcctga tcaaatacaa gggctaccag gtagcccag ccgaactgga gagcatcctg    3660
ctgcaacacc ccaacatctt cgacgccggg tcgccggcc tgcccgacga cgatgccggc    3720
gagctgcccg ccgcagtcgt cgtgctggaa cacggtaaaa ccatgaccga aaggagatc    3780 gtggactatg tggccagcca ggttacaacc gccaagaagc tgcgcggtgg tgttgtgttc    3840
gtggacgagg tgcctaaagg actgaccggc aagttggacg cccgcaagat ccgcgagatt    3900
ctcattaagg ccaagaaggg cggcaagatc gccgtgtaat aattctagag tcggggcggc    3960
cggccgcttc gagcagacat gataagatac attgatgagt ttggacaaac cacaactaga    4020
atgcagtgaa aaaaatgctt tatttgtgaa atttgtgatg ctattgcttt atttgtaacc    4080
attataagct gcaataaaca agttaacaac aacaattgca ttcattttat gtttcaggtt    4140 caggggggagg tgtgggaggt tttttaaagc aagtaaaacc tctacaaatg tggtaaaatc    4200
gataaggatc cgtttgcgta ttgggcgctc ttccgctgat ctgcgcagca ccatggcctg    4260
aaataacctc tgaaagagga acttggttag ctaccttctg aggcggaaag aaccagctgt    4320
ggaatgtgtg tcagttaggg tgtggaaagt ccccaggctc cccagcaggc agaagtatgc    4380
aaagcatgca tctcaattag tcagcaacca ggtgtggaaa gtcccaggc tccccagcag    4440 gcagaagtat gcaaagcatg catctcaatt agtcagcaac catagtcccg cccctaactc    4500
cgcccatccc gcccctaact ccgcccagtt ccgcccattc tccgcccat ggctgactaa    4560 ttttttttat ttatgcagag gccgaggccg cctctgcctc tgagctattc cagaagtagt    4620
gaggaggctt ttttggaggc ctaggctttt gcaaaaagct cgattcttct gacactagcg    4680
ccaccatgat cgaacaagac ggcctccatg ctggcagtcc cgcagcttgg gtcgaacgct    4740
tgttcgggta cgactgggcc cagcagacca tcggatgtag cgatgcggcc gtgttccgtc    4800
taagcgctca aggccggccc gtgctgttcg tgaagaccga cctgagcggc ccctgaacg     4860 agcttcaaga cgaggctgcc cgcctgagct ggctggccac caccgggcgta ccctgcgccg    4920 ctgtgttgga tgttgtgacc gaagccggcc gggactggct gctgctgggc gaggtccctg    4980
```

```
gccaggatct gctgagcagc caccttgccc ccgctgagaa ggtttctatc atggccgatg    5040
caatgcggcg cctgcacacc ctggaccccg ctacctgccc cttcgaccac caggctaagc    5100
atcggatcga gcgtgctcgg acccgcatgg aggccggcct ggtggaccag gacgacctgg    5160
acgaggagca tcagggcctg gcccccgctg aactgttcgc ccgactgaaa gcccgcatgc    5220
cggacggtga ggacctggtt gtcacacacg gagatgcctg cctccctaac atcatggtcg    5280
agaatggccg cttctccggc ttcatcgact gcggtcgcct aggagttgcc gaccgctacc    5340
aggacatcgc cctggccacc cgcgacatcg ctgaggagct tggcggcgag tgggccgacc    5400
gcttcttagt cttgtacggc atcgcagctc ccgacagcca gcgcatcgcc ttctaccgct    5460
tgctcgacga gttcttttaa tgatctagaa ccggtcatgg ccgcaataaa atatctttat    5520
tttcattaca tctgtgtgtt ggttttttgt gtgttcgaac tagatgctgt cgaccgatgc    5580
ccttgagagc cttcaaccca gtcagctcct tccggtgggc gcggggcatg actatcgtcg    5640
ccgcacttat gactgtcttc tttatcatgc aactcgtagg acaggtgccg gcagcgctct    5700
tccgcttcct cgctcactga ctcgctgcgc tcggtcgttc ggctgcggcg agcggtatca    5760
gctcactcaa aggcggtaat acggttatcc acagaatcag gggataacgc aggaaagaac    5820
atgtgagcaa aaggccagca aaaggccagg aaccgtaaaa aggccgcgtt gctggcgttt    5880
ttccataggc tccgcccccc tgacgagcat cacaaaaatc gacgctcaag tcagaggtgg    5940
cgaaacccga caggactata agataccag gcgtttcccc ctggaagctc cctcgtgcgc    6000
tctcctgttc cgaccctgcc gcttaccgga tacctgtccg cctttctccc ttcgggaagc    6060
gtggcgcttt ctcatagctc acgctgtagg tatctcagtt cggtgtaggt cgttcgctcc    6120
aagctgggct gtgtgcacga accccccgtt cagcccgacc gctgcgcctt atccggtaac    6180
tatcgtcttg agtccaaccc ggtaagacac gacttatcgc cactggcagc agccactggt    6240
aacaggatta gcagagcgag gtatgtaggc ggtgctacag agttcttgaa gtggtggcct    6300
aactacggct acactagaag aacagtattt ggtatctgcg ctctgctgaa gccagttacc    6360
ttcggaaaaa gagttggtag ctcttgatcc ggcaaacaaa ccaccgctgg tagcggtggt    6420
ttttttgttt gcaagcagca gattacgcgc agaaaaaaag gatctcaaga agatcctttg    6480
atcttttcta cggggtctga cgctcagtgg aacgaaaact cacgttaagg gattttggtc    6540
atgagattat caaaaaggat cttcacctag atccttttaa attaaaaatg aagttttaaa    6600
tcaatctaaa gtatatatga gtaaacttgg tctgacagcg gccgcaaatg ctaaaccact    6660
gcagtggtta ccagtgcttg atcagtgagg caccgatctc agcgatctgc ctatttcgtt    6720
cgtccatagt ggcctgactc cccgtcgtgt agatcactac gattcgtgag gcttaccat    6780 caggccccag cgcagcaatg atgccgcgag agccgcgttc accggccccc gatttgtcag    6840
caatgaacca gccagcaggg agggccgagc gaagaagtgg tcctgctact ttgtccgcct    6900
ccatccagtc tatgagctgc tgtcgtgatg ctagagtaag aagttcgcca gtgagtagtt    6960
tccgaagagt tgtggccatt gctactggca tcgtggtatc acgctcgtcg ttcggtatgg    7020
cttcgttcaa ctctggttcc cagcggtcaa gccgggtcac atgatcaccc atattatgaa    7080
gaaatgcagt cagctcctta gggcctccga tcgttgtcag aagtaagttg gccgcggtgt    7140
tgtcgctcat ggtaatggca gcactacaca attctcttac cgtcatgcca tccgtaagat    7200
gcttttccgt gaccggcgag tactcaacca agtcgtttg tgagtagtgt atacggcgac    7260
caagctgctc ttgcccggcg tctatacggg acaacaccgc gccacatagc agtactttga    7320
```

| | |
|---|---|
| aagtgctcat catcgggaat cgttcttcgg ggcggaaaga ctcaaggatc ttgccgctat | 7380 |
| tgagatccag ttcgatatag cccactcttg cacccagttg atcttcagca tcttttactt | 7440 |
| tcaccagcgt ttcggggtgt gcaaaaacag gcaagcaaaa tgccgcaaag aagggaatga | 7500 |
| gtgcgacacg aaaatgttgg atgctcatac tcgtcctttt tcaatattat tgaagcattt | 7560 |
| atcagggtta ctagtacgtc tctcaaggat aagtaagtaa tattaaggta cgggaggtat | 7620 |
| tggacaggcc gcaataaaat atctttattt tcattacatc tgtgtgttgg ttttttgtgt | 7680 |
| gaatcgatag tactaacata cgctctccat caaaacaaaa cgaaacaaaa caaactagca | 7740 |
| aaataggctg tccccagtgc aagtgcaggt gccagaacat ttctct | 7786 |

<210> SEQ ID NO 13
<211> LENGTH: 2219
<212> TYPE: DNA
<213> ORGANISM: Artificial Sequence
<220> FEATURE:
<223> OTHER INFORMATION: RegCG-GRE-CMV-GRE promoter

<400> SEQUENCE: 13

| | |
|---|---|
| ggagagggggg taaaaaaatg ctgcactgtg cggctaggcc ggtgagtgag cggcgcggag | 60 |
| ccaatcagcg ctcgccgttc cgaaagttgc ctttttatggc tcgagtggcc gctgtggcgt | 120 |
| cctataaaac ccggcggcgc aacgcgcagc cactgtcgag tccgcgtcca cccgcgagca | 180 |
| caggcctttc gcagctcttt cttcgccgct ccacacccgc caccaggtaa gcagggacaa | 240 |
| caggcccagc cggccacagc cctcccgtgg gcagtgaccg cgctgcaggg tcgcggggga | 300 |
| cactcggcgc ggacaccggg gaaggctgga gggtggtgcc gggccgcgga gcggacactt | 360 |
| tcagatccaa ctttcagtcc agggtgtaga ccctttacag ccgcattgcc acggtgtaga | 420 |
| caccggtgga cccgctctgg ctcagagcac gcggcttggg ggaacccatt agggtcgcag | 480 |
| tgtgggcgct atgagagccg atgcagcttt cgggtgttga accgtatctg cccaccttgg | 540 |
| ggggaggaca caaggtcggg agccaaacgc acgatcatg ccttggtggc ccatgggtct | 600 |
| ttgtctaaac cggtttgccc atttggcttg ccgggcgggc gggcgcggcg ggcccggctc | 660 |
| ggccgggttg ggggctgggt tgccactgcg cttgcgcgct ctatggctgg gtattggggc | 720 |
| gcgtgcacgc tggggaggga gcccttcctc ttcccctct cccaagttaa acttgcgcgt | 780 |
| gcgtattgag acttggagcg cggccaccgg ggttgggcga gggcggggcc gttgtccgga | 840 |
| aggggcgggg tcgcagcggc ttcggggcgc ctgctcgcgc ttcctgctgg gtgtggtcgc | 900 |
| ctcccgcgcg cgcactagcc gcccgccggc ggggcgaagg cggggcttgc gcccgtttgg | 960 |
| ggagggggcg gaggcctggc ttcctgccgt ggggccgcct ccggaccagc gtttgcctct | 1020 |
| tatggtaata acgcggccgg cctgggcttc ctttgtcccc tgagtttggg cgcgcgcccc | 1080 |
| ctggcggccc gaggccgcgg cttgccggaa gtgggcaggg cggcagcggc tgcgcctagt | 1140 |
| ggcccgccag tgaccgcgac cctcttttgt gccctgatat agttcgccga attcagaaca | 1200 |
| ggatgttctg atcaaagaga tccaaagtca gaacacgttg ttctagctaa ataacacat | 1260 |
| tcagagaaca tgctgttctg atcaaagaga tccaaagtca gaacaaggtg ttctagctaa | 1320 |
| aataacacat tcagagaaca tgatgttctg atcaaagaga tccaaagtcc tgaggatat | 1380 |
| cagcggccgc gttgacattg attattgact agttattaat agtaatcaat tacggggtca | 1440 |
| ttagttcata gcccatatat ggagttccgc gttacataac ttacggtaaa tggcccgcct | 1500 |
| ggctgaccgc ccaacgaccc ccgcccattg acgtcaataa tgacgtatgt tcccatagta | 1560 |
| acgccaatag ggactttcca ttgacgtcaa tgggtggagt atttacggta aactgcccac | 1620 |

-continued

| | |
|---|---|
| ttggcagtac atcaagtgta tcatatgcca agtacgcccc ctattgacgt caatgacggt | 1680 |
| aaatggcccg cctggcatta tgcccagtac atgaccttat gggactttcc tacttggcag | 1740 |
| tacatctacg tattagtcat cgctattacc atggtgatgc ggttttggca gtacatcaat | 1800 |
| gggcgtggat agcggtttga ctcacgggga tttccaagtc tccacccat tgacgtcaat | 1860 |
| gggagtttgt tttggcacca aaatcaacgg gactttccaa aatgtcgtaa caactccgcc | 1920 |
| ccattgacgg ctagcagaac aggatgttct gatcaaagag atccaaagtc agaacacgtt | 1980 |
| gttctagcta aaataacaca ttcagagaac atgctgttct gatcaaagag atccaaagtc | 2040 |
| agaacaaggt gttctagcta aaataacaca ttcagagaac atgatgttct gatcaaagag | 2100 |
| atccaaagtc ctcgaggata tcaagatctg caaatgggcg gtaggcgtgt acggtgggag | 2160 |
| gtctatataa gcagagctct ctggctaact agagaaccca ctgcttactg gcttatcga | 2219 |

<210> SEQ ID NO 14
<211> LENGTH: 5427
<212> TYPE: DNA
<213> ORGANISM: Artificial Sequence
<220> FEATURE:
<223> OTHER INFORMATION: pcDNA 3.1 vector (-)

<400> SEQUENCE: 14

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattcc | 960 |
| accacactgg actagtggat ccgagctcgg taccaagctt aagtttaaac cgctgatcag | 1020 |
| cctcgactgt gccttctagt tgccagccat ctgttgtttg cccctccccc gtgccttcct | 1080 |
| tgaccctgga aggtgccact cccactgtcc tttcctaata aaatgaggaa attgcatcgc | 1140 |
| attgtctgag taggtgtcat tctattctgg ggggtgggt ggggcaggac agcaaggggg | 1200 |
| aggattggga agacaatagc aggcatgctg gggatgcggt gggctctatg gcttctgagg | 1260 |
| cggaaagaac cagctggggc tctaggggt atccccacgc gccctgtagc ggcgcattaa | 1320 |
| gcgcggcggg tgtggtggtt acgcgcagcg tgaccgctac acttgccagc gccctagcgc | 1380 |
| ccgctccttt cgctttcttc ccttcctttc tcgccacgtt cgccggcttt ccccgtcaag | 1440 |

```
ctctaaatcg ggggctccct ttagggttcc gatttagtgc tttacggcac ctcgacccca   1500
aaaaacttga ttagggtgat ggttcacgta gtgggccatc gccctgatag acggtttttc   1560 gcccttgac gttggagtcc acgttcttta atagtggact cttgttccaa actggaacaa    1620
cactcaaccc tatctcggtc tattcttttg atttataagg gattttgccg atttcggcct   1680
attggttaaa aaatgagctg atttaacaaa aatttaacgc gaattaattc tgtggaatgt   1740
gtgtcagtta gggtgtggaa agtccccagg ctccccagca ggcagaagta tgcaaagcat   1800
gcatctcaat tagtcagcaa ccaggtgtgg aaagtcccca ggctcccag caggcagaag    1860 tatgcaaagc atgcatctca attagtcagc aaccatagtc ccgcccctaa ctccgcccat   1920 cccgcccta actccgccca gttccgccca ttctccgccc catggctgac taatttttt     1980 tatttatgca gaggccgagg ccgcctctgc ctctgagcta ttccagaagt agtgaggagg   2040
cttttttgga ggcctaggct tttgcaaaaa gctcccggga gcttgtatat ccattttcgg   2100
atctgatcaa gagacaggat gaggatcgtt tcgcatgatt gaacaagatg gattgcacgc   2160
aggttctccg gccgcttggg tggagaggct attcggctat gactgggcac aacagacaat   2220
cggctgctct gatgccgccg tgttccggct gtcagcgcag gggcgcccgg ttcttttttgt  2280 caagaccgac ctgtccggtg ccctgaatga actgcaggac gaggcagcgc ggctatcgtg   2340
gctggccacg acgggcgttc cttgcgcagc tgtgctcgac gttgtcactg aagcgggaag   2400
ggactggctg ctattgggcg aagtgccggg gcaggatctc ctgtcatctc accttgctcc   2460
tgccgagaaa gtatccatca tggctgatgc aatgcggcgg ctgcatacgc ttgatccggc   2520
tacctgccca ttcgaccacc aagcgaaaca tcgcatcgag cgagcacgta ctcggatgga   2580
agccggtctt gtcgatcagg atgatctgga cgaagagcat caggggctcg cgccagccga   2640
actgttcgcc aggctcaagg cgcgcatgcc cgacggcgag gatctcgtcg tgacccatgg   2700
cgatgcctgc ttgccgaata tcatggtgga aaatggccgc ttttctggat tcatcgactg   2760
tggccggctg ggtgtggcgg accgctatca ggacatagcg ttggctaccc gtgatattgc   2820
tgaagagctt ggcggcgaat gggctgaccg cttcctcgtg ctttacggta tcgccgctcc   2880
cgattcgcag cgcatcgcct tctatcgcct tcttgacgag ttcttctgag cgggactctg   2940
gggttcgaaa tgaccgacca agcgacgccc aacctgccat cacgagattt cgattccacc   3000
gccgccttct atgaaaggtt gggcttcgga atcgttttcc gggacgccgg ctggatgatc   3060
ctccagcgcg gggatctcat gctggagttc ttcgcccacc ccaacttgtt tattgcagct   3120
tataatggtt acaaataaag caatagcatc acaaatttca caaataaagc atttttttca   3180
ctgcattcta gttgtggttt gtccaaactc atcaatgtat cttatcatgt ctgtataccg   3240
tcgacctcta gctagagctt ggcgtaatca tggtcatagc tgtttcctgt gtgaaattgt   3300
tatccgctca caattccaca acatacga gccggaagca taaagtgtaa agcctggggt     3360
gcctaatgag tgagctaact cacattaatt gcgttgcgct cactgcccgc tttccagtcg   3420
ggaaacctgt cgtgccagct gcattaatga atcggccaac gcgcggggag aggcggtttg   3480
cgtattgggc gctcttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgttttttcca taggctccgc cccccctgacg agcatcacaa aaatcgacgc  3720
tcaagtcaga ggtggcgaaa cccgacagga ctataaagat accaggcgtt ccccctggaa   3780
agctccctcg tgcgctctcc tgttccgacc ctgccgctta ccggatacct gtccgccttt   3840
```

```
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttccttcgg aaaaagagtt ggtagctctt gatccggcaa acaaaccacc      4200
gctggtagcg gttttttgt ttgcaagcag cagattacgc gcagaaaaaa aggatctcaa      4260
gaagatcctt tgatctttc tacggggtct gacgctcagt ggaacgaaaa ctcacgttaa      4320
gggattttgg tcatgagatt atcaaaaagg atcttcacct agatcctttt aaattaaaaa     4380
tgaagtttta aatcaatcta agtatatat gagtaaactt ggtctgacag ttaccaatgc      4440
ttaatcagtg aggcacctat ctcagcgatc tgtctatttc gttcatccat agttgcctga     4500
ctccccgtcg tgtagataac tacgatacgg gagggcttac catctggccc cagtgctgca    4560
atgataccgc gagacccacg ctcaccggct ccagatttat cagcaataaa ccagccagcc    4620
ggaagggccg agcgcagaag tggtcctgca actttatccg cctccatcca gtctattaat    4680
tgttgccggg aagctagagt aagtagttcg ccagttaata gtttgcgcaa cgttgttgcc    4740
attgctacag gcatcgtggt gtcacgctcg tcgtttggta tggcttcatt cagctccggt    4800
tcccaacgat caaggcgagt tacatgatcc cccatgttgt gcaaaaaagc ggttagctcc    4860
ttcggtcctc cgatcgttgt cagaagtaag ttggccgcag tgttatcact catggttatg    4920
gcagcactgc ataattctct tactgtcatg ccatccgtaa gatgcttttc tgtgactggt    4980
gagtactcaa ccaagtcatt ctgagaatag tgtatgcggc gaccgagttg ctcttgcccg    5040
gcgtcaatac gggataatac cgcgccacat agcagaactt taaaagtgct catcattgga    5100
aaacgttctt cggggcgaaa actctcaagg atcttaccgc tgttgagatc cagttcgatg    5160
taacccactc gtgcacccaa ctgatcttca gcatctttta ctttcaccag cgtttctggg    5220
tgagcaaaaa caggaaggca aaatgccgca aaaaagggaa taagggcgac acggaaatgt    5280
tgaatactca tactcttcct ttttcaatat tattgaagca tttatcaggg ttattgtctc    5340
atgagcggat acatatttga atgtatttag aaaaataaac aaataggggt tccgcgcaca    5400
tttccccgaa aagtgccacc tgacgtc                                        5427
```

<210> SEQ ID NO 15
<211> LENGTH: 1413
<212> TYPE: DNA
<213> ORGANISM: Artificial Sequence
<220> FEATURE:
<223> OTHER INFORMATION: Ab1 antibody heavy chain

<400> SEQUENCE: 15

```
atgggatgga gtctgatatt gttattcctt gttgctgtcg caacgcgggt cctgagtcaa      60
gtgcagctgc aacaacctgg cgcagaactc gtgaagcccg gtgcttccgt taagatgagc     120
tgtaaggcgt ccggttatac cttcacatct acaacatgc attgggtgaa gcagacccc      180 ggacgaggcc tcgaatggat cggggccatt tacccaggga atggagatac tagctataat    240
cagaagttca agggaaggc caccttgaca gccgacaagt ctagcagcac cgcctatatg     300
cagctatcat cacttactag cgaagattcc gccgtctact actgtgctag gtccaccta     360 tacggcggag attggtattt taacgtgtgg ggcgcaggca ctacagtaac cgtgtctgca    420
```

```
gcctcaacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctggggggA      780
ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtt     1260
ctggactccg acggctcctt cttcctctac agcaagctca ccgtggacaa gagcaggtgg     1320
cagcagggga acgtcttctc atgctccgtg atgcatgagg ctctgcacaa ccactacaca     1380
cagaagagcc tctccctgtc tccgggtaaa tga                                  1413

<210> SEQ ID NO 16
<211> LENGTH: 708
<212> TYPE: DNA
<213> ORGANISM: Artificial Sequence
<220> FEATURE:
<223> OTHER INFORMATION: Ab1 antibody light chain

<400> SEQUENCE: 16
atggattttc aggtgcaaat catttccttc ctattgatca gtgcttcagt tattatgtca       60
aggggccaga tcgtgctctc tcagagcccc gctatcttaa gtgcatcccc tggcgaaaag      120
gtaacaatga cttgtcgagc ctcctcttcc gttagttata tccactggtt ccagcagaaa      180
cccggaagct cacctaagcc atggatatac gcgaccagca atcttgcaag cggggtgcct      240
gtcagattca gcggcagcgg aagcggtacc tcttattctc tcaccatctc ccgggtcgaa      300
gccgaggacg cagccacgta ctactgccag cagtggacat ccaatccacc cactttcggt      360
ggggaaccaa agctggaaat caaacggact gttgcggcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcccctg      600 acgctgagca agcagactac cgagaaacac aaagtctacg cctgcgaagt cacccatcag      660
ggcctgagct cgcccgtcac aaagagcttc aacaggggag agtgttga                 708

<210> SEQ ID NO 17
<211> LENGTH: 588
<212> TYPE: DNA
<213> ORGANISM: Artificial Sequence
<220> FEATURE:
<223> OTHER INFORMATION: IRES

<400> SEQUENCE: 17
gccgcccctc tccctccccc cccccctaacg ttactggccg aagccgcttg gaataaggcc      60
```

```
ggtgtgcgtt tgtctatatg ttattttcca ccatattgcc gtcttttggc aatgtgaggg      120
cccggaaacc tggccctgtc ttcttgacga gcattcctag gggtctttcc cctctcgcca      180
aaggaatgca aggtctgttg aatgtcgtga aggaagcagt tcctctggaa gcttcttgaa      240
gacaaacaac gtctgtagcg acccttttgca ggcagcggaa ccccccacct ggcgacaggt     300
gcctctgcgg ccaaaagcca cgtgtataag atacacctgc aaaggcggca caaccccagt     360
gccacgttgt gagttggata gttgtggaaa gagtcaaatg gctctcctca agcgtattca      420
acaaggggct gaaggatgcc cagaaggtac cccattgtat gggatctgat ctggggcctc      480
ggtacacatg ctttacatgt gtttagtcga ggttaaaaaa acgtctaggc cccccgaacc      540
acggggacgt ggttttcctt tgaaaaacac gatgataata tggccaca                  588

<210> SEQ ID NO 18
<211> LENGTH: 2765
<212> TYPE: DNA
<213> ORGANISM: Artificial Sequence
<220> FEATURE:
<223> OTHER INFORMATION: CH-aCD20 - IRES - CL-aCD20

<400> SEQUENCE: 18
atgggatgga gtctgatatt gttattcctt gttgctgtcg caacgcgggt cctgagtcaa       60
gtgcagctgc aacaacctgg cgcagaactc gtgaagcccg gtgcttccgt taagatgagc      120
tgtaaggcgt ccggttatac cttcacatct acaacatgc attgggtgaa gcagacccccc      180 ggacgaggcc tcgaatggat cggggccatt tacccaggga atggagatac tagctataat      240
cagaagttca agggaaggc caccttgaca gccgacaagt ctagcagcac cgcctatatg       300
cagctatcat cacttactag cgaagattcc gccgtctact actgtgctag gtccaccctac     360 tacggcggag attggtattt taacgtgtgg ggcgcaggca ctacagtaac cgtgtctgca      420
gcctcaacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctgggggga      780
ccgtcagtct tcctcttccc cccaaaaccc aaggacaccc tcatgatctc ccggaccct      840 gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag gcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtt     1260
ctggactccg acggctcctt cttcctctac agcaagctca ccgtggacaa gagcaggtgg     1320
cagcagggga acgtcttctc atgctccgtg atgcatgagg ctctgcacaa ccactacaca     1380
cagaagagcc tctccctgtc tccgggtaaa tgaacgcgtg gttggatccc taccggtgct     1440
gcggccgcgc agttaacgcc gcccctctcc ctccccccccc cctaacgtta ctggccgaag     1500
```

```
ccgcttggaa taaggccggt gtgcgtttgt ctatatgtta ttttccacca tattgccgtc    1560
ttttggcaat gtgagggccc ggaaacctgg ccctgtcttc ttgacgagca ttcctagggg    1620
tctttcccct ctcgccaaag gaatgcaagg tctgttgaat gtcgtgaagg aagcagttcc    1680
tctggaagct tcttgaagac aaacaacgtc tgtagcgacc ctttgcaggc agcggaaccc    1740
cccacctggc gacaggtgcc tctgcggcca aaagccacgt gtataagata cacctgcaaa    1800
ggcggcacaa ccccagtgcc acgttgtgag ttggatagtt gtggaaagag tcaaatggct    1860
ctcctcaagc gtattcaaca aggggctgaa ggatgcccag aaggtacccc attgtatggg    1920
atctgatctg gggcctcggt acacatgctt tacatgtgtt tagtcgaggt taaaaaaacg    1980
tctaggcccc ccgaaccacg gggacgtggt tttcctttga aaaacacgat gataatatgg    2040
ccacacatat ggccaccatg gattttcagg tgcaaatcat ttccttccta ttgatcagtg    2100
cttcagttat tatgtcaagg ggccagatcg tgctctctca gagccccgct atcttaagtg    2160
catcccctgg cgaaaaggta acaatgactt gtcgagcctc ctcttccgtt agttatatcc    2220
actggttcca gcagaaaccc ggaagctcac ctaagccatg gatatacgcg accagcaatc    2280
ttgcaagcgg ggtgcctgtc agattcagcg gcagcggaag cggtacctct tattctctca    2340
ccatctcccg ggtcgaagcc gaggacgcag ccacgtacta ctgccagcag tggacatcca    2400
atccacccac tttcggtggg ggaaccaagc tggaaatcaa acggactgtt gcggcaccat    2460
ctgtcttcat cttcccgcca tctgatgagc agttgaaatc tggaactgcc tctgttgtgt    2520
gcctgctgaa taacttctat cccagagagg ccaaagtaca gtggaaggtg gataacgccc    2580
tccaatcggg taactcccag gagagtgtca cagagcagga cagcaaggac agcacctaca    2640
gcctcagcag cacccctgacg ctgagcaaag cagactacga gaaacacaaa gtctacgcct    2700
gcgaagtcac ccatcagggc ctgagctcgc ccgtcacaaa gagcttcaac aggggagagt    2760
gttga                                                                2765

<210> SEQ ID NO 19
<211> LENGTH: 7485
<212> TYPE: DNA
<213> ORGANISM: Artificial Sequence
<220> FEATURE:
<223> OTHER INFORMATION: Seq1-Ab1 vector

<400> SEQUENCE: 19
gttggttttt tgtgtgaatc gatagtacta acatacgctc tccatcaaaa caaaacgaaa      60
caaaacaaac tagcaaaata ggctgtcccc agtgcaagtg caggtgccag aacatttctc     120
tggcctaact ggccggtacc tgagctcgct agcctcgagg atatcaagat ctgttgacat     180
tgattattga ctagttatta atagtaatca attacgggt cattagttca tagcccatat     240
atggagttcc gcgttacata acttacggta aatggcccgc ctggctgacc gcccaacgac     300
ccccgcccat tgacgtcaat aatgacgtat gttcccatag taacgccaat agggactttc     360
cattgacgtc aatgggtgga gtatttacgg taaactgccc acttggcagt acatcaagtg     420
tatcatatgc caagtacgcc ccctattgac gtcaatgacg gtaaatggcc cgcctggcat     480
tatgcccagt acatgacctt atgggacttt cctacttggc agtacatcta cgtattagtc     540
atcgctatta ccatggtgat gcggttttgg cagtacatca atgggcgtgg atagcggttt     600
gactcacggg gatttccaag tctccacccc attgacgtca atgggagttt gttttggcac     660
caaaatcaac gggactttcc aaaatgtcgt aacaactccg ccccattgac gcaaatgggc     720
ggtaggcgtg tacggtggga ggtctatata agcagagctc tctggctaac tagagaaccc     780
```

```
actgcttact ggcttatcga aagcttcact atagggagac ccaagctggc tagccaccat      840
gggatggagt ctgatattgt tattccttgt tgctgtcgca acgcgggtcc tgagtcaagt      900
gcagctgcaa caacctggcg cagaactcgt gaagcccggt gcttccgtta agatgagctg      960
taaggcgtcc ggttatacct tcacatctta caacatgcat tgggtgaagc agaccccgg      1020 acgaggcctc gaatggatcg gggccattta cccagggaat ggagatacta gctataatca     1080
gaagttcaaa gggaaggcca ccttgacagc cgacaagtct agcagcaccg cctatatgca     1140
gctatcatca cttactagcg aagattccgc cgtctactac tgtgctaggt ccacctacta     1200
cggcggagat tggtatttta acgtgtgggg cgcaggcact acagtaaccg tgtctgcagc     1260
ctcaaccaag ggcccatcgg tcttcccccc tggcaccctcc tccaagagca cctctggggg    1320
cacagcggcc ctgggctgcc tggtcaagga ctacttcccc gaaccggtga cggtgtcgtg     1380
gaactcaggc gccctgacca gcggcgtgca caccttcccg gctgtcctac agtcctcagg    1440
actctactcc ctcagcagcg tggtgaccgt gccctccagc agcttgggca cccagaccta    1500
catctgcaac gtgaatcaca agcccagcaa caccaaggtg gacaagaaag ttgagcccaa    1560
atcttgtgac aaaactcaca catgcccacc gtgcccagca cctgaactcc tggggggacc    1620
gtcagtcttc ctcttccccc caaaacccaa ggacaccctc atgatctccc ggacccctga    1680
ggtcacatgc gtggtggtgg acgtgagcca cgaagaccct gaggtcaagt tcaactggta    1740
cgtggacggc gtggaggtgc ataatgccaa gacaaagccg cgggaggagc agtacaacag    1800
cacgtaccgt gtggtcagcg tcctcaccgt cctgcaccag gactggctga atggcaagga    1860
gtacaagtgc aaggtctcca acaaagccct cccagccccc atcgagaaaa ccatctccaa    1920
agccaaaggg cagccccgag aaccacaggt gtacaccctg cccccatccc gggatgagct    1980
gaccaagaac caggtcagcc tgacctgcct ggtcaaaggc ttctatccca gcgacatcgc    2040
cgtggagtgg gagagcaatg ggcagccgga gaacaactac aagaccacgc ctcccgttct    2100
ggactccgac ggctccttct tcctctacag caagctcacc gtggacaaga gcaggtggca    2160
gcaggggaac gtcttctcat gctccgtgat gcatgaggct ctgcacaacc actacacaca    2220
gaagagcctc tccctgtctc cgggtaaatg aacgcgtggt tggatcccta ccggtgctgc    2280
ggccgcgcag ttaacgccgc ccctctccct cccccccccc taacgttact ggccgaagcc    2340
gcttggaata aggccggtgt gcgtttgtct atatgttatt ttccaccata ttgccgtctt    2400
ttggcaatgt gagggcccgg aaacctggcc ctgtcttctt gacgagcatt cctaggggtc    2460
tttcccctct cgccaaagga atgcaaggtc tgttgaatgt cgtgaaggaa gcagttcctc    2520
tggaagcttc ttgaagacaa acaacgtctg tagcgaccct ttgcaggcag cggaaccccc    2580
cacctggcga caggtgcctc tgcggccaaa agccacgtgt ataagataca cctgcaaagg    2640
cggcacaacc ccagtgccac gttgtgagtt ggatagttgt ggaaagagtc aaatggctct    2700
cctcaagcgt attcaacaag ggctgaagg atgcccagaa ggtacccat tgtatgggat    2760 ctgatctggg gcctcggtac acatgcttta catgtgttta gtcgaggtta aaaaaacgtc    2820 taggccccccc gaaccacggg gacgtggttt cctttgaaa acacgatgga taatatggcc    2880
acacatatgg ccaccatgga ttttcaggtg caaatcattt ccttcctatt gatcagtgct    2940
tcagttatta tgtcaagggg ccagatcgtg ctctctcaga gccccgctat cttaagtgca    3000
tcccctggcg aaaaggtaac aatgacttgt cgagcctcct cttccgttag ttatatccac    3060
tggttccagc agaaacccgg aagctcacct aagccatgga tatacgcgac cagcaatctt    3120
```

```
gcaagcgggg tgcctgtcag attcagcggc agcggaagcg gtacctctta ttctctcacc    3180
atctcccggg tcgaagccga ggacgcagcc acgtactact gccagcagtg gacatccaat    3240
ccacccactt tcggtggggg aaccaagctg gaaatcaaac ggactgttgc ggcaccatct    3300
gtcttcatct tcccgccatc tgatgagcag ttgaaatctg gaactgcctc tgttgtgtgc    3360
ctgctgaata acttctatcc cagagaggcc aaagtacagt ggaaggtgga taacgccctc    3420
caatcgggta actcccagga gagtgtcaca gagcaggaca gcaaggacag cacctacagc    3480
ctcagcagca ccctgacgct gagcaaagca gactacgaga acacaaagt ctacgcctgc    3540 gaagtcaccc atcagggcct gagctcgccc gtcacaaaga gcttcaacag gggagagtgt    3600
tgaggatcca ctagtccagt gtggtggaat tcgtgtaata attctagagt cggggcggcc    3660
ggccgcttcg agcagacatg ataagataca ttgatgagtt tggacaaacc acaactagaa    3720
tgcagtgaaa aaaatgcttt atttgtgaaa tttgtgatgc tattgcttta tttgtaacca    3780
ttataagctg caataaacaa gttaacaaca acaattgcat tcattttatg tttcaggttc    3840
agggggaggt gtgggaggtt ttttaaagca agtaaaacct ctacaaatgt ggtaaaatcg    3900
ataaggatcc gtttgcgtat gggcgctct tccgctgatc tgcgcagcac catggcctga    3960
aataacctct gaaagaggaa cttggttagc taccttctga ggcggaaaga accagctgtg    4020
gaatgtgtgt cagttagggt gtggaaagtc cccaggctcc ccagcaggca gaagtatgca    4080
aagcatgcat ctcaattagt cagcaaccag gtgtggaaag tccccaggct ccccagcagg    4140
cagaagtatg caaagcatgc atctcaatta gtcagcaacc atagtcccgc ccctaactcc    4200
gcccatcccg cccctaactc cgcccagttc cgcccattct ccgccccatg ctgactaat    4260 tttttttatt tatgcagagg ccgaggccgc ctctgcctct gagctattcc agaagtagtg    4320
aggaggcttt tttggaggcc taggcttttg caaaaagctc gattcttctg cactagcgc    4380 caccatgatc gaacaagacg gcctccatgc tggcagtccc gcagcttggg tcgaacgctt    4440
gttcgggtac gactgggccc agcagaccat cggatgtagc gatgcggccg tgttccgtct    4500
aagcgctcaa ggccggcccg tgctgttcgt gaagaccgac ctgagcggcg ccctgaacga    4560
gcttcaagac gaggctgccc gcctgagctg gctggccacc accggcgtac cctgcgccgc    4620
tgtgttggat gttgtgaccg aagccggccg ggactggctg ctgctgggcg aggtccctgg    4680
ccaggatctg ctgagcagcc accttgcccc cgctgagaag gttctatca tggccgatgc    4740 aatgcggcgc ctgcacaccc tggaccccgc tacctgcccc ttcgaccacc aggctaagca    4800
tcggatcgag cgtgctcgga cccgcatgga ggccggcctg gtggaccagg acgacctgga    4860
cgaggagcat cagggcctgg cccccgctga actgttcgcc cgactgaaag cccgcatgcc    4920
ggacggtgag gacctggttg tcacacacgg agatgcctgc ctccctaaca tcatggtcga    4980
gaatggccgc ttctccggct tcatcgactg cggtcgccta ggagttgccg accgctacca    5040
ggacatcgcc ctggccaccc gcgacatcgc tgaggagctt ggcggcgagt gggccgaccg    5100
cttcttagtc ttgtacggca tcgcagctcc cgacagccag cgcatcgcct tctaccgctt    5160
gctcgacgag ttcttttaat gatctagaac cggtcatggc cgcaataaaa tatctttatt    5220
ttcattacat ctgtgtgttg gttttttgtg tgttcgaact agatgctgtc gaccgatgcc    5280
cttgagagcc ttcaacccag tcagctcctt ccggtgggcg cggggcatga ctatcgtcgc    5340
cgcacttatg actgtcttct ttatcatgca actcgtagga caggtgccgg cagcgctctt    5400
ccgcttcctc gctcactgac tcgctgcgct cggtcgttcg gctgcggcga gcggtatcag    5460
ctcactcaaa ggcggtaata cggttatcca cagaatcagg ggataacgca ggaaagaaca    5520
```
tgtgagcaaa aggccagcaa aaggccagga accgtaaaaa ggccgcgttg ctggcgtttt    5580
tccataggct ccgcccccct gacgagcatc acaaaaatcg acgctcaagt cagaggtggc    5640
gaaacccgac aggactataa agataccagg cgtttccccc tggaagctcc ctcgtgcgct    5700
ctcctgttcc gaccctgccg cttaccggat acctgtccgc ctttctccct tcgggaagcg    5760
tggcgctttc tcatagctca cgctgtaggt atctcagttc ggtgtaggtc gttcgctcca    5820
agctgggctg tgtgcacgaa ccccccgttc agcccgaccg ctgcgcctta tccggtaact    5880
atcgtcttga gtccaacccg gtaagacacg acttatcgcc actggcagca gccactggta    5940
acaggattag cagagcgagg tatgtaggcg gtgctacaga gttcttgaag tggtggccta    6000
actacggcta cactagaaga acagtatttg gtatctgcgc tctgctgaag ccagttacct    6060
tcggaaaaag agttggtagc tcttgatccg gcaaacaaac caccgctggt agcggtggtt    6120
tttttgtttg caagcagcag attacgcgca gaaaaaaagg atctcaagaa gatcctttga    6180
tcttttctac ggggtctgac gctcagtgga acgaaaactc acgttaaggg attttggtca    6240
tgagattatc aaaaaggatc ttcacctaga tccttttaaa ttaaaaatga agttttaaat    6300
caatctaaag tatatatgag taaacttggt ctgacagcgg ccgcaaatgc taaaccactg    6360
cagtggttac cagtgcttga tcagtgaggc accgatctca gcgatctgcc tatttcgttc    6420
gtccatagtg gcctgactcc ccgtcgtgta gatcactacg attcgtgagg gcttaccatc    6480
aggccccagc gcagcaatga tgccgcgaga gccgcgttca ccggcccccg atttgtcagc    6540
aatgaaccag ccagcaggga gggccgagcg aagaagtggt cctgctactt tgtccgcctc    6600
catccagtct atgagctgct gtcgtgatgc tagagtaaga agttcgccag tgagtagttt    6660
ccgaagagtt gtggccattg ctactggcat cgtggtatca cgctcgtcgt tcggtatggc    6720
ttcgttcaac tctggttccc agcggtcaag ccgggtcaca tgatcaccca tattatgaag    6780
aaatgcagtc agctccttag ggcctccgat cgttgtcaga agtaagttgg ccgcggtgtt    6840
gtcgctcatg gtaatggcag cactacacaa ttctcttacc gtcatgccat ccgtaagatg    6900
cttttccgtg accggcgagt actcaaccaa gtcgttttgt gagtagtgta tacggcgacc    6960
aagctgctct tgcccggcgt ctatacggga caacaccgcg ccacatagca gtactttgaa    7020
agtgctcatc atcgggaatc gttcttcggg gcggaaagac tcaaggatct tgccgctatt    7080
gagatccagt tcgatatagc ccactcttgc acccagttga tcttcagcat cttttacttt    7140
caccagcgtt tcggggtgtg caaaaacagg caagcaaaat gccgcaaaga agggaatgag    7200
tgcgacacga aaatgttgga tgctcatact cgtccttttt caatattatt gaagcattta    7260
tcagggttac tagtacgtct ctcaaggata agtaagtaat attaaggtac gggaggtatt    7320
ggacaggccg caataaaata tctttatttt cattacatct gtgtgttggt tttttgtgtg    7380
aatcgatagt actaacatac gctctccatc aaaacaaaac gaaacaaaac aaactagcaa    7440 ataggctgt ccccagtgca agtgcaggtg ccagaacatt tctct    7485

<210> SEQ ID NO 20
<211> LENGTH: 8647
<212> TYPE: DNA
<213> ORGANISM: Artificial Sequence
<220> FEATURE:
<223> OTHER INFORMATION: Seq2-Ab1 vector
<400> SEQUENCE: 20
gttggttttt tgtgtgaatc gatagtacta acatacgctc tccatcaaaa caaaacgaaa    60

-continued

```
caaaacaaac tagcaaaata ggctgtcccc agtgcaagtg caggtgccag aacatttctc     120
tggcctaact ggccggtacc ggagaggggg taaaaaaatg ctgcactgtg cggctaggcc     180
ggtgagtgag cggcgcggag ccaatcagcg ctcgccgttc cgaaagttgc cttttatggc     240
tcgagtggcc gctgtggcgt cctataaaac ccggcggcgc aacgcgcagc cactgtcgag     300
tccgcgtcca cccgcgagca caggcctttc gcagctcttt cttcgccgct ccacacccgc     360
caccaggtaa gcagggacaa caggcccagc cggccacagc cctcccgtgg gcagtgaccg     420
cgctgcaggg tcgcggggga cactcggcgc ggacaccggg gaaggctgga gggtggtgcc     480
gggccgcgga gcggacactt tcagatccaa ctttcagtcc agggtgtaga ccctttacag     540
ccgcattgcc acggtgtaga caccggtgga cccgctctgg ctcagagcac gcggcttggg     600
ggaacccatt agggtcgcag tgtgggcgct atgagagccg atgcagcttt cggtgttga     660 accgtatctg cccaccttgg ggggaggaca caaggtcggg agccaaacgc cacgatcatg     720
ccttggtggc ccatgggtct ttgtctaaac cggtttgccc atttggcttg ccgggcgggc     780
gggcgcggcg ggcccggctc ggccgggttg ggggctgggt tgccactgcg cttgcgcgct     840
ctatggctgg gtattgggc gcgtgcacgc tggggaggga gccttcctc ttcccctct      900 cccaagttaa acttgcgcgt gcgtattgag acttggagcg cggccaccgg ggttgggcga     960
gggcggggcc gttgtccgga aggggcgggg tcgcagcggc ttcggggcgc ctgctcgcgc    1020
ttcctgctgg gtgtggtcgc ctcccgcgcg cgcactagcc gcccgccggc ggggcgaagg    1080
cggggcttgc gcccgtttgg ggaggggcg gaggcctggc ttcctgccgt ggggccgcct     1140
ccggaccagc gtttgcctct tatggtaata acgcggccgg cctgggcttc ctttgtcccc    1200
tgagtttggg cgcgcgcccc ctggcggccc gaggccgcgg cttgccggaa gtgggcaggg    1260
cggcagcggc tgcgcctagt ggcccgccag tgaccgcgac cctcttttgt gccctgatat    1320
agttcgccag atctgttgac attgattatt gactagttat taatagtaat caattacggg    1380
gtcattagtt catagcccat atatggagtt ccgcgttaca aacttacgg taaatgccc      1440 gcctggctga ccgcccaacg accccgccc attgacgtca ataatgacgt atgttcccat     1500
agtaacgcca atagggactt tccattgacg tcaatgggtg gagtatttac ggtaaactgc    1560
ccacttggca gtacatcaag tgtatcatat gccaagtacg ccccctattg acgtcaatga    1620
cggtaaatgg cccgcctggc attatgccca gtacatgacc ttatgggact ttcctacttg    1680
gcagtacatc tacgtattag tcatcgctat taccatggtg atgcggtttt ggcagtacat    1740
caatgggcgt ggatagcggt ttgactcacg gggatttcca gtctccacc ccattgacgt     1800 caatgggagt ttgttttggc accaaaatca acgggacttt ccaaaatgtc gtaacaactc    1860
cgccccattg acgcaaatgg gcggtaggcg tgtacggtgg gaggtctata taagcagagc    1920
tctctggcta actagagaac ccactgctta ctggcttatc gaaagcttca ctatagggag    1980
acccaagctg gctagccacc atgggatgga gtctgatatt gttattcctt gttgctgtcg    2040
caacgcgggt cctgagtcaa gtgcagctgc aacaacctgg cgcagaactc gtgaagcccg    2100
gtgcttccgt taagatgagc tgtaaggcgt ccggttatac cttcacatct acaacatgc     2160 attgggtgaa gcagacccc ggacgaggcc tcgaatggat cggggccatt tacccaggga    2220
atggagatac tagctataat cagaagttca aagggaaggc caccttgaca gccgacaagt    2280
ctagcagcac cgcctatatg cagctatcat cacttactag cgaagattcc gccgtctact    2340
actgtgctag gtccacctac tacggcgag attggtattt taacgtgtgg ggcgcaggca    2400
ctacagtaac cgtgtctgca gcctcaacca agggcccatc ggtcttcccc ctggcaccct    2460
```

```
cctccaagag cacctctggg ggcacagcgg ccctgggctg cctggtcaag gactacttcc    2520
ccgaaccggt gacggtgtcg tggaactcag gcgccctgac cagcggcgtg cacaccttcc    2580
cggctgtcct acagtcctca ggactctact ccctcagcag cgtggtgacc gtgccctcca    2640
gcagcttggg cacccagacc tacatctgca acgtgaatca caagcccagc aacaccaagg    2700
tggacaagaa agttgagccc aaatcttgtg acaaaactca cacatgccca ccgtgcccag    2760
cacctgaact cctgggggga ccgtcagtct tcctcttccc cccaaaaccc aaggacaccc    2820
tcatgatctc ccggacccct gaggtcacat gcgtggtggt ggacgtgagc cacgaagacc    2880
ctgaggtcaa gttcaactgg tacgtggacg gcgtggaggt gcataatgcc aagacaaagc    2940
cgcgggagga gcagtacaac agcacgtacc gtgtggtcag cgtcctcacc gtcctgcacc    3000
aggactggct gaatggcaag gagtacaagt gcaaggtctc caacaaagcc ctcccagccc    3060
ccatcgagaa aaccatctcc aaagccaaag gcagccccg agaaccacag gtgtacaccc    3120
tgcccccatc ccgggatgag ctgaccaaga accaggtcag cctgacctgc ctggtcaaag    3180
gcttctatcc cagcgacatc gccgtggagt gggagagcaa tgggcagccg gagaacaact    3240
acaagaccac gcctcccgtt ctggactccg acggctcctt cttcctctac agcaagctca    3300
ccgtggacaa gagcaggtgg cagcagggga acgtcttctc atgctccgtg atgcatgagg    3360
ctctgcacaa ccactacaca cagaagagcc tctccctgtc tccgggtaaa tgaacgcgtg    3420
gttggatccc taccggtgct gcggccgcgc agttaacgcc gccctctcc ctcccccccc    3480 cctaacgtta ctggccgaag ccgcttggaa taaggccggt gtgcgtttgt ctatatgtta    3540
ttttccacca tattgccgtc ttttggcaat gtgagggccc ggaaacctgg ccctgtcttc    3600
ttgacgagca ttcctagggg tctttcccct ctcgccaaag gaatgcaagg tctgttgaat    3660
gtcgtgaagg aagcagttcc tctggaagct tcttgaagac aaacaacgtc tgtagcgacc    3720
ctttgcaggc agcggaaccc cccacctggc gacaggtgcc tctgcggcca aaagccacgt    3780
gtataagata cacctgcaaa ggcggcacaa ccccagtgcc acgttgtgag ttggatagtt    3840
gtggaaagag tcaaatggct ctcctcaagc gtattcaaca aggggctgaa ggatgcccag    3900
aaggtacccc attgtatggg atctgatctg gggcctcggt acacatgctt tacatgtgtt    3960
tagtcgaggt taaaaaaacg tctaggcccc ccgaaccacg gggacgtggt tttcctttga    4020
aaaacacgat gataatatgg ccacacatat ggccaccatg gattttcagg tgcaaatcat    4080
ttccttccta ttgatcagtg cttcagttat tatgtcaagg ggccagatcg tgctctctca    4140 gagcccgct atcttaagtg catccctgg cgaaaaggta acaatgactt gtcgagcctc    4200
ctcttccgtt agttatatcc actggttcca gcagaaaccc ggaagctcac ctaagccatg    4260
gatatacgcg accagcaatc ttgcaagcgg ggtgcctgtc agattcagcg gcagcggaag    4320
cggtacctct tattctctca ccatctcccg ggtcgaagcc gaggacgcag ccacgtacta    4380
ctgccagcag tggacatcca atccacccac tttcggtggg ggaaccaagc tggaaatcaa    4440
acggactgtt gcggcaccat ctgtcttcat cttcccgcca tctgatgagc agttgaaatc    4500
tggaactgcc tctgttgtgt gcctgctgaa taacttctat cccagagagg ccaaagtaca    4560
gtggaaggtg gataacgccc tccaatcggg taactcccag gagagtgtca cagagcagga    4620
cagcaaggac agcacctaca gcctcagcag caccctgacg ctgagcaaag cagactacga    4680
gaaacacaaa gtctacgcct gcgaagtcac ccatcagggc ctgagctcgc ccgtcacaaa    4740
gagcttcaac aggggagagt gttgaggatc cactagtcca gtgtggtgga attcgtgtaa    4800
```

```
taattctaga gtcggggcgg ccggccgctt cgagcagaca tgataagata cattgatgag    4860
tttggacaaa ccacaactag aatgcagtga aaaaaatgct ttatttgtga aatttgtgat    4920
gctattgctt tatttgtaac cattataagc tgcaataaac aagttaacaa caacaattgc    4980
attcatttta tgtttcaggt tcaggggag gtgtgggagg ttttttaaag caagtaaaac    5040
ctctacaaat gtggtaaaat cgataaggat ccgtttgcgt attgggcgct cttccgctga    5100
tctgcgcagc accatggcct gaaataacct ctgaaagagg aacttggtta gctaccttct    5160
gaggcggaaa gaaccagctg tggaatgtgt gtcagttagg gtgtggaaag tccccaggct    5220
ccccagcagg cagaagtatg caaagcatgc atctcaatta gtcagcaacc aggtgtggaa    5280
agtccccagg ctccccagca ggcagaagta tgcaaagcat gcatctcaat tagtcagcaa    5340
ccatagtccc gcccctaact ccgcccatcc cgccctaac tccgcccagt ccgcccatt    5400 ctccgcccca tggctgacta atttttttta tttatgcaga ggccgaggcc gcctctgcct    5460
ctgagctatt ccagaagtag tgaggaggct ttttggagg cctaggcttt tgcaaaaagc    5520
tcgattcttc tgacactagc gccaccatga tcgaacaaga cggcctccat gctggcagtc    5580
ccgcagcttg ggtcgaacgc ttgttcgggt acgactgggc ccagcagacc atcggatgta    5640
gcgatgcggc cgtgttccgt ctaagcgctc aaggccggcc cgtgctgttc gtgaagaccg    5700
acctgagcgg cgccctgaac gagcttcaag acgaggctgc cgcctgagc tggctggcca    5760 ccaccggcgt accctgcgcc gctgtgttgg atgttgtgac cgaagccggc cgggactggc    5820
tgctgctggg cgaggtccct ggccaggatc tgctgagcag ccaccttgcc cccgctgaga    5880
aggtttctat catggccgat gcaatgcggc gcctgcacac cctggacccc gctacctgcc    5940
ccttcgacca ccaggctaag catcggatcg agcgtgctcg gacccgcatg gaggccggcc    6000
tggtggacca ggacgacctg gacgaggagc atcagggcct ggcccccgct gaactgttcg    6060
cccgactgaa agcccgcatg ccggacggtg aggacctggt tgtcacacac ggagatgcct    6120
gcctccctaa catcatggtc gagaatggcc gcttctccgg cttcatcgac tgcggtcgcc    6180
taggagttgc cgaccgctac caggacatcg ccctggccac ccgcgacatc gctgaggagc    6240
ttggcggcga gtgggccgac cgcttcttag tcttgtacgg catcgcagct cccgacagcc    6300
agcgcatcgc cttctaccgc ttgctcgacg agttctttta atgatctaga accggtcatg    6360
gccgcaataa aatatcttta ttttcattac atctgtgtgt tggtttttg tgtgttcgaa    6420 ctagatgctg tcgaccgatg cccttgagag ccttcaaccc agtcagctcc ttccggtggg    6480
cgcggggcat gactatcgtc gccgcactta tgactgtctt ctttatcatg caactcgtag    6540
gacaggtgcc ggcagcgctc ttccgcttcc tcgctcactg actcgctgcg ctcggtcgtt    6600
cggctgcggc gagcggtatc agctcactca aaggcggtaa tacggttatc cacagaatca    6660
ggggataacg caggaaagaa catgtgagca aaaggccagc aaaaggccag gaaccgtaaa    6720
aaggccgcgt tgctggcgtt tttccatagg ctccgccccc ctgacgagca tcacaaaaat    6780
cgacgctcaa gtcagaggtg gcgaaacccg acaggactat aaagatacca ggcgtttccc    6840
cctggaagct ccctcgtgcg ctctcctgtt ccgaccctgc cgcttaccgg atacctgtcc    6900
gcctttctcc cttcgggaag cgtggcgctt tctcatagct cacgctgtag gtatctcagt    6960
tcggtgtagg tcgttcgctc caagctgggc tgtgtgcacg aaccccccgt tcagcccgac    7020
cgctgcgcct tatccggtaa ctatcgtctt gagtccaacc cggtaagaca cgacttatcg    7080
ccactggcag cagccactgg taacaggatt agcagagcga ggtatgtagg cggtgctaca    7140
gagttcttga agtggtggcc taactacggc tacactagaa gaacagtatt tggtatctgc    7200
```

-continued

```
gctctgctga agccagttac cttcggaaaa agagttggta gctcttgatc cggcaaacaa      7260
accaccgctg gtagcggtgg ttttttttgtt tgcaagcagc agattacgcg cagaaaaaaa      7320
ggatctcaag aagatccttt gatcttttct acggggtctg acgctcagtg gaacgaaaac      7380
tcacgttaag ggattttggt catgagatta tcaaaaagga tcttcaccta gatcctttta      7440
aattaaaaat gaagttttaa atcaatctaa agtatatatg agtaaacttg gtctgacagc      7500
ggccgcaaat gctaaaccac tgcagtggtt accagtgctt gatcagtgag gcaccgatct      7560
cagcgatctg cctatttcgt tcgtccatag tggcctgact ccccgtcgtg tagatcacta      7620
cgattcgtga gggcttacca tcaggcccca gcgcagcaat gatgccgcga gagccgcgtt      7680
caccggcccc cgatttgtca gcaatgaacc agccagcagg gagggccgag cgaagaagtg      7740
gtcctgctac tttgtccgcc tccatccagt ctatgagctg ctgtcgtgat gctagagtaa      7800
gaagttcgcc agtgagtagt ttccgaagag ttgtggccat tgctactggc atcgtggtat      7860
cacgctcgtc gttcggtatg gcttcgttca actctggttc ccagcggtca agccgggtca      7920
catgatcacc catattatga agaaatgcag tcagctcctt agggcctccg atcgttgtca      7980
gaagtaagtt ggccgcggtg ttgtcgctca tggtaatggc agcactacac aattctctta      8040
ccgtcatgcc atccgtaaga tgcttttccg tgaccggcga gtactcaacc aagtcgtttt      8100
gtgagtagtg tatacggcga ccaagctgct cttgcccggc gtctatacgg acaacaccg       8160
cgccacatag cagtactttg aaagtgctca tcatcgggaa tcgttcttcg ggcggaaag       8220
actcaaggat cttgccgcta ttgagatcca gttcgatata gcccactctt gcacccagtt      8280
gatcttcagc atcttttact ttcaccagcg tttcggggtg tgcaaaaaca ggcaagcaaa      8340
atgccgcaaa aagggaatg agtgcgacac gaaaatgttg gatgctcata ctcgtccttt      8400
ttcaatatta ttgaagcatt tatcagggtt actagtacgt ctctcaagga taagtaagta      8460
atattaaggt acgggaggta ttggacaggc cgcaataaaa tatctttatt ttcattacat      8520
ctgtgtgttg gttttttgtg tgaatcgata gtactaacat acgctctcca tcaaaacaaa      8580
acgaaacaaa acaaactagc aaaataggct gtccccagtg caagtgcagg tgccagaaca      8640
tttctct                                                                 8647
```

<210> SEQ ID NO 21
<211> LENGTH: 8836
<212> TYPE: DNA
<213> ORGANISM: Artificial Sequence
<220> FEATURE:
<223> OTHER INFORMATION: Seq3a-Ab1 vector

<400> SEQUENCE: 21

```
gttggttttt tgtgtgaatc gatagtacta acatacgctc tccatcaaaa caaaacgaaa       60
caaaacaaac tagcaaaata ggctgtcccc agtgcaagtg caggtgccag aacatttctc      120
tggcctaact ggccggtacc ggagaggggg taaaaaaatg ctgcactgtg cggctaggcc      180
ggtgagtgag cggcgcggag ccaatcagcg ctcgccgttc cgaaagttgc cttttatggc      240
tcgagtggcc gctgtggcgt cctataaaac ccggcggcgc aacgcgcagc cactgtcgag      300
tccgcgtcca cccgcgagca caggcctttc gcagctcttt cttcgccgct ccacacccgc      360
caccaggtaa gcagggacaa caggcccagc cggccacagc cctcccgtgg gcagtgaccg      420
cgctgcaggg tcgcggggga cactcggcgc ggacaccggg gaaggctgga gggtggtgcc      480
gggccgcgga gcggacactt tcagatccaa cttttcagtcc agggtgtaga cccttttacag     540
```

```
ccgcattgcc acggtgtaga caccggtgga cccgctctgg ctcagagcac gcggcttggg    600
ggaacccatt agggtcgcag tgtgggcgct atgagagccg atgcagcttt cgggtgttga    660
accgtatctg cccaccttgg ggggaggaca caaggtcggg agccaaacgc cacgatcatg    720
ccttggtggc ccatgggtct tgtctaaac cggtttgccc atttggcttg ccgggcgggc     780
gggcgcggcg ggcccggctc ggccgggttg ggggctgggt tgccactgcg cttgcgcgct    840
ctatggctgg gtattgggc gcgtgcacgc tggggaggga gcccttcctc ttccccctct     900
cccaagttaa acttgcgcgt gcgtattgag acttggagcg cggccaccgg ggttgggcga    960
gggcggggcc gttgtccgga aggggcgggg tcgcagcggc ttcggggcgc ctgctcgcgc    1020
ttcctgctgg gtgtggtcgc ctcccgcgcg cgcactagcc gcccgccggc ggggcgaagg    1080
cggggcttgc gcccgtttgg ggaggggcg gaggcctggc ttcctgccgt ggggccgcct     1140
ccggaccagc gtttgcctct tatggtaata acgcggccgg cctgggcttc ctttgtcccc    1200
tgagtttggg cgcgcgcccc ctggcggccc gaggccgcgg cttgccggaa gtgggcaggg    1260
cggcagcggc tgcgcctagt ggcccgccag tgaccgcgac cctcttttgt gccctgatat    1320
agttcgccga attcgctagc agaacaggat gttctgatca aagagatcca aagtcagaac    1380
acgttgttct agctaaaata acacattcag agaacatgct gttctgatca aagagatcca    1440
aagtcagaac aaggtgttct agctaaaata acacattcag agaacatgat gttctgatca    1500
aagagatcca aagtcgcggc cgcgttgaca ttgattattg actagttatt aatagtaatc    1560
aattacgggg tcattagttc atagcccata tatggagttc cgcgttacat aacttacggt    1620
aaatggcccg cctggctgac cgcccaacga ccccgccca ttgacgtcaa taatgacgta     1680
tgttcccata gtaacgccaa tagggacttt ccattgacgt caatgggtgg agtatttacg    1740
gtaaactgcc cacttggcag tacatcaagt gtatcatatg ccaagtacgc ccctattga     1800 cgtcaatgac ggtaaatggc ccgcctggca ttatgcccag tacatgacct tatgggactt    1860
tcctacttgg cagtacatct acgtattagt catcgctatt accatggtga tgcggttttg    1920
gcagtacatc aatgggcgtg gatagcggtt tgactcacgg ggatttccaa gtctccaccc    1980
cattgacgtc aatgggagtt tgttttggca ccaaaatcaa cgggactttc caaaatgtcg    2040
taacaactcc gccccattga cgcaaatggg cggtaggcgt gtacggtggg aggtctatat    2100
aagcagagct ctctggctaa ctagagaacc cactgcttac tggcttatcg aaagcttcac    2160
tatagggaga cccaagctgg ctagccacca tgggatggag tctgatattg ttattccttg    2220
ttgctgtcgc aacgcgggtc ctgagtcaag tgcagctgca acaacctggc gcagaactcg    2280
tgaagcccgg tgcttccgtt aagatgagct gtaaggcgtc cggttatacc ttcacatctt    2340
acaacatgca ttgggtgaag cagaccccg gacgaggcct cgaatggatc ggggccattt    2400
acccagggaa tggagatact agctataatc agaagttcaa agggaaggcc accttgacag    2460
ccgacaagtc tagcagcacc gcctatatgc agctatcatc acttactagc gaagattccg    2520
ccgtctacta ctgtgctagg tccacctact acggcggaga ttggtatttt aacgtgtggg    2580
gcgcaggcac tacagtaacc gtgtctgcag cctcaaccaa gggcccatcg gtcttccccc    2640
tggcaccctc ctccaagagc acctctgggg gcacagcggc cctgggctgc ctggtcaagg    2700
actacttccc cgaaccggtg acggtgtcgt ggaactcagg cgccctgacc agcggcgtgc    2760
acaccttccc ggctgtccta cagtcctcag gactctactc cctcagcagc gtggtgaccg    2820
tgccctccag cagcttgggc acccagacct acatctgcaa cgtgaatcac aagcccagca    2880
acaccaaggt ggacaagaaa gttgagccca atcttgtga caaaactcac acatgcccac     2940
```

```
cgtgcccagc acctgaactc ctgggggac  cgtcagtctt cctcttcccc ccaaaaccca  3000
aggacaccct catgatctcc cggacccctg aggtcacatg cgtggtggtg acgtgagcc   3060 acgaagaccc tgaggtcaag ttcaactggt acgtggacgg cgtggaggtg cataatgcca  3120
agacaaagcc gcgggaggag cagtacaaca gcacgtaccg tgtggtcagc gtcctcaccg  3180
tcctgcacca ggactggctg aatggcaagg agtacaagtg caaggtctcc aacaaagccc  3240
tcccagcccc catcgagaaa accatctcca aagccaaagg gcagcccga  gaaccacagg  3300 tgtacaccct gcccccatcc cgggatgagc tgaccaagaa ccaggtcagc ctgacctgcc  3360
tggtcaaagg cttctatccc agcgacatcg ccgtggagtg ggagagcaat gggcagccgg  3420
agaacaacta caagaccacg cctcccgttc tggactccga cggctccttc ttcctctaca  3480
gcaagctcac cgtggacaag agcaggtggc agcaggggaa cgtcttctca tgctccgtga  3540
tgcatgaggc tctgcacaac cactacacac agaagagcct ctccctgtct ccgggtaaat  3600
gaacgcgtgg ttggatccct accggtgctg cggccgcgca gttaacgccg ccctctccc   3660 tccccccccc ctaacgttac tggccgaagc cgcttggaat aaggccggtg tgcgtttgtc  3720
tatatgttat tttccaccat attgccgtct tttggcaatg tgagggcccg gaaacctggc  3780
cctgtcttct tgacgagcat tcctagggt cttcccctc tcgccaaagg aatgcaaggt    3840
ctgttgaatg tcgtgaagga agcagttcct ctggaagctt cttgaagaca acaacgtct   3900 gtagcgaccc tttgcaggca gcggaacccc ccacctggcg acaggtgcct ctgcggccaa  3960
aagccacgtg tataagatac acctgcaaag gcggcacaac cccagtgcca cgttgtgagt  4020
tggatagttg tggaaagagt caaatggctc tcctcaagcg tattcaacaa ggggctgaag  4080
gatgcccaga aggtacccca ttgtatggga tctgatctgg ggcctcggta cacatgcttt  4140
acatgtgttt agtcgaggtt aaaaaaacgt ctaggccccc cgaaccacgg ggacgtggtt  4200
ttcctttgaa aaacacgatg ataatatggc cacacatatg gccaccatgg atttcaggt   4260 gcaaatcatt tccttcctat tgatcagtgc ttcagttatt atgtcaaggg gccagatcgt  4320
gctctctcag agccccgcta tcttaagtgc atccctggc gaaaaggtaa caatgacttg   4380
tcgagcctcc tcttccgtta gttatatcca ctggttccag cagaaacccg gaagctcacc  4440
taagccatgg atatacgcga ccagcaatct tgcaagcggg gtgcctgtca gattcagcgg  4500
cagcggaagc ggtacctctt attctctcac catctcccgg gtcgaagccg aggacgcagc  4560
cacgtactac tgccagcagt ggacatccaa tccacccact ttcggtgggg gaaccaagct  4620
ggaaatcaaa cggactgttg cggcaccatc tgtcttcatc ttcccgccat ctgatgagca  4680
gttgaaatct ggaactgcct ctgttgtgtg cctgctgaat aacttctatc ccagagaggc  4740
caaagtacag tggaaggtgg ataacgcct  ccaatcgggt aactcccagg agagtgtcac  4800
agagcaggac agcaaggaca gcacctacag cctcagcagc accctgacgc tgagcaaagc  4860
agactacgag aaacacaaag tctacgcctg cgaagtcacc catcagggcc tgagctcgcc  4920
cgtcacaaag agcttcaaca ggggagagtg ttgaggatcc actagtccag tgtggtggaa  4980
ttcgtgtaat aattctagag tcggggcggc cggccgcttc gagcagacat gataagatac  5040
attgatgagt ttggacaaac cacaactaga atgcagtgaa aaaaatgctt tatttgtgaa  5100
atttgtgatg ctattgcttt atttgtaacc attataagct gcaataaaca agttaacaac  5160
aacaattgca ttcattttat gtttcaggtt caggggagg tgtgggaggt ttttaaagc    5220 aagtaaaacc tctacaaatg tggtaaaatc gataaggatc cgtttgcgta ttgggcgctc  5280
```

```
ttccgctgat ctgcgcagca ccatggcctg aaataacctc tgaaagagga acttggttag      5340
ctaccttctg aggcggaaag aaccagctgt ggaatgtgtg tcagttaggg tgtggaaagt      5400
ccccaggctc cccagcaggc agaagtatgc aaagcatgca tctcaattag tcagcaacca      5460
ggtgtggaaa gtccccaggc tccccagcag cagaagtat gcaaagcatg catctcaatt       5520
agtcagcaac catagtcccg cccctaactc cgcccatccc gcccctaact ccgcccagtt      5580
ccgcccattc tccgcccat ggctgactaa ttttttttat ttatgcagag gccgaggccg       5640
cctctgcctc tgagctattc cagaagtagt gaggaggctt ttttggaggc ctaggctttt      5700
gcaaaaagct cgattcttct gacactagcg ccaccatgat cgaacaagac ggcctccatg      5760
ctggcagtcc cgcagcttgg gtcgaacgct tgttcgggta cgactgggcc cagcagacca     5820
tcggatgtag cgatgcggcc gtgttccgtc taagcgctca aggccggccc gtgctgttcg      5880
tgaagaccga cctgagcggc gccctgaacg agcttcaaga cgaggctgcc cgcctgagct      5940
ggctggccac caccggcgta ccctgcgccg ctgtgttgga tgttgtgacc gaagccggcc     6000
gggactggct gctgctgggc gaggtccctg gccaggatct gctgagcagc caccttgccc     6060
ccgctgagaa ggtttctatc atggccgatg caatgcggcg cctgcacacc ctggaccccg     6120
ctacctgccc cttcgaccac caggctaagc atcggatcga gcgtgctcgg acccgcatgg     6180
aggccggcct ggtggaccag gacgacctgg acgaggagca tcagggcctg gcccccgctg     6240
aactgttcgc ccgactgaaa gcccgcatgc cggacggtga ggacctggtt gtcacacacg     6300
gagatgcctg cctccctaac atcatggtcg agaatggccg cttctccggc ttcatcgact     6360
gcggtcgcct aggagttgcc gaccgctacc aggacatcgc cctggccacc cgcgacatcg     6420
ctgaggagct tggcggcgag tgggccgacc gcttcttagt cttgtacggc atcgcagctc     6480
ccgacagcca gcgcatcgcc ttctaccgct tgctcgacga gttcttttaa tgatctagaa     6540
ccggtcatgg ccgcaataaa atatctttat tttcattaca tctgtgtgtt ggttttttgt     6600
gtgttcgaac tagatgctgt cgaccgatgc ccttgagagc cttcaaccca gtcagctcct     6660
tccggtgggc gcggggcatg actatcgtcg ccgcacttat gactgtcttc tttatcatgc     6720
aactcgtagg acaggtgccg gcagcgctct tccgcttcct cgctcactga ctcgctgcgc     6780
tcggtcgttc ggctgcggcg agcggtatca gctcactcaa aggcggtaat acggttatcc     6840
acagaatcag gggataacgc aggaaagaac atgtgagcaa aaggccagca aaaggccagg     6900
aaccgtaaaa aggccgcgtt gctggcgttt ttccataggc tccgcccccc tgacgagcat     6960
cacaaaaatc gacgctcaag tcagaggtgg cgaaacccga caggactata agataccag     7020 gcgtttcccc ctggaagctc cctcgtgcgc tctcctgttc cgaccctgcc gcttaccgga     7080
tacctgtccg cctttctccc ttcgggaagc gtggcgcttt ctcatagctc acgctgtagg     7140
tatctcagtt cggtgtaggt cgttcgctcc aagctgggct gtgtgcacga accccccgtt     7200
cagcccgacc gctgcgcctt atccggtaac tatcgtcttg agtccaaccc ggtaagacac     7260
gacttatcgc cactggcagc agccactggt aacaggatta gcagagcgag gtatgtaggc     7320
ggtgctacag agttcttgaa gtggtggcct aactacggct acactagaag aacagtattt     7380
ggtatctgcg ctctgctgaa gccagttacc ttcggaaaaa gagttggtag ctcttgatcc     7440
ggcaaacaaa ccaccgctgg tagcggtggt ttttttgttt gcaagcagca gattacgcgc     7500
agaaaaaaag gatctcaaga agatcctttg atcttttcta cggggtctga cgctcagtgg     7560
aacgaaaact cacgttaagg gattttggtc atgagattat caaaaaggat cttcacctag     7620
atccttttaa attaaaaatg aagttttaaa tcaatctaaa gtatatatga gtaaacttgg     7680
```

```
tctgacagcg gccgcaaatg ctaaaccact gcagtggtta ccagtgcttg atcagtgagg    7740
caccgatctc agcgatctgc ctatttcgtt cgtccatagt ggcctgactc cccgtcgtgt    7800
agatcactac gattcgtgag ggcttaccat caggccccag cgcagcaatg atgccgcgag    7860
agccgcgttc accggccccc gatttgtcag caatgaacca gccagcaggg agggccgagc    7920
gaagaagtgg tcctgctact ttgtccgcct ccatccagtc tatgagctgc tgtcgtgatg    7980
ctagagtaag aagttcgcca gtgagtagtt tccgaagagt gtggccatt  gctactggca    8040 tcgtggtatc acgctcgtcg ttcggtatgg cttcgttcaa ctctggttcc cagcggtcaa    8100
gccgggtcac atgatcaccc atattatgaa gaaatgcagt cagctcctta ggcctccga    8160 tcgttgtcag aagtaagttg gccgcggtgt tgtcgctcat ggtaatggca gcactacaca    8220
attctcttac cgtcatgcca tccgtaagat gcttttccgt gaccggcgag tactcaacca    8280
agtcgttttg tgagtagtgt atacggcgac caagctgctc ttgcccggcg tctatacggg    8340
acaacaccgc gccacatagc agtactttga aagtgctcat catcgggaat cgttcttcgg    8400
ggcggaaaga ctcaaggatc ttgccgctat tgagatccag ttcgatatag cccactcttg    8460
cacccagttg atcttcagca tcttttactt tcaccagcgt ttcggggtgt gcaaaaacag    8520
gcaagcaaaa tgccgcaaag aagggaatga gtgcgacacg aaaatgttgg atgctcatac    8580
tcgtcctttt tcaatattat tgaagcattt atcagggtta ctagtacgtc tctcaaggat    8640
aagtaagtaa tattaaggta cgggaggtat tggacaggcc gcaataaaat atctttattt    8700
tcattacatc tgtgtgttgg ttttttgtgt gaatcgatag tactaacata cgctctccat    8760
caaaacaaaa cgaaacaaaa caaactagca aaataggctg tccccagtgc aagtgcaggt    8820
gccagaacat ttctct                                                    8836
```

<210> SEQ ID NO 22
<211> LENGTH: 1416
<212> TYPE: DNA
<213> ORGANISM: Artificial Sequence
<220> FEATURE:
<223> OTHER INFORMATION: Ab2 antibody heavy chain

<400> SEQUENCE: 22

```
atggcctggg tgtggacctt gctattcctg atgacagctg cccagagtgc ccaagcacag      60
atccagttgg aacagtctgg acctgagctg aagaagcctg agagacagt caagatctcc     120 tgcaaggctt ctggatatat cttcacaaac aatggaatga ctgggtgaa acaggctcca     180 ggaaagggtt taaagtggat gggctgggta acacctaca ctggtaagtc aacatatgct     240
gatgacttca agggacggtt tgccttctct ttggaaacct cagccagcac tgcctatttg     300
caaatcaaca acctcaaaaa tgaggacacg gctacatatt tctgtgcaag agactctact     360
acggtaatag ctacgaatgc tatggacttc tggggtcaag gaacctcagt caccgtctcc     420
tcagcctcaa ccaagggccc atcggtcttc cccctggcac cctcctccaa gagcacctct     480
gggggcacag cggccctggg ctgcctggtc aaggactact ccccgaacc ggtgacggtg     540 tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780
ggaccgtcag tcttcctctt cccccccaaaa cccaaggaca cctcatgat ctcccggacc     840
```

| | |
|---|---|
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgtgtggt cagcgtcctc accgtcctgc accaggactg gctgaatggc | 1020 |
| aaggagtaca agtgcaaggt ctccaacaaa gccctcccag cccccatcga gaaaaccatc | 1080 |
| tccaaagcca aagggcagcc ccgagaacca caggtgtaca ccctgccccc atcccgggat | 1140 |
| gagctgacca gaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gttctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 |
| acacagaaga gcctctccct gtctccgggt aaatga | 1416 |

```
<210> SEQ ID NO 23
<211> LENGTH: 720
<212> TYPE: DNA
<213> ORGANISM: Artificial Sequence
<220> FEATURE:
<223> OTHER INFORMATION: Ab2 antibody light chain

<400> SEQUENCE: 23
```

| | |
|---|---|
| atggattcac aggcccaggt tcttatattg ctgctgctat gggtatctgg tacctgtggg | 60 |
| gacattgtga tgtcacagtc tccatcctcc ctggctgtgt cagcaggaga gaaggtcact | 120 |
| atgagctgca atccagtca gagtctgctc aacagtagaa cccgaaagaa ctacttggct | 180 |
| tggtaccagc agaaaccagg gcagtctcct aaactgctga tctactgggc atccattagg | 240 |
| gaatctgggg tccctgatcg cttcacaggc agtggatctg gacagatttt cactctcacc | 300 |
| atcagcagtg tgcaggctga agacctggca gtttattact gcaagcaatc ttataatctg | 360 |
| tggacgttcg gtggaggcac caagctggaa atcaaacgga ctgttgcggc cacatctgtc | 420 |
| ttcatcttcc cgccatctga tgagcagttg aaatctggaa ctgcctctgt tgtgtgcctg | 480 |
| ctgaataact ctatcccag agaggccaaa gtacagtgga aggtggataa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgttga | 720 |

```
<210> SEQ ID NO 24
<211> LENGTH: 7733
<212> TYPE: DNA
<213> ORGANISM: Artificial Sequence
<220> FEATURE:
<223> OTHER INFORMATION: Seq3a-HAb2 vector

<400> SEQUENCE: 24
```

| | |
|---|---|
| gttggttttt tgtgtgaatc gatagtacta acatacgctc tccatcaaaa caaaacgaaa | 60 |
| caaaacaaac tagcaaaata ggctgtcccc agtgcaagtg caggtgccag aacatttctc | 120 |
| tggcctaact ggccggtacc ggagaggggg taaaaaaatg ctgcactgtg cggctaggcc | 180 |
| ggtgagtgag cggcgcggag ccaatcagcg ctcgccgttc cgaaagttgc cttttatggc | 240 |
| tcgagtggcc gctgtggcgt cctataaaac ccggcggcgc aacgcgcagc cactgtcgag | 300 |
| tccgcgtcca cccgcgagca caggcctttc gcagctcttt cttcgccgct ccacacccgc | 360 |
| caccaggtaa gcaggacaa caggcccagc cggccacagc cctcccgtgg gcagtgaccg | 420 |
| cgctgcaggg tcgcggggga cactcggcgc ggacaccggg gaaggctgga ggtggtgcc | 480 |

```
gggccgcgga gcggacactt tcagatccaa ctttcagtcc agggtgtaga ccctttacag    540
ccgcattgcc acggtgtaga caccggtgga cccgctctgg ctcagagcac gcggcttggg    600
ggaacccatt agggtcgcag tgtgggcgct atgagagccg atgcagcttt cgggtgttga    660
accgtatctg cccaccttgg ggggaggaca caaggtcggg agccaaacgc cacgatcatg    720
ccttggtggc ccatgggtct ttgtctaaac cggtttgccc atttggcttg ccgggcgggc    780
gggcgcggcg ggcccggctc ggccgggttg ggggctgggt tgccactgcg cttgcgcgct    840
ctatggctgg gtattgggc gcgtgcacgc tggggaggga gcccttcctc ttccccctct     900
cccaagttaa acttgcgcgt gcgtattgag acttggagcg cggccaccgg ggttgggcga    960
gggcggggcc gttgtccgga agggcgggg tcgcagcggc ttcggggcgc ctgctcgcgc    1020
ttcctgctgg gtgtggtcgc ctcccgcgcg cgcactagcc gcccgccggc ggggcgaagg   1080
cggggcttgc gcccgtttgg ggaggggcg gaggcctggc ttcctgccgt ggggccgcct    1140
ccggaccagc gtttgcctct tatggtaata cgcggccgg cctgggcttc ctttgtcccc    1200
tgagtttggg cgcgcgcccc ctggcggccc gaggccgcgg cttgccggaa gtgggcaggg   1260
cggcagcggc tgcgcctagt ggcccgccag tgaccgcgac cctcttttgt gccctgatat   1320
agttcgccga attcgctagc agaacaggat gttctgatca aagagatcca aagtcagaac   1380
acgttgttct agctaaaata acacattcag agaacatgct gttctgatca aagagatcca   1440
aagtcagaac aaggtgttct agctaaaata acacattcag agaacatgat gttctgatca   1500
aagagatcca aagtcgcggc cgcgttgaca ttgattattg actagttatt aatagtaatc   1560
aattacgggg tcattagttc atagcccata tatggagttc cgcgttacat aacttacggt   1620
aaatggcccg cctggctgac cgcccaacga ccccgccca ttgacgtcaa taatgacgta   1680
tgttcccata gtaacgccaa tagggacttt ccattgacgt caatgggtgg agtatttacg   1740
gtaaactgcc cacttggcag tacatcaagt gtatcatatg ccaagtacgc cccctattga   1800
cgtcaatgac ggtaaatggc ccgcctggca ttatgcccag tacatgacct tatgggactt   1860
tcctacttgg cagtacatct acgtattagt catcgctatt accatggtga tgcggttttg   1920
gcagtacatc aatgggcgtg atagcggtt tgactcacgg ggatttccaa gtctccaccc   1980
cattgacgtc aatgggagtt tgttttggca ccaaaatcaa cgggactttc caaatgtcg   2040 taacaactcc gccccattga cgcaaatggg cggtaggcgt gtacggtggg aggtctatat   2100
aagcagagct ctctggctaa ctagagaacc cactgcttac tggcttatcg aaagcttcac   2160
catggcctgg gtgtggacct tgctattcct gatgacagct gcccagagtg cccaagcaca   2220
gatccagttg gaacagtctg gacctgagct gaagaagcct ggagagacag tcaagatctc   2280
ctgcaaggct tctggatata tcttcacaaa caatggaatg agctgggtga acaggctcc   2340 aggaaagggt ttaaagtgga tgggctgggt aaacacctac actggtaagt caacatatgc   2400
tgatgacttc aagggacggt ttgccttctc tttggaaacc tcagccagca ctgcctattt   2460
gcaaatcaac aacctcaaaa atgaggacac ggctacatat ttctgtgcaa gagactctac   2520
tacggtaata gctacgaatg ctatggactt ctggggtcaa ggaacctcag tcaccgtctc   2580
ctcagcctca accaagggcc catcggtctt ccccctggca cctcctcca agagcacctc   2640 tgggggcaca gcggccctgg gctgcctggt caaggactac ttccccgaac cggtgacggt   2700
gtcgtggaac tcaggcgccc tgaccagcgg cgtgcacacc ttcccggctg tcctacagtc   2760
ctcaggactc tactccctca gcagcgtggt gaccgtgccc tccagcagct tgggcaccca   2820
```

```
gacctacatc tgcaacgtga atcacaagcc cagcaacacc aaggtggaca agaaagttga   2880
gcccaaatct tgtgacaaaa ctcacacatg cccaccgtgc ccagcacctg aactcctggg   2940
gggaccgtca gtcttcctct tccccccaaa acccaaggac accctcatga tctcccggac   3000
ccctgaggtc acatgcgtgg tggtggacgt gagccacgaa gaccctgagg tcaagttcaa   3060
ctggtacgtg gacggcgtgg aggtgcataa tgccaagaca aagccgcggg aggagcagta   3120
caacagcacg taccgtgtgg tcagcgtcct caccgtcctg caccaggact ggctgaatgg   3180
caaggagtac aagtgcaagg tctccaacaa agccctccca gcccccatcg agaaaaccat   3240
ctccaaagcc aaagggcagc ccgagaacca caggtgtac accctgcccc catcccggga   3300
tgagctgacc aagaaccagg tcagcctgac ctgcctggtc aaaggcttct atcccagcga   3360
catcgccgtg gagtgggaga gcaatgggca gccggagaac aactacaaga ccacgcctcc   3420
cgttctggac tccgacggct ccttcttcct ctacagcaag ctcaccgtgg acaagagcag   3480
gtggcagcag gggaacgtct tctcatgctc cgtgatgcat gaggctctgc acaaccacta   3540
cacacagaag agcctctccc tgtctccggg taaatgaacg cgtgactctg gtgtgagcga   3600
attcgtgtaa taattctaga gtcggggcgg ccggccgctt cgagcagaca tgataagata   3660
cattgatgag tttggacaaa ccacaactag aatgcagtga aaaaaatgct ttatttgtga   3720
aatttgtgat gctattgctt tatttgtaac cattataagc tgcaataaac aagttaacaa   3780
caacaattgc attcatttta tgtttcaggt tcaggggag gtgtgggagg ttttttaaag   3840
caagtaaaac ctctacaaat gtggtaaaat cgataaggat ccgtttgcgt attgggcgct   3900
cttccgctga tctgcgtaat aattctagag tcggggcggc cggccgcttc gagcagacat   3960
gataagatac attgatgagt ttggacaaac cacaactaga atgcagtgaa aaaaatgctt   4020
tatttgtgaa atttgtgatg ctattgcttt atttgtaacc attataagct gcaataaaca   4080
agttaacaac aacaattgca ttcattttat gtttcaggtt caggggaggg tgtgggaggt   4140
tttttaaagc aagtaaaacc tctacaaatg tggtaaaatc gataaggatc cgcagcacca   4200
tggcctgaaa taacctctga agaggaact tggttagcta ccttctgagg cggaaagaac   4260
cagctgtgga atgtgtgtca gttagggtgt ggaaagtccc caggctcccc agcaggcaga   4320
agtatgcaaa gcatgcatct caattagtca gcaaccaggt gtggaaagtc cccaggctcc   4380
ccagcaggca gaagtatgca aagcatgcat tcaattagt cagcaaccat agtcccgccc   4440
ctaactccgc ccatcccgcc cctaactccg cccagttccg cccattctcc gccccatggc   4500
tgactaattt tttttattta tgcagaggcc gaggccgcct ctgcctctga gctattccag   4560
aagtagtgag gaggcttttt tggaggccta ggcttttgca aaaagctcga ttcttctgac   4620
actagcgcca ccatgatcga acaagacggc ctccatgctg gcagtcccgc agcttgggtc   4680
gaacgcttgt tcgggtacga ctgggcccag cagaccatcg gatgtagcga tgcggccgtg   4740
ttccgtctaa gcgctcaagg ccggcccgtg ctgttcgtga agaccgacct gagcggcgcc   4800
ctgaacgagc ttcaagacga ggctgccgc ctgagctggc tggccaccac cggcgtaccc   4860
tgcgccgctg tgttggatgt tgtgaccgaa gccggccggg actggctgct gctgggcgag   4920
gtccctggcc aggatctgct gagcagccac cttgcccccg ctgagaaggt ttctatcatg   4980
gccgatgcaa tgcggcgcct gcacacactg accccgcta cctgccccttt cgaccaccag   5040
gctaagcatc ggatcgagcg tgctcggacc cgcatggagg ccggcctggt ggaccaggac   5100
gacctggaca ggagcatca gggcctggcc cccgctgaac tgttcgcccg actgaaagcc   5160
cgcatgccgg acggtgagga cctggttgtc acacacggag atgcctgcct ccctaacatc   5220
```

```
atggtcgaga atggccgctt ctccggcttc atcgactgcg gtcgcctagg agttgccgac    5280
cgctaccagg acatcgccct ggccacccgc gacatcgctg aggagcttgg cggcgagtgg    5340
gccgaccgct tcttagtctt gtacggcatc gcagctcccg acagccagcg catcgccttc    5400
taccgcttgc tcgacgagtt cttttaatga tctagaaccg gtcatggccg caataaaata    5460
tctttatttt cattacatct gtgtgttggt tttttgtgtg ttcgaactag atgctgtcga    5520
ccgatgccct tgagagcctt caacccagtc agctccttcc ggtgggcgcg gggcatgact    5580
atcgtcgccg cacttatgac tgtcttcttt atcatgcaac tcgtaggaca ggtgccggca    5640
gcgctcttcc gcttcctcgc tcactgactc gctgcgctcg gtcgttcggc tgcggcgagc    5700
ggtatcagct cactcaaagg cggtaatacg gttatccaca gaatcagggg ataacgcagg    5760
aaagaacatg tgagcaaaag gccagcaaaa ggccaggaac cgtaaaaagg ccgcgttgct    5820
ggcgtttttc cataggctcc gcccccctga cgagcatcac aaaaatcgac gctcaagtca    5880
gaggtggcga aacccgacag gactataaag ataccaggcg tttccccctg gaagctccct    5940
cgtgcgctct cctgttccga ccctgccgct taccggatac ctgtccgcct ttctcccttc    6000
gggaagcgtg gcgctttctc atagctcacg ctgtaggtat ctcagttcgg tgtaggtcgt    6060
tcgctccaag ctgggctgtg tgcacgaacc ccccgttcag cccgaccgct gcgccttatc    6120
cggtaactat cgtcttgagt ccaacccggt aagacacgac ttatcgccac tggcagcagc    6180
cactggtaac aggattagca gagcgaggta tgtaggcggt gctacagagt tcttgaagtg    6240
gtggcctaac tacggctaca ctagaagaac agtatttggt atctgcgctc tgctgaagcc    6300
agttaccttc ggaaaaagag ttggtagctc ttgatccggc aaacaaacca ccgctggtag    6360
cggtggtttt tttgtttgca agcagcagat tacgcgcaga aaaaaaggat ctcaagaaga    6420
tcctttgatc ttttctacgg ggtctgacgc tcagtggaac gaaaactcac gttaagggat    6480
tttggtcatg agattatcaa aaaggatctt cacctagatc cttttaaatt aaaaatgaag    6540
ttttaaatca atctaaagta tatatgagta aacttggtct gacagcggcc gcaaatgcta    6600
aaccactgca gtggttacca gtgcttgatc agtgaggcac cgatctcagc gatctgccta    6660
tttcgttcgt ccatagtggc ctgactcccc gtcgtgtaga tcactacgat tcgtgagggc    6720
ttaccatcag gccccagcgc agcaatgatg ccgcgagagc gcgcgttcacc ggccccccgat   6780 ttgtcagcaa tgaaccagcc agcagggagg ccgagcgaa gaagtggtcc tgctactttg    6840
tccgcctcca tccagtctat gagctgctgt cgtgatgcta gagtaagaag ttcgccagtg    6900
agtagtttcc gaagagttgt ggccattgct actggcatcg tggtatcacg ctcgtcgttc    6960
ggtatggctt cgttcaactc tggttcccag cggtcaagcc gggtcacatg atcacccata    7020
ttatgaagaa atgcagtcag ctccttaggg cctccgatcg ttgtcagaag taagttggcc    7080
gcggtgttgt cgctcatggt aatggcagca ctacacaatt ctcttaccgt catgccatcc    7140
gtaagatgct tttccgtgac cggcgagtac tcaaccaagt cgttttgtga gtagtgtata    7200
cggcgaccaa gctgctcttg cccggcgtct atacgggaca acaccgcgcc acatagcagt    7260
actttgaaag tgctcatcat cgggaatcgt tcttcggggc ggaaagactc aaggatcttg    7320
ccgctattga gatccagttc gatatagccc actcttgcac ccagttgatc ttcagcatct    7380
tttactttca ccagcgtttc ggggtgtgca aaaacaggca agcaaaatgc cgcaaagaag    7440
ggaatgagtg cgcacacgaa aatgttggatg ctcatactcg tcctttttca atattattga    7500
agcatttatc agggttacta gtacgtctct caaggataag taagtaatat taaggtacgg    7560
```

-continued

```
gaggtattgg acaggccgca ataaaatatc tttattttca ttacatctgt gtgttggttt    7620
tttgtgtgaa tcgatagtac taacatacgc tctccatcaa aacaaaacga aacaaaacaa    7680
actagcaaaa taggctgtcc ccagtgcaag tgcaggtgcc agaacatttc tct           7733
```

<210> SEQ ID NO 25
<211> LENGTH: 6528
<212> TYPE: DNA
<213> ORGANISM: Artificial Sequence
<220> FEATURE:
<223> OTHER INFORMATION: Seq3a-LAb2 vector

<400> SEQUENCE: 25

```
ggatccctac cggtgctgcg gccgcgcagt taacgccgcc cctctccctc ccccccccct      60
aacgttactg gccgaagccg cttggaataa ggccggtgtg cgtttgtcta tatgttattt     120
tccaccatat tgccgtcttt tggcaatgtg agggcccgga acctggccc tgtcttcttg      180 acgagcattc ctaggggtct ttcccctctc gccaaaggaa tgcaaggtct gttgaatgtc    240
gtgaaggaag cagttcctct ggaagcttct tgaagacaaa caacgtctgt agcgacccttt   300 tgcaggcagc ggaaccccccc acctggcgac aggtgcctct gcggccaaaa gccacgtgta   360
taagatacac ctgcaaaggc ggcacaaccc cagtgccacg ttgtgagttg atagttgtg     420 gaaagagtca aatggctctc ctcaagcgta ttcaacaagg gctgaagga tgcccagaag     480 gtacccatt gtatgggatc tgatctgggg cctcggtaca catgctttac atgtgtttag     540
tcgaggttaa aaaacgtct aggccccccg aaccacgggg acgtggtttt cctttgaaaa     600
acacgatgat aatatggcca caagatctgc caccatggtt cgaccattga actgcatcgt   660
cgccgtgtcc caaaatatgg ggattggcaa gaacggagac ctaccctggc ctccgctcag   720
gaacgagttc aagtacttcc aaagaatgac cacaacctct tcagtggaag gtaaacagaa   780
tctggtgatt atgggtagga aaacctggtt ctccattcct gagaagaatc gacctttaaa   840
ggacagaatt aatatagttc tcagtagaga actcaaagaa ccaccacgag gagctcattt   900
tcttgccaaa agtttggatg atgccttaag acttattgaa caaccggaat tggcaagtaa   960
agtagacatg gttggataag tcggaggcag ttctgtttac caggaagcca tgaatcaacc  1020
aggccacctc agactctttg tgacaaggat catgcaggaa tttgaaagtg acacgttttt  1080
cccagaaatt gatttgggga aatataaact tctcccagaa tacccaggcg tcctctctga  1140
ggtccaggag gaaaaaggca tcaagtataa gtttgaagtc tacgagaaga aagactaaaa  1200
ccggttagta atgagtttaa acgggggagg ctaactgaaa cacggaagga gacaataccg  1260
gaaggaaccc gcgctatgac ggcaataaaa agacagaata aaacgcacgg gtgttgggtc  1320
gtttgttcat aaacgcgggg ttcggtccca gggctggcac tctgtcgata ccccaccgag  1380 acccccattgg ggccaatacg cccgcgtttc ttccttttcc ccaccccacc cccaagttc   1440 gggtgaaggc ccagggctcg cagccaacgt cggggcggca ggccctgcca ttaccgtcga  1500
cctctagcta gagcttggcg taatcatggt catagctgtt tcctgtgtga aattgttatc   1560
cgctcacaat tccacacaac atacgagccg gaagcataaa gtgtaaagcc tggggtgcct   1620
aatgagtgag ctaactcaca ttaattgcgt tgcgctcact gcccgctttc cagtcgggaa   1680
acctgtcgtg ccagctgcat taatgaatcg gccaacgcgc ggggagaggc ggtttgcgta   1740
ttgggcgctc ttccgcttcc tcgctcactg actcgctgcg ctcggtcgtt cggctgcggc   1800
gagcggtatc agctcactca aaggcggtaa tacggttatc cacagaatca ggggataacg  1860
caggaaagaa catgtgagca aaaggccagc aaaaggccag gaaccgtaaa aaggccgcgt   1920
```

```
tgctggcgtt tttccatagg ctccgccccc ctgacgagca tcacaaaaat cgacgctcaa   1980
gtcagaggtg gcgaaacccg acaggactat aaagatacca ggcgtttccc cctggaagct   2040
ccctcgtgcg ctctcctgtt ccgaccctgc cgcttaccgg atacctgtcc gcctttctcc   2100 cttcggaag cgtggcgctt tctcatagct cacgctgtag gtatctcagt tcggtgtagg    2160
tcgttcgctc caagctgggc tgtgtgcacg aaccccccgt tcagcccgac cgctgcgcct   2220
tatccggtaa ctatcgtctt gagtccaacc cggtaagaca cgacttatcg ccactggcag   2280
cagccactgg taacaggatt agcagagcga ggtatgtagg cggtgctaca gagttcttga   2340
agtggtggcc taactacggc tacactagaa gaacagtatt tggtatctgc gctctgctga   2400
agccagttac cttcggaaaa agagttggta gctcttgatc cggcaaacaa accaccgctg   2460
gtagcggttt ttttgtttgc aagcagcaga ttacgcgcag aaaaaaagga tctcaagaag   2520
atcctttgat cttttctacg gggtctgacg ctcagtggaa cgaaaactca cgttaaggga   2580
ttttggtcat gagattatca aaaaggatct tcacctagat ccttttaaat taaaaatgaa   2640
gttttaaatc aatctaaagt atatatgagt aaacttggtc tgacagttac caatgcttaa   2700
tcagtgaggc acctatctca gcgatctgtc tatttcgttc atccatagtt gcctgactcc   2760
ccgtcgtgta gataactacg atacgggagg gcttaccatc tggccccagt gctgcaatga   2820
taccgcgaga cccacgctca ccggctccag atttatcagc aataaaccag ccagccggaa   2880
gggccgagcg cagaagtggt cctgcaactt tatccgcctc catccagtct attaattgtt   2940
gccgggaagc tagagtaagt agttcgccag ttaatagttt gcgcaacgtt gttgccattg   3000
ctacaggcat cgtggtgtca cgctcgtcgt ttggtatggc ttcattcagc tccggttccc   3060
aacgatcaag gcgagttaca tgatccccca tgttgtgcaa aaaagcggtt agctccttcg   3120
gtcctccgat cgttgtcaga agtaagttgg ccgcagtgtt atcactcatg gttatggcag   3180
cactgcataa ttctcttact gtcatgccat ccgtaagatg cttttctgtg actggtgagt   3240
actcaaccaa gtcattctga gaatagtgta tgcggcgacc gagttgctct tgcccggcgt   3300
caatacggga taataccgcg ccacatagca gaactttaaa agtgctcatc attggaaaac   3360
gttcttcggg gcgaaaactc tcaaggatct taccgctgtt gagatccagt tcgatgtaac   3420
ccactcgtgc acccaactga tcttcagcat cttttacttt caccagcgtt tctgggtgag   3480
caaaaacagg aaggcaaaat gccgcaaaaa agggaataag ggcgacacgg aaatgttgaa   3540
tactcatact cttcctttt caatattatt gaagcattta tcagggttat tgtctcatga    3600
gcggatacat atttgaatgt atttagaaaa ataaacaaat aggggttccg cgcacatttc   3660
cccgaaaagt gccacctgac gtcgacggat cgggagatct ggagagggg taaaaaaatg    3720 ctgcactgtg cggctaggcc ggtgagtgag cggcgcggag ccaatcagcg ctcgccgttc   3780
cgaaagttgc cttttatggc tcgagtggcc gctgtggcgt cctataaaac ccggcggcgc   3840
aacgcgcagc cactgtcgag tccgcgtcca cccgcgagca caggcctttc gcagctcttt   3900
cttcgccgct ccacacccgc caccaggtaa gcagggacaa caggcccagc cggccacagc   3960
cctcccgtgg gcagtgaccg cgctgcaggg tcgcggggga cactcggcgc ggacaccggg   4020
gaaggctgga gggtggtgcc gggccgcgga gcggacactt tcagatccaa cttccagtcc   4080
agggtgtaga cccttacag ccgcattgcc acggtgtaga caccggtgga cccgctctgg    4140
ctcagagcac gcggcttggg ggaacccatt agggtcgcag tgtgggcgct atgagagccg   4200
atgcagcttt cgggtgttga accgtatctg cccaccttgg ggggaggaca caaggtcggg   4260
```

| | |
|---|---|
| agccaaacgc cacgatcatg ccttggtggc ccatgggtct ttgtctaaac cggtttgccc | 4320 |
| atttggcttg ccgggcgggc gggcgcggcg ggcccggctc ggccgggttg ggggctgggt | 4380 |
| tgccactgcg cttgcgcgct ctatggctgg gtattggggc gcgtgcacgc tggggaggga | 4440 |
| gcccttcctc ttccccctct cccaagttaa acttgcgcgt gcgtattgag acttggagcg | 4500 |
| cggccaccgg ggttgggcga gggcggggcc gttgtccgga aggggcgggg tcgcagcggc | 4560 |
| ttcggggcgc ctgctcgcgc ttcctgctgg gtgtggtcgc ctcccgcgcg cgcactagcc | 4620 |
| gcccgccggc ggggcgaagg cggggcttgc gcccgtttgg ggaggggggcg gaggcctggc | 4680 |
| ttcctgccgt ggggccgcct ccggaccagc gtttgcctct tatggtaata acgcggccgg | 4740 |
| cctgggcttc ctttgtcccc tgagtttggg cgcgcgcccc ctggcggccc gaggccgcgg | 4800 |
| cttgccggaa gtgggcaggg cggcagcggc tgcgcctagt ggcccgccag tgaccgcgac | 4860 |
| cctcttttgt gccctgatat agttcgccga attcgctagc agaacaggat gttctgatca | 4920 |
| aagagatcca aagtcagaac acgttgttct agctaaaata acacattcag agaacatgct | 4980 |
| gttctgatca aagagatcca aagtcagaac aaggtgttct agctaaaata acacattcag | 5040 |
| agaacatgat gttctgatca aagagatcca aagtcgcggc cgcgttgaca ttgattattg | 5100 |
| actagttatt aatagtaatc aattacgggg tcattagttc atagcccata tatggagttc | 5160 |
| cgcgttacat aacttacggt aaatggcccg cctggctgac cgcccaacga ccccgccca | 5220 |
| ttgacgtcaa taatgacgta tgttcccata gtaacgccaa tagggacttt ccattgacgt | 5280 |
| caatgggtgg agtatttacg gtaaactgcc cacttggcag tacatcaagt gtatcatatg | 5340 |
| ccaagtacgc cccctattga cgtcaatgac ggtaaatggc ccgcctggca ttatgcccag | 5400 |
| tacatgacct tatgggactt tcctacttgg cagtacatct acgtattagt catcgctatt | 5460 |
| accatggtga tgcggttttg gcagtacatc aatgggcgtg gatagcggtt tgactcacgg | 5520 |
| ggatttccaa gtctccaccc cattgacgtc aatgggagtt tgttttggca ccaaaatcaa | 5580 |
| cgggactttc caaaatgtcg taacaactcc gccccattga cgcaaatggg cggtaggcgt | 5640 |
| gtacggtggg aggtctatat aagcagagct ctctggctaa ctagagaacc cactgcttac | 5700 |
| tggcttatcg aaagcttctc tggctaacta gagaacccac tgcttactgg cttatcgaaa | 5760 |
| ttaatacgac tcactatagg gagacccaag ctggctagca agatggattc acaggcccag | 5820 |
| gttcttatat tgctgctgct atgggtatct ggtacctgtg gggacattgt gatgtcacag | 5880 |
| tctccatcct ccctggctgt gtcagcagga gagaaggtca ctatgagctg caaatccagt | 5940 |
| cagagtctgc tcaacagtag aacccgaaag aactacttgg cttggtacca gcagaaacca | 6000 |
| gggcagtctc ctaaactgct gatctactgg gcatccatta gggaatctgg ggtccctgat | 6060 |
| cgcttcacag gcagtggatc tgggacagat ttcactctca ccatcagcag tgtgcaggct | 6120 |
| gaagacctgg cagtttatta ctgcaagcaa tcttataatc tgtggacgtt cggtggaggc | 6180 |
| accaagctgg aaatcaaacg gactgttgcg gcaccatctg tcttcatctt cccgccatct | 6240 |
| gatgagcagt tgaaatctgg aactgcctct gttgtgtgcc tgctgaataa cttctatccc | 6300 |
| agagaggcca agtacagtg gaaggtggat aacgccctcc aatcgggtaa ctcccaggag | 6360 |
| agtgtcacag agcaggacag caaggacagc acctacagcc tcagcagcac cctgacgctg | 6420 |
| agcaaagcag actacgagaa acacaaagtc tacgcctgcg aagtcaccca tcagggcctg | 6480 |
| agctcgcccg tcacaaagag cttcaacagg ggagagtgtt gaggatcc | 6528 |

```
<210> SEQ ID NO 26
<211> LENGTH: 564
```

<212> TYPE: DNA
<213> ORGANISM: Artificial Sequence
<220> FEATURE:
<223> OTHER INFORMATION: Enzyme dihydrofolate reductase (dhfr)

<400> SEQUENCE: 26

```
atggttcgac cattgaactg catcgtcgcc gtgtcccaaa atatggggat tggcaagaac    60
ggagacctac cctggcctcc gctcaggaac gagttcaagt acttccaaag aatgaccaca   120
acctcttcag tggaaggtaa acagaatctg gtgattatgg gtaggaaaac ctggttctcc   180
attcctgaga agaatcgacc tttaaaggac agaattaata tagttctcag tagagaactc   240
aaagaaccac cacgaggagc tcattttctt gccaaaagtt tggatgatgc cttaagactt   300
attgaacaac cggaattggc aagtaaagta gacatggttt ggatagtcgg aggcagttct   360
gtttaccagg aagccatgaa tcaaccaggc cacctcagac tctttgtgac aaggatcatg   420
caggaatttg aaagtgacac gttttttccca gaaattgatt tggggaaata taaacttctc   480
ccagaatacc caggcgtcct ctctgaggtc caggaggaaa aaggcatcaa gtataagttt   540
gaagtctacg agaagaaaga ctaa                                          564
```

<210> SEQ ID NO 27
<211> LENGTH: 31
<212> TYPE: DNA
<213> ORGANISM: Artificial Sequence
<220> FEATURE:
<223> OTHER INFORMATION: F1 primer

<400> SEQUENCE: 27

```
aaaaagatct ggagaggggg taaaaaaatg a                                   31
```

<210> SEQ ID NO 28
<211> LENGTH: 45
<212> TYPE: DNA
<213> ORGANISM: Artificial Sequence
<220> FEATURE:
<223> OTHER INFORMATION: R1 primer

<400> SEQUENCE: 28

```
tcaacgcggc cgcaaaaaag aattcggcga actatatcag ggcac                    45
```

<210> SEQ ID NO 29
<211> LENGTH: 534
<212> TYPE: DNA
<213> ORGANISM: Artificial Sequence
<220> FEATURE:
<223> OTHER INFORMATION: Enhancer CMV promoter

<400> SEQUENCE: 29

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccat         534
```

```
<210> SEQ ID NO 30
<211> LENGTH: 89
<212> TYPE: DNA
<213> ORGANISM: Artificial Sequence
<220> FEATURE:
<223> OTHER INFORMATION: Core CMV

<400> SEQUENCE: 30
gcaaatgggc ggtaggcgtg tacggtggga ggtctatata agcagagctc tctggctaac    60
tagagaaccc actgcttact ggcttatca                                      89

<210> SEQ ID NO 31
<211> LENGTH: 239
<212> TYPE: PRT
<213> ORGANISM: Artificial Sequence
<220> FEATURE:
<223> OTHER INFORMATION: Ab1 antibody light chain

<400> SEQUENCE: 31
```

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Ile Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

```
<210> SEQ ID NO 32
<211> LENGTH: 470
<212> TYPE: PRT
<213> ORGANISM: Artificial Sequence
<220> FEATURE:
<223> OTHER INFORMATION: Ab1 antibody heavy chain

<400> SEQUENCE: 32
```

```
Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
```

420                 425                 430
Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 33
<211> LENGTH: 239
<212> TYPE: PRT
<213> ORGANISM: Artificial Sequence
<220> FEATURE:
<223> OTHER INFORMATION: Ab2 antibody light chain

<400> SEQUENCE: 33

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Ile Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 34
<211> LENGTH: 471
<212> TYPE: PRT
<213> ORGANISM: Artificial Sequence
<220> FEATURE:
<223> OTHER INFORMATION: Ab2 antibody heavy chain

<400> SEQUENCE: 34

Met Ala Trp Val Trp Thr Leu Leu Phe Leu Met Thr Ala Ala Gln Ser
1               5                   10                  15

```
Ala Gln Ala Gln Ile Gln Leu Glu Gln Ser Gly Pro Glu Leu Lys Lys
             20                  25                  30

Pro Gly Glu Thr Val Lys Ile Ser Cys Lys Ala Ser Gly Tyr Ile Phe
         35                  40                  45

Thr Asn Asn Gly Met Ser Trp Val Lys Gln Ala Pro Gly Lys Gly Leu
     50                  55                  60

Lys Trp Met Gly Trp Val Asn Thr Tyr Thr Gly Lys Ser Thr Tyr Ala
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Asn Asn Leu Lys Asn Glu Asp Thr Ala Thr
             100                 105                 110

Tyr Phe Cys Ala Arg Asp Ser Thr Val Ile Ala Thr Asn Ala Met
         115                 120                 125

Asp Phe Trp Gly Gln Gly Thr Ser Val Thr Val Ser Ser Ala Ser Thr
     130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                 165                 170                 175

Pro Val Thr Val Ser Trp Asn Ser Gly Ala Leu Thr Ser Gly Val His
             180                 185                 190

Thr Phe Pro Ala Val Leu Gln Ser Ser Gly Leu Tyr Ser Leu Ser Ser
         195                 200                 205

Val Val Thr Val Pro Ser Ser Ser Leu Gly Thr Gln Thr Tyr Ile Cys
     210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                 245                 250                 255

Glu Leu Leu Gly Gly Pro Ser Val Phe Leu Phe Pro Pro Lys Pro Lys
             260                 265                 270

Asp Thr Leu Met Ile Ser Arg Thr Pro Glu Val Thr Cys Val Val Val
         275                 280                 285

Asp Val Ser His Glu Asp Pro Glu Val Lys Phe Asn Trp Tyr Val Asp
     290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                 325                 330                 335

Trp Leu Asn Gly Lys Glu Tyr Lys Cys Lys Val Ser Asn Lys Ala Leu
             340                 345                 350

Pro Ala Pro Ile Glu Lys Thr Ile Ser Lys Ala Lys Gly Gln Pro Arg
         355                 360                 365

Glu Pro Gln Val Tyr Thr Leu Pro Pro Ser Arg Asp Glu Leu Thr Lys
     370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                 405                 410                 415

Thr Thr Pro Pro Val Leu Asp Ser Asp Gly Ser Phe Phe Leu Tyr Ser
             420                 425                 430

Lys Leu Thr Val Asp Lys Ser Arg Trp Gln Gln Gly Asn Val Phe Ser
```

435                 440                 445
Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 35
<211> LENGTH: 6774
<212> TYPE: DNA
<213> ORGANISM: Artificial Sequence
<220> FEATURE:
<223> OTHER INFORMATION: Seq4-Luc vector

<400> SEQUENCE: 35
ggcctaactg gccggtacct gagctcgcta gcggagaggg ggtaaaaaaa tgctgcactg      60
tgcggctagg ccggtgagtg agcggcgcgg agccaatcag cgctcgccgt tccgaaagtt     120 gcctttatg gctcgagtgg ccgctgtggc gtcctataaa acccggcggc gcaacgcgca     180
gccactgtcg agtccgcgtc cacccgcgag cacaggcctt tcgcagctct ttcttcgccg     240
ctccacaccc gccaccaggt aagcagggac aacaggccca gccggccaca gccctcccgt     300
gggcagtgac cgcgctgcag ggtcgcgggg gacactcggc gcggacaccg gggaaggctg     360
gagggtggtg ccgggccgcg gagcggacac tttcagatcc aactttcagt ccagggtgta     420 gacccttttac agccgcattg ccacggtgta gacaccggtg gacccgctct ggctcagagc     480
acgcggcttg ggggaaccca ttagggtcgc agtgtgggcg ctatgagagc cgatgcagct     540
ttcgggtgtt gaaccgtatc tgcccacctt gggggggagga cacaaggtcg ggagccaaac     600
gccacgatca tgccttggtg gcccatgggt ctttgtctaa accggtttgc ccatttggct     660
tgccgggcgg gcgggcgcgg cgggcccggc tcggccgggt tgggggctgg gttgccactg     720
cgcttgcgcg ctctatggct gggtattggg gcgcgtgcac gctgggagg gagcccttcc     780 tcttcccccct ctcccaagtt aaacttgcgc gtgcgtattg agacttggag cgcggccacc     840 gggggttgggc gagggcgggg ccgttgtccg gaaggggcgg ggtcgcagcg gcttcggggc     900
gcctgctcgc gcttcctgct gggtgtggtc gcctcccgcg cgcgcactag ccgcccgccg     960
gcggggcgaa ggcggggctt gcgcccgttt ggggaggggg cggaggcctg gcttcctgcc    1020
gtggggccgc ctccggacca gcgtttgcct cttatggtaa taacgcggcc ggcctgggct    1080
tcctttgtcc cctgagtttg ggcgcgcgcc ccctggcggc ccgaggccgc ggcttgccgg    1140
aagtgggcag ggcggcagcg gctgcgccta gtggcccgcc agtgaccgcg accctctttt    1200
gtgccctgat atagttcgcc agatctggcc tcggcggcca agcttggcaa tccggtactg    1260
ttggtaaagc caccatggaa gatgccaaaa acattaagaa gggcccagcg ccattctacc    1320
cactcgaaga cgggaccgcc ggcgagcagc tgcacaaagc catgaagcgc tacgccctgg    1380
tgcccggcac catcgccttt accgacgcac atatcgaggt ggacattacc tacgccgagt    1440
acttcgagat gagcgttcgg ctggcagaag ctatgaagcg ctatgggctg aatacaaacc    1500
atcggatcgt ggtgtgcagc gagaatagct tgcagttctt catgcccgtg ttgggtgccc    1560
tgttcatcgg tgtggctgtg gccccagcta acgacatcta caacgagcgc gagctgctga    1620
acagcatggg catcagccag cccaccgtcg tattcgtgag caagaaaggg ctgcaaaaga    1680
tcctcaacgt gcaaaagaag ctaccgatca tacaaaagat catcatcatg gatagcaaga    1740
ccgactacca gggcttccaa agcatgtaca ccttcgtgac ttcccatttg ccacccggct    1800
tcaacgagta cgacttcgtg cccgagagct tcgaccggga caaaaccatc gccctgatca    1860

```
tgaacagtag tggcagtacc ggattgccca agggcgtagc cctaccgcac cgcaccgctt    1920
gtgtccgatt cagtcatgcc cgcgacccca tcttcggcaa ccagatcatc cccgacaccg    1980
ctatcctcag cgtggtgcca tttcaccacg gcttcggcat gttcaccacg ctgggctact    2040
tgatctgcgg ctttcgggtc gtgctcatgt accgcttcga ggaggagcta ttcttgcgca    2100
gcttgcaaga ctataagatt caatctgccc tgctggtgcc cacactattt agcttcttcg    2160
ctaagagcac tctcatcgac aagtacgacc taagcaactt gcacgagatc gccagcggcg    2220
gggcgccgct cagcaaggag gtaggtgagg ccgtggccaa acgcttccac ctaccaggca    2280
tccgccaggg ctacggcctg acagaaacaa ccagcgccat tctgatcacc cccgaagggg    2340
acgacaagcc tggcgcagta ggcaaggtgg tgcccttctt cgaggctaag gtggtggact    2400
tggacaccgg taagacactg ggtgtgaacc agcgcggcga gctgtgcgtc cgtggcccca    2460
tgatcatgag cggctacgtt aacaaccccg aggctacaaa cgctctcatc gacaaggacg    2520
gctggctgca cagcggcgac atcgcctact gggacgagga cgagcacttc ttcatcgtgg    2580
accggctgaa gagcctgatc aaatacaagg ctaccaggt agccccagcc gaactggaga    2640
gcatcctgct gcaacacccc aacatcttcg acgccgggt cgccggcctg cccgacgacg    2700
atgccggcga gctgcccgcc gcagtcgtcg tgctggaaca cggtaaaacc atgaccgaga    2760
aggagatcgt ggactatgtg gccagccagg ttacaaccgc caagaagctg cgcggtggtg    2820
ttgtgttcgt ggacgaggtg cctaaaggac tgaccggcaa gttggacgcc cgcaagatcc    2880
gcgagattct cattaaggcc aagaagggcg gcaagatcgc cgtgtaataa ttctagagtc    2940
ggggcggccg ccgcttcga gcagacatga taagatacat tgatgagttt ggacaaacca    3000
caactagaat gcagtgaaaa aaatgcttta tttgtgaaat ttgtgatgct attgctttat    3060
ttgtaaccat tataagctgc aataaacaag ttaacaacaa caattgcatt cattttatgt    3120
ttcaggttca gggggaggtg tgggaggttt tttaaagcaa gtaaacctc tacaaatgtg    3180 gtaaaatcga taaggatccg tttgcgtatt gggcgctctt ccgctgatct gcgcagcacc    3240
atggcctgaa ataacctctg aaagaggaac ttggttagct accttctgag gcggaaagaa    3300
ccagctgtgg aatgtgtgtc agttagggtg tggaaagtcc ccaggctccc cagcaggcag    3360
aagtatgcaa agcatgcatc tcaattagtc agcaaccagg tgtggaaagt ccccaggctc    3420
cccagcaggc agaagtatgc aaagcatgca tctcaattag tcagcaacca tagtcccgcc    3480
cctaactccg cccatcccgc ccctaactcc gcccagttcc gcccattctc cgccccatgg    3540
ctgactaatt ttttttattt atgcagaggc cgaggccgcc tctgcctctg agctattcca    3600
gaagtagtga ggaggctttt ttggaggcct aggcttttgc aaaaagctcg attcttctga    3660
cactagcgcc accatgatcg aacaagacgg cctccatgct ggcagtccg cagcttgggt    3720 cgaacgcttg ttcgggtacg actgggccca gcagaccatc ggatgtagcg atgcggccgt    3780
gttccgtcta gcgctcaag gccggcccgt gctgttcgtg aagaccgacc tgagcggcgc    3840
cctgaacgag cttcaagacg aggctgcccg cctgagctgg ctggccacca ccggcgtacc    3900
ctgcgccgct gtgttggatg ttgtgaccga agcggccgg gactggctgc tgctgggcga    3960
ggtccctggc caggatctgc tgagcagcca ccttgccccc gctgagaagg tttctatcat    4020
ggccgatgca atgcggcgcc tgcacaccct ggaccccgct acctgccct tcgaccacca    4080 ggctaagcat cggatcgagc gtgctcggac ccgcatggag gccggcctgg tggaccagga    4140
cgacctggac gaggagcatc agggcctggc ccccgctgaa ctgttcgccc gactgaaagc    4200
```

```
ccgcatgccg gacggtgagg acctggttgt cacacacgga gatgcctgcc tccctaacat   4260
catggtcgag aatggccgct tctccggctt catcgactgc ggtcgcctag gagttgccga   4320
ccgctaccag gacatcgccc tggccacccg cgacatcgct gaggagcttg cggcgagtg    4380 ggccgaccgc ttcttagtct tgtacggcat cgcagctccc gacagccagc gcatcgcctt   4440
ctaccgcttg ctcgacgagt tcttttaatg atctagaacc ggtcatggcc gcaataaaat   4500
atctttattt tcattacatc tgtgtgttgg ttttttgtgt gttcgaacta gatgctgtcg   4560
accgatgccc ttgagagcct tcaacccagt cagctccttc cggtgggcgc ggggcatgac   4620
tatcgtcgcc gcacttatga ctgtcttctt tatcatgcaa ctcgtaggac aggtgccggc   4680
agcgctcttc cgcttcctcg ctcactgact cgctgcgctc ggtcgttcgg ctgcggcgag   4740
cggtatcagc tcactcaaag gcggtaatac ggttatccac agaatcaggg gataacgcag   4800
gaaagaacat gtgagcaaaa ggccagcaaa aggccaggaa ccgtaaaaag gccgcgttgc   4860
tggcgttttt ccataggctc cgcccccctg acgagcatca caaaaatcga cgctcaagtc   4920
agaggtggcg aaacccgaca ggactataaa gataccaggc gtttccccct ggaagctccc   4980
tcgtgcgctc tcctgttccg accctgccgc ttaccggata cctgtccgcc tttctccctt   5040
cgggaagcgt ggcgctttct catagctcac gctgtaggta tctcagttcg gtgtaggtcg   5100
ttcgctccaa gctgggctgt gtgcacgaac ccccgttca gcccgaccgc tgcgccttat    5160
ccggtaacta tcgtcttgag tccaacccgg taagacacga cttatcgcca ctggcagcag   5220
ccactggtaa caggattagc agagcgaggt atgtaggcgg tgctacagag ttcttgaagt   5280
ggtggcctaa ctacggctac actagaagaa cagtatttgg tatctgcgct ctgctgaagc   5340
cagttacctt cggaaaaaga gttggtagct cttgatccgg caaacaaacc accgctggta   5400
gcggtggttt ttttgtttgc aagcagcaga ttacgcgcag aaaaaaagga tctcaagaag   5460
atcctttgat cttttctacg gggtctgacg ctcagtggaa cgaaaactca cgttaaggga   5520
ttttggtcat gagattatca aaaaggatct tcacctagat ccttttaaat taaaaatgaa   5580
gttttaaatc aatctaaagt atatatgagt aaacttggtc tgacagcggc cgcaaatgct   5640
aaaccactgc agtggttacc agtgcttgat cagtgaggca ccgatctcag cgatctgcct   5700
atttcgttcg tccatagtgg cctgactccc cgtcgtgtag atcactacga ttcgtgaggg   5760
cttaccatca ggccccagcg cagcaatgat gccgcgagag ccgcgttcac cggcccccga   5820
tttgtcagca atgaaccagc cagcagggag ggccgagcga agaagtggtc ctgctacttt   5880
gtccgcctcc atccagtcta tgagctgctg tcgtgatgct agagtaagaa gttcgccagt   5940
gagtagtttc cgaagagttg tggccattgc tactggcatc gtggtatcac gctcgtcgtt   6000
cggtatggct tcgttcaact ctggttccca gcggtcaagc cgggtcacat gatcacccat   6060
attatgaaga aatgcagtca gctccttagg gcctccgatc gttgtcagaa gtaagttggc   6120
cgcggtgttg tcgctcatgg taatggcagc actacacaat tctcttaccg tcatgccatc   6180
cgtaagatgc ttttccgtga ccggcgagta ctcaaccaag tcgttttgtg agtagtgtat   6240
acggcgacca agctgctctt gcccggcgtc tatacgggac aacaccgcgc cacatagcag   6300
tactttgaaa gtgctcatca tcgggaatcg ttcttcgggg cggaaagact caaggatctt   6360
gccgctattg agatccagtt cgatatagcc cactcttgca cccagttgat cttcagcatc   6420
ttttactttc accagcgttt cggggtgtgc aaaaacaggc aagcaaaatg ccgcaaagaa   6480
gggaatgagt gcgacacgaa aatgttggat gctcatactc gtccttttc aatattattg    6540 aagcatttat cagggttact agtacgtctc tcaaggataa gtaagtaata ttaaggtacg   6600
```

```
ggaggtattg gacaggccgc aataaaatat ctttattttc attacatctg tgtgttggtt    6660
ttttgtgtga atcgatagta ctaacatacg ctctccatca aaacaaaacg aaacaaaaca    6720
aactagcaaa ataggctgtc cccagtgcaa gtgcaggtgc cagaacattt ctct          6774
```

<210> SEQ ID NO 36
<211> LENGTH: 5675
<212> TYPE: DNA
<213> ORGANISM: Artificial Sequence
<220> FEATURE:
<223> OTHER INFORMATION: Seq5-Luc vector

<400> SEQUENCE: 36

```
ggcctaactg gccggtacct gagctcgcta gcctcgagga tatcaagatc tgcaaatggg     60
cggtaggcgt gtacggtggg aggtctatat aagcagagct ctctggctaa ctagagaacc    120
cactgcttac tggcttatca agcttggca atccggtact gttggtaaag ccaccatgga    180
agatgccaaa aacattaaga agggcccagc gccattctac ccactcgaag acggaccgc    240 cggcgagcag ctgcacaaag ccatgaagcg ctacgccctg gtgcccggca ccatcgcctt    300
taccgacgca catatcgagg tggacattac ctacgccgag tacttcgaga tgagcgttcg    360
gctggcagaa gctatgaagc gctatgggct gaatacaaac catcggatcg tggtgtgcag    420
cgagaatagc ttgcagttct tcatgcccgt gttgggtgcc ctgttcatcg gtgtggctgt    480
ggccccagct aacgacatct acaacgagcg cgagctgctg aacagcatgg gcatcagcca    540
gcccaccgtc gtattcgtga gcaagaaagg gctgcaaaag atcctcaacg tgcaaaagaa    600
gctaccgatc atacaaaaga tcatcatcat ggatagcaag accgactacc agggcttcca    660
aagcatgtac accttcgtga cttcccattt gccacccggc ttcaacgagt acgacttcgt    720
gcccgagagc ttcgaccggg acaaaaccat cgccctgatc atgaacagta gtggcagtac    780
cggattgccc aagggcgtag ccctaccgca ccgcaccgct tgtgtccgat tcagtcatgc    840
ccgcgacccc atcttcggca accagatcat ccccgacacc gctatcctca gcgtggtgcc    900
atttcaccac ggcttcggca tgttccacac gctgggctac ttgatctgcg gctttcgggt    960
cgtgctcatg taccgcttcg aggaggagct attcttgcgc agcttgcaag actataagat   1020
tcaatctgcc ctgctggtgc ccacactatt tagcttcttc gctaagagca ctctcatcga   1080
caagtacgac ctaagcaact tgcacgagat cgccagcggg ggggcgccgc tcagcaagga   1140
ggtaggtgag gccgtggcca aacgcttcca cctaccaggc atccgccagg gctacggcct   1200
gacagaaaca accagcgcca ttctgatcac ccccgaaggg gacgacaagc ctggcgcagt   1260
aggcaaggtg gtgcccttct tcgaggctaa ggtggtggac ttggacaccg gtaagacact   1320
gggtgtgaac cagcgcggcg agctgtgcgt ccgtggcccc atgatcatga gcggctacgt   1380
taacaacccc gaggctacaa acgctctcat cgacaaggac ggctggctgc acagcggcga   1440
catcgcctac tgggacgagg acgagcactt cttcatcgtg gaccgcctga agagcctgat   1500
caaatacaag ggctaccagg tagccccagc cgaactggag agcatcctgc tgcaacaccc   1560
caacatcttc gacgccgggg tcgccggcct gcccgacgac gatgccggcg agctgcccgc   1620
cgcagtcgtc gtgctggaac acggtaaaac catgaccgag aaggagatcg tggactatgt   1680
ggccagccag gttacaaccg ccaagaagct gcgcggtggt gttgtgttcg tggacgaggt   1740
gcctaaagga ctgaccggca gttggacgcc ccgcaagatc cgcgagattc tcattaaggc   1800
caagaagggc ggcaagatcg ccgtgtaata attctagagt cggggcggcc ggccgcttcg   1860
```

```
agcagacatg ataagataca ttgatgagtt tggacaaacc acaactagaa tgcagtgaaa    1920
aaaatgcttt atttgtgaaa tttgtgatgc tattgcttta tttgtaacca ttataagctg    1980
caataaacaa gttaacaaca acaattgcat tcattttatg tttcaggttc agggggaggt    2040
gtgggaggtt ttttaaagca agtaaaacct ctacaaatgt ggtaaaatcg ataaggatcc    2100
gtttgcgtat tgggcgctct tccgctgatc tgcgcagcac catggcctga ataacctct    2160 gaaagaggaa cttggttagc taccttctga ggcggaaaga accagctgtg gaatgtgtgt    2220
cagttagggt gtggaaagtc cccaggctcc ccagcaggca gaagtatgca aagcatgcat    2280
ctcaattagt cagcaaccag gtgtggaaag tccccaggct ccccagcagg cagaagtatg    2340
caaagcatgc atctcaatta gtcagcaacc atagtcccgc ccctaactcc gcccatcccg    2400
cccctaactc cgcccagttc cgcccattct ccgccccatg gctgactaat ttttttatt    2460 tatgcagagg ccgaggccgc ctctgcctct gagctattcc agaagtagtg aggaggcttt    2520
tttggaggcc taggcttttg caaaaagctc gattcttctg acactagcgc accatgatc    2580 gaacaagacg gcctccatgc tggcagtccc gcagcttggg tcgaacgctt gttcgggtac    2640
gactgggccc agcagaccat cggatgtagc gatgcggccg tgttccgtct aagcgctcaa    2700
ggccggcccg tgctgttcgt gaagaccgac ctgagcggcg ccctgaacga gcttcaagac    2760
gaggctgccc gcctgagctg gctggccacc accggcgtac cctgcgccgc tgtgttggat    2820
gttgtgaccg aagccggccg ggactggctg ctgctgggcg aggtccctgg ccaggatctg    2880
ctgagcagcc accttgcccc cgctgagaag gtttctatca tggccgatgc aatgcggcgc    2940
ctgcacaccc tggaccccgc tacctgcccc ttcgaccacc aggctaagca tcggatcgag    3000
cgtgctcgga cccgcatgga ggccggcctg gtggaccagg acgacctgga cgaggagcat    3060
cagggcctgg cccccgctga actgttcgcc cgactgaaag cccgcatgcc ggacggtgag    3120
gacctggttg tcacacacgg agatgcctgc ctccctaaca tcatggtcga gaatggccgc    3180
ttctccggct tcatcgactg cggtcgccta ggagttgccg accgctacca ggacatcgcc    3240
ctggccaccc gcgacatcgc tgaggagctt ggcggcgagt gggccgaccg cttcttagtc    3300
ttgtacggca tcgcagctcc cgacagccag cgcatcgcct tctaccgctt gctcgacgag    3360
ttcttttaat gatctagaac cggtcatggc cgcaataaaa tatctttatt ttcattacat    3420
ctgtgtgttg gttttttgtg tgttcgaact agatgctgtc gaccgatgcc cttgagagcc    3480
ttcaacccag tcagctcctt ccggtgggcg cggggcatga ctatcgtcgc cgcacttatg    3540
actgtcttct ttatcatgca actcgtagga caggtgccgg cagcgctctt ccgcttcctc    3600
gctcactgac tcgctgcgct cggtcgttcg gctgcggcga gcggtatcag ctcactcaaa    3660
ggcggtaata cggttatcca cagaatcagg ggataacgca ggaaagaaca tgtgagcaaa    3720
aggccagcaa aaggccagga accgtaaaaa ggccgcgttg ctggcgtttt tccataggct    3780
ccgcccccct gacgagcatc acaaaaatcg acgctcaagt cagaggtggc gaaacccgac    3840
aggactataa agataccagg cgtttccccc tggaagctcc ctcgtgcgct ctcctgttcc    3900
gaccctgccg cttaccggat acctgtccgc ctttctccct tcgggaagcg tggcgctttc    3960
tcatagctca cgctgtaggt atctcagttc ggtgtaggtc gttcgctcca agctgggctg    4020
tgtgcacgaa ccccccgttc agcccgaccg ctgcgcctta tccggtaact atcgtcttga    4080
gtccaacccg gtaagacacg acttatcgcc actggcagca gccactggta acaggattag    4140
cagagcgagg tatgtaggcg gtgctacaga gttcttgaag tggtggccta actacggcta    4200
cactagaaga acagtatttg gtatctgcgc tctgctgaag ccagttacct tcggaaaaag    4260
```

```
agttggtagc tcttgatccg gcaaacaaac caccgctggt agcggtggtt ttttttgtttg    4320 caagcagcag attacgcgca gaaaaaaagg atctcaagaa gatcctttga tcttttctac    4380
ggggtctgac gctcagtgga acgaaaactc acgttaaggg attttggtca tgagattatc    4440
aaaaaggatc ttcacctaga tccttttaaa ttaaaaatga agttttaaat caatctaaag    4500
tatatatgag taaacttggt ctgacagcgg ccgcaaatgc taaaccactg cagtggttac    4560
cagtgcttga tcagtgaggc accgatctca gcgatctgcc tatttcgttc gtccatagtg    4620
gcctgactcc ccgtcgtgta gatcactacg attcgtgagg cttaccatc aggccccagc    4680 gcagcaatga tgccgcgaga ccgcgttca ccggccccg atttgtcagc aatgaaccag    4740
ccagcaggga gggccgagcg aagaagtggt cctgctactt tgtccgcctc catccagtct    4800
atgagctgct gtcgtgatgc tagagtaaga agttcgccag tgagtagttt ccgaagagtt    4860
gtggccattg ctactggcat cgtggtatca cgctcgtcgt tcggtatggc ttcgttcaac    4920
tctggttccc agcggtcaag ccgggtcaca tgatcaccca tattatgaag aaatgcagtc    4980
agctccttag ggcctccgat cgttgtcaga agtaagttgg ccgcggtgtt gtcgctcatg    5040
gtaatggcag cactacacaa ttctcttacc gtcatgccat ccgtaagatg cttttccgtg    5100
accggcgagt actcaaccaa gtcgttttgt gagtagtgta tacggcgacc aagctgctct    5160
tgcccggcgt ctatacggga caacaccgcg ccacatagca gtactttgaa agtgctcatc    5220
atcgggaatc gttcttcggg gcggaaagac tcaaggatct tgccgctatt gagatccagt    5280
tcgatatagc ccactcttgc acccagttga tcttcagcat ctttactttt caccagcgtt    5340
tcggggtgtg caaaaacagg caagcaaaat gccgcaaaga agggaatgag tgcgacacga    5400
aaatgttgga tgctcatact cgtccttttt caatattatt gaagcattta tcagggttac    5460
tagtacgtct ctcaaggata agtaagtaat attaaggtac gggaggtatt ggacaggccg    5520
caataaaata tctttatttt cattacatct gtgtgttggt tttttgtgtg aatcgatagt    5580
actaacatac gctctccatc aaaacaaaac gaaacaaaac aaactagcaa ataggctgt    5640 ccccagtgca agtgcaggtg ccagaacatt tctct                              5675
```

<210> SEQ ID NO 37
<211> LENGTH: 52
<212> TYPE: DNA
<213> ORGANISM: Artificial Sequence
<220> FEATURE:
<223> OTHER INFORMATION: Oligonucleotide PARIC1fw

<400> SEQUENCE: 37
agcttgacgt aaacgcgttc gcgaccatat gtgatcagga attctccgga ag    52

<210> SEQ ID NO 38
<211> LENGTH: 52
<212> TYPE: DNA
<213> ORGANISM: Artificial Sequence
<220> FEATURE:
<223> OTHER INFORMATION: Oligonucleotide PARIC1rv

<400> SEQUENCE: 38
gatccttccg gagaattcct gatcacatat ggtcgcgaac gcgtttacgt ca    52

<210> SEQ ID NO 39
<211> LENGTH: 32
<212> TYPE: DNA
<213> ORGANISM: Artificial Sequence
<220> FEATURE:

<223> OTHER INFORMATION: Oligonucleotide PoA-Fw

<400> SEQUENCE: 39 tttttttgaat tcgtgtaata attctagagt cg                          32

<210> SEQ ID NO 40
<211> LENGTH: 22
<212> TYPE: DNA
<213> ORGANISM: Artificial Sequence
<220> FEATURE:
<223> OTHER INFORMATION: Oligonucleotide PoA-Rv

<400> SEQUENCE: 40
ccaatacgca aacggatcct ta                                      22

<210> SEQ ID NO 41
<211> LENGTH: 6325
<212> TYPE: DNA
<213> ORGANISM: Artificial Sequence
<220> FEATURE:
<223> OTHER INFORMATION: Seq3a-IC vector

<400> SEQUENCE: 41

| | | |
|---|---|---|
| gttggttttt tgtgtgaatc gatagtacta acatacgctc tccatcaaaa caaaacgaaa | 60 |
| caaaacaaac tagcaaaata ggctgtcccc agtgcaagtg caggtgccag aacatttctc | 120 |
| tggcctaact ggccggtacc ggagaggggg taaaaaaatg ctgcactgtg cggctaggcc | 180 |
| ggtgagtgag cggcgcggag ccaatcagcg ctcgccgttc cgaaagttgc cttttatggc | 240 |
| tcgagtggcc gctgtggcgt cctataaaac cggcggcgc aacgcgcagc cactgtcgag | 300 |
| tccgcgtcca cccgcgagca caggcctttc gcagctcttt cttcgccgct ccacacccgc | 360 |
| caccaggtaa gcagggacaa caggcccagc cggccacagc cctcccgtgg gcagtgaccg | 420 |
| cgctgcaggg tcgcggggga cactcggcgc ggacaccggg gaaggctgga gggtggtgcc | 480 |
| gggccgcgga gcggacactt tcagatccaa ctttcagtcc agggtgtaga ccctttacag | 540 |
| ccgcattgcc acggtgtaga caccggtgga cccgctctgg ctcagagcac gcggcttggg | 600 |
| ggaacccatt agggtcgcag tgtgggcgct atgagagccg atgcagcttt cgggtgttga | 660 |
| accgtatctg cccaccttgg ggggaggaca caaggtcggg agccaaacgc cacgatcatg | 720 |
| ccttggtggc ccatgggtct ttgtctaaac cggtttgccc attggcttg ccgggcgggc | 780 |
| gggcgcggcg ggcccggctc ggccgggttg ggggctgggt tgccactgcg cttgcgcgct | 840 |
| ctatggctgg gtattgggc gcgtgcacgc tggggaggga gcccttcctc ttccccctct | 900 |
| cccaagttaa acttgcgcgt gcgtattgag acttggagcg cggccaccgg ggttgggcga | 960 |
| gggcggggcc gttgtccgga aggggcgggg tcgcagcggc ttcggggcgc ctgctcgcgc | 1020 |
| ttcctgctgg gtgtggtcgc ctcccgcgcg cgcactagcc gcccgccggc ggggcgaagg | 1080 |
| cggggcttgc gcccgtttgg ggaggggcg gaggcctggc ttcctgccgt ggggccgcct | 1140 |
| ccggaccagc gtttgcctct tatggtaata acgcggccgg cctgggcttc ctttgtcccc | 1200 |
| tgagtttggg cgcgcgcccc ctggcggccc gaggccgcgg cttgccggaa gtgggcaggg | 1260 |
| cggcagcggc tgcgcctagt ggcccgccag tgaccgcgac cctcttttgt gccctgatat | 1320 |
| agttcgccga attcgctagc agaacaggat gttctgatca aagagatcca aagtcagaac | 1380 |
| acgttgttct agctaaaata acacattcag agaacatgct gttctgatca aagagatcca | 1440 |
| aagtcagaac aaggtgttct agctaaaata acacattcag agaacatgat gttctgatca | 1500 |
| aagagatcca agtcgcggc cgcgttgaca ttgattattg actagttatt aatagtaatc | 1560 |

```
aattacgggg tcattagttc atagcccata tatggagttc cgcgttacat aacttacggt    1620
aaatggcccg cctggctgac cgcccaacga cccccgccca ttgacgtcaa taatgacgta    1680
tgttcccata gtaacgccaa tagggacttt ccattgacgt caatgggtgg agtatttacg    1740
gtaaactgcc cacttggcag tacatcaagt gtatcatatg ccaagtacgc ccctattga    1800 cgtcaatgac ggtaaatggc ccgcctggca ttatgcccag tacatgacct tatgggactt    1860
tcctacttgg cagtacatct acgtattagt catcgctatt accatggtga tgcggttttg    1920
gcagtacatc aatgggcgtg atagcggtt tgactcacgg ggatttccaa gtctccaccc    1980
cattgacgtc aatgggagtt tgttttggca ccaaaatcaa cgggactttc caaaatgtcg    2040
taacaactcc gccccattga cgcaaatggg cggtaggcgt gtacggtggg aggtctatat    2100
aagcagagct ctctggctaa ctagagaacc cactgcttac tggcttatcg aaagcttgac    2160
gtaaacgcgt tcgcgaccat atgtgatcag gaattcgtgt aataattcta gagtcggggc    2220
ggccggccgt tcgagcaga catgataaga tacattgatg agtttggaca aaccacaact    2280
agaatgcagt gaaaaaaatg ctttatttgt gaaatttgtg atgctattgc tttatttgta    2340
accattataa gctgcaataa acaagttaac aacaacaatt gcattcattt tatgtttcag    2400 gttcagggggg aggtgtggga ggttttttaa agcaagtaaa acctctacaa atgtggtaaa    2460
atcgataagg atccgtttgc gtattgggcg ctcttccgct gatctgcgta ataattctag    2520
agtcggggcg gccggccgct tcgagcagac atgataagat acattgatga gtttggacaa    2580
accacaacta gaatgcagtg aaaaaaatgc tttatttgtg aaatttgtga tgctattgct    2640
ttatttgtaa ccattataag ctgcaataaa caagttaaca acaacaattg cattcatttt    2700
atgtttcagg ttcaggggga ggtgtgggag gttttttaaa gcaagtaaaa cctctacaaa    2760
tgtggtaaaa tcgataagga tccgcagcac catggcctga ataacctct gaaagaggaa    2820 cttggttagc taccttctga ggcggaaaga accagctgtg gaatgtgtgt cagttagggt    2880
gtggaaagtc cccaggctcc ccagcaggca gaagtatgca aagcatgcat ctcaattagt    2940
cagcaaccag gtgtggaaag tccccaggct ccccagcagg cagaagtatg caaagcatgc    3000
atctcaatta gtcagcaacc atagtcccgc ccctaactcc gcccatcccg ccctaactc    3060 cgcccagttc cgcccattct ccgccccatg gctgactaat tttttttatt tatgcagagg    3120
ccgaggccgc ctctgcctct gagctattcc agaagtagtg aggaggcttt tttggaggcc    3180
taggcttttg caaaaagctc gattcttctg acactagcgc caccatgatc gaacaagacg    3240
gcctccatgc tggcagtccc gcagcttggg tcgaacgctt gttcgggtac gactgggccc    3300
agcagaccat cggatgtagc gatgcggccg tgttccgtct aagcgctcaa ggccggcccg    3360
tgctgttcgt gaagaccgac ctgagcggcg ccctgaacga gcttcaagac gaggctgccc    3420
gcctgagctg gctggccacc accggcgtac cctgcgccgc tgtgttggat gttgtgaccg    3480
aagccggccg ggactggctg ctgctgggcg aggtccctgg ccaggatctg ctgagcagcc    3540
accttgcccc cgctgagaag gtttctatca tggccgatgc aatgcggcgc ctgcacaccc    3600
tggaccccgc tacctgcccc ttcgaccacc aggctaagca tcggatcgag cgtgctcgga    3660
cccgcatgga ggcggcctg gtggaccagg acgacctgga cgaggagcat caggggctgg    3720
cccccgctga actgttcgcc cgactgaaag cccgcatgcc ggacggtgag gacctggttg    3780
tcacacacgg agatgcctgc ctccctaaca tcatggtcga gaatggccgc ttctccggct    3840
tcatcgactg cggtcgccta ggagttgccg accgctacca ggacatcgcc ctggccaccc    3900
```

```
gcgacatcgc tgaggagctt ggcggcgagt gggccgaccg cttcttagtc ttgtacggca   3960
tcgcagctcc cgacagccag cgcatcgcct tctaccgctt gctcgacgag ttcttttaat   4020
gatctagaac cggtcatggc cgcaataaaa tatctttatt ttcattacat ctgtgtgttg   4080
gttttttgtg tgttcgaact agatgctgtc gaccgatgcc cttgagagcc ttcaacccag   4140
tcagctcctt ccggtgggcg cggggcatga ctatcgtcgc cgcacttatg actgtcttct   4200
ttatcatgca actcgtagga caggtgccgg cagcgctctt ccgcttcctc gctcactgac   4260
tcgctgcgct cggtcgttcg gctgcggcga gcggtatcag ctcactcaaa ggcggtaata   4320
cggttatcca cagaatcagg ggataacgca ggaaagaaca tgtgagcaaa aggccagcaa   4380
aaggccagga accgtaaaaa ggccgcgttg ctggcgtttt tccataggct ccgcccccct   4440
gacgagcatc acaaaaatcg acgctcaagt cagaggtggc gaaacccgac aggactataa   4500
agataccagg cgtttccccc tggaagctcc ctcgtgcgct ctcctgttcc gaccctgccg   4560
cttaccggat acctgtccgc ctttctccct tcgggaagcg tggcgctttc tcatagctca   4620
cgctgtaggt atctcagttc ggtgtaggtc gttcgctcca agctgggctg tgtgcacgaa   4680
ccccccgttc agcccgaccg ctgcgcctta tccggtaact atcgtcttga gtccaacccg   4740
gtaagacacg acttatcgcc actggcagca gccactggta acaggattag cagagcgagg   4800
tatgtaggcg gtgctacaga gttcttgaag tggtggccta actacggcta cactagaaga   4860
acagtatttg gtatctgcgc tctgctgaag ccagttacct tcggaaaaag agttggtagc   4920
tcttgatccg gcaaacaaac caccgctggt agcggtggtt ttttgtttg caagcagcag   4980 attacgcgca gaaaaaagg atctcaagaa gatcctttga tcttttctac ggggtctgac   5040
gctcagtgga acgaaaactc acgttaaggg attttggtca tgagattatc aaaaaggatc   5100
ttcacctaga tccttttaaa ttaaaaatga agttttaaat caatctaaag tatatatgag   5160
taaacttggt ctgacagcgg ccgcaaatgc taaaccactg cagtggttac cagtgcttga   5220
tcagtgaggc accgatctca gcgatctgcc tatttcgttc gtccatagtg gcctgactcc   5280
ccgtcgtgta gatcactacg attcgtgagg gcttaccatc aggccccagc gcagcaatga   5340
tgccgcgaga gccgcgttca ccggcccccg atttgtcagc aatgaaccag ccagcaggga   5400
gggccgagcg aagaagtggt cctgctactt tgtccgcctc catccagtct atgagctgct   5460
gtcgtgatgc tagagtaaga agttcgccag tgagtagttt ccgaagagtt gtggccattg   5520
ctactggcat cgtggtatca cgctcgtcgt tcggtatggc ttcgttcaac tctggttccc   5580
agcggtcaag ccgggtcaca tgatcaccca tattatgaag aaatgcagtc agctccttag   5640
ggcctccgat cgttgtcaga agtaagttgg ccgcggtgtt gtcgctcatg gtaatggcag   5700
cactacacaa ttctcttacc gtcatgccat ccgtaagatg cttttccgtg accggcgagt   5760
actcaaccaa gtcgttttgt gagtagtgta tacggcgacc aagctgctct tgcccggcgt   5820
ctatacggga caacaccgcg ccacatagca gtactttgaa agtgctcatc atcgggaatc   5880
gttcttcggg gcggaaagac tcaaggatct tgccgctatt gagatccagt tcgatatagc   5940
ccactcttgc acccagttga tcttcagcat cttttacttt caccagcgtt tcggggtgtg   6000
caaaaacagg caagcaaaat gccgcaaaga agggaatgag tgcgacacga aaatgttgga   6060
tgctcatact cgtcctttt caatattatt gaagcattta tcagggttac tagtacgtct   6120
ctcaaggata agtaagtaat attaaggtac gggaggtatt ggacaggccg caataaaata   6180
tctttatttt cattacatct gtgtgttggt ttttgtgtg aatcgatagt actaacatac   6240
gctctccatc aaaacaaaac gaaacaaaac aaactagcaa aataggctgt ccccagtgca   6300
```

| | |
|---|---|
| agtgcaggtg ccagaacatt tctct | 6325 |

<210> SEQ ID NO 42
<211> LENGTH: 30
<212> TYPE: DNA
<213> ORGANISM: Artificial Sequence
<220> FEATURE:
<223> OTHER INFORMATION: Oligonucleotide HTNFHind3-Fv

<400> SEQUENCE: 42

| | |
|---|---|
| aagctgaagc ttcaccatgg cctgggtgtg | 30 |

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide RitH-Mlu1Rv

<400> SEQUENCE: 43

| | |
|---|---|
| gagctcacgc gttcatttac ccggagacag | 30 |

<210> SEQ ID NO 44
<211> LENGTH: 6794
<212> TYPE: DNA
<213> ORGANISM: Artificial Sequence
<220> FEATURE:
<223> OTHER INFORMATION: pHQG9 vector

<400> SEQUENCE: 44

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| caccatggcc tgggtgtgga ccttgctttt cctgatgaca gctgcccaga gtgcccaagc | 960 |
| acagatccag ttggaacagt ctggacctga gctgaagaag cctggagaga cagtcaagat | 1020 |
| ctcctgcaag gcttctggat atatcttcac aaacaatgga atgagctggg tgaaacaggc | 1080 |
| tccaggaaag ggtttaaagt ggatgggctg ggtaaacacc tacactggta agtcaacata | 1140 |
| tgctgatgac ttcaagggac ggtttgcctt ctctttggaa acctcagcca gcactgccta | 1200 |
| tttgcaaatc aacaacctca aaaatgagga cacggctaca tatttctgtg caagagactc | 1260 |

-continued

```
tactacggta ataqctacga atgctatgga cttctggggt caaggaacct cagtcaccgt   1320
ctcctcagcc tcaaccaagg gcccatcggt cttccccctg gcaccctcct ccaagagcac   1380
ctctggqggc acagcggccc tgggctgcct ggtcaaggac tacttccccg aaccggtgac   1440
ggtgtcgtgg aactcaggcg ccctgaccag cggcgtgcac accttcccgg ctgtcctaca   1500
gtcctcagga ctctactccc tcagcagcgt ggtgaccgtg ccctccagca gcttgggcac   1560
ccagacctac atctgcaacg tgaatcacaa gcccagcaac accaaggtgg acaagaaagt   1620
tgagcccaaa tcttgtgaca aaactcacac atgcccaccg tgcccagcac ctgaactcct   1680
ggggggaccg tcagtcttcc tcttccccce aaaacccaag gacaccctca tgatctcccg   1740
gacccctgag gtcacatgcg tggtggtgga cgtgagccac gaagaccctg aggtcaagtt   1800
caactggtac gtggacggcg tggaggtgca taatgccaag acaaagccgc gggaggagca   1860
gtacaacagc acgtaccgtg tggtcagcgt cctcaccgtc ctgcaccagg actggctgaa   1920
tggcaaggag tacaagtgca aggtctccaa caaagccctc ccagccccca tcgagaaaac   1980
catctccaaa gccaaagggc agccccgaga accacaggtg tacaccctgc ccccatcccg   2040
ggatgagctg accaagaacc aggtcagcct gacctgcctg gtcaaaggct tctatcccag   2100
cgacatcgcc gtggagtggg agagcaatgg gcagccggag aacaactaca agaccacgcc   2160
tcccgttctg gactccgacg gctccttctt cctctacagc aagctcaccg tggacaagag   2220
caggtggcag caggggaacg tcttctcatg ctccgtgatg catgaggctc tgcacaacca   2280
ctacacacag aagagcctct ccctgtctcc gggtaaatga ggatcccacc acactggact   2340
agtggatccg agctcggtac caagcttaag tttaaaccgc tgatcagcct cgactgtgcc   2400
ttctagttgc cagccatctg ttgtttgccc ctcccccgtg ccttccttga ccctggaagg   2460
tgccactccc actgtccttt cctaataaaa tgaggaaatt gcatcgcatt gtctgagtag   2520
gtgtcattct attctggggg gtggggtggg gcaggacagc aaggggggagg attgggaaga   2580
caatagcagg catgctgggg atgcggtggg ctctatggct tctgaggcgg aaagaaccag   2640
ctggggctct agggggtatc cccacgcgcc ctgtagcggc gcattaagcg cggcgggtgt   2700
ggtggttacg cgcagcgtga ccgctacact tgccagcgcc ctagcgcccg ctcctttcgc   2760
tttcttccct tcctttctcg ccacgttcgc cggctttccc cgtcaagctc taaatcgggg   2820
gctccctttta gggttccgat ttagtgcttt acggcacctc gaccccaaaa aacttgatta   2880
gggtgatggt tcacgtagtg gccatcgccc tgatagacg gttttttcgcc ctttgacgtt   2940
ggagtccacg ttctttaata gtggactctt gttccaaact ggaacaacac tcaaccctat   3000
ctcggtctat tcttttgatt tataagggat tttgccgatt tcggcctatt ggttaaaaaa   3060
tgagctgatt taacaaaaat ttaacgcgaa ttaattctgt ggaatgtgtg tcagttaggg   3120
tgtggaaagt ccccaggctc cccagcaggc agaagtatgc aaagcatgca tctcaattag   3180
tcagcaacca ggtgtggaaa gtccccaggc tccccagcag gcagaagtat gcaaagcatg   3240
catctcaatt agtcagcaac catagtcccg cccctaactc cgcccatccc gcccctaact   3300
ccgcccagtt ccgcccattc tccgccccat ggctgactaa ttttttttat ttatgcagag   3360
gccgaggccg cctctgcctc tgagctattc cagaagtagt gaggaggctt ttttggaggc   3420
ctaggctttt gcaaaaagct cccgggagct gtatatccat ttttcggatc tgatcaagag   3480
acaggatgag gatcgtttcg catgattgaa caagatggat tgcacgcagg ttctccggcc   3540
gcttgggtgg agaggctatt cggctatgac tgggcacaac agacaatcgg ctgctctgat   3600
gccgccgtgt tccggctgtc agcgcagggg cgcccggttc ttttttgtcaa gaccgacctg   3660
```

```
tccggtgccc tgaatgaact gcaggacgag gcagcgcggc tatcgtggct ggccacgacg    3720
ggcgttcctt gcgcagctgt gctcgacgtt gtcactgaag cgggaaggga ctggctgcta    3780
ttgggcgaag tgccggggca ggatctcctg tcatctcacc ttgctcctgc cgagaaagta    3840
tccatcatgg ctgatgcaat gcggcggctg catacgcttg atccggctac ctgcccattc    3900
gaccaccaag cgaaacatcg catcgagcga gcacgtactc ggatggaagc cggtcttgtc    3960
gatcaggatg atctggacga agagcatcag gggctcgcgc cagccgaact gttcgccagg    4020
ctcaaggcgc gcatgcccga cggcgaggat ctcgtcgtga cccatggcga tgcctgcttg    4080
ccgaatatca tggtggaaaa tggccgcttt tctggattca tcgactgtgg ccggctgggt    4140
gtggcggacc gctatcagga catagcgttg gctaccgtg atattgctga agagcttggc    4200
ggcgaatggg ctgaccgctt cctcgtgctt tacggtatcg ccgctcccga ttcgcagcgc    4260
atcgccttct atcgccttct tgacgagttc ttctgagcgg gactctgggg ttcgaaatga    4320
ccgaccaagc gacgcccaac ctgccatcac gagatttcga ttccaccgcc gccttctatg    4380
aaaggttggg cttcggaatc gttttccggg acgccggctg gatgatcctc cagcgcgggg    4440
atctcatgct ggagttcttc gcccacccca acttgtttat tgcagcttat aatggttaca    4500
aataaagcaa tagcatcaca aatttcacaa ataaagcatt tttttcactg cattctagtt    4560
gtggtttgtc caaactcatc aatgtatctt atcatgtctg tataccgtcg acctctagct    4620
agagcttggc gtaatcatgg tcatagctgt ttcctgtgtg aaattgttat ccgctcacaa    4680
ttccacacaa catacgagcc ggaagcataa agtgtaaagc ctggggtgcc taatgagtga    4740
gctaactcac attaattgcg ttgcgctcac tgcccgcttt ccagtcggga aacctgtcgt    4800
gccagctgca ttaatgaatc ggccaacgcg cggggagagg cggtttgcgt attgggcgct    4860
cttccgcttc ctcgctcact gactcgctgc gctcggtcgt tcggctgcgg cgagcggtat    4920
cagctcactc aaaggcggta atacggttat ccacagaatc aggggataac gcaggaaaga    4980
acatgtgagc aaaaggccag caaaaggcca ggaaccgtaa aaaggccgcg ttgctggcgt    5040
ttttccatag gctccgcccc cctgacgagc atcacaaaaa tcgacgctca agtcagaggt    5100
ggcgaaaccc gacaggacta taaagatacc aggcgtttcc ccctggaagc tccctcgtgc    5160
gctctcctgt tccgaccctg ccgcttaccg gatacctgtc cgcctttctc ccttcgggaa    5220
gcgtggcgct ttctcatagc tcacgctgta ggtatctcag ttcggtgtag tcgttcgct    5280
ccaagctggg ctgtgtgcac gaaccccccg ttcagcccga ccgctgcgcc ttatccggta    5340
actatcgtct tgagtccaac ccggtaagac acgacttatc gccactggca gcagccactg    5400
gtaacaggat tagcagagcg aggtatgtag gcggtgctac agagttcttg aagtggtggc    5460
ctaactacgg ctacactaga agaacagtat ttggtatctg cgctctgctg aagccagtta    5520
ccttcggaaa aagagttggt agctcttgat ccggcaaaca aaccaccgct ggtagcggtt    5580
tttttgtttg caagcagcag attacgcgca gaaaaaaagg atctcaagaa gatcctttga    5640
tcttttctac ggggtctgac gctcagtgga acgaaaactc acgttaaggg attttggtca    5700
tgagattatc aaaaaggatc ttcacctaga tccttttaaa ttaaaaatga agttttaaat    5760
caatctaaag tatatatgag taaacttggt ctgacagtta ccaatgctta atcagtgagg    5820
cacctatctc agcgatctgt ctatttcgtt catccatagt tgcctgactc cccgtcgtgt    5880
agataactac gatacgggag ggcttaccat ctggccccag tgctgcaatg ataccgcgag    5940
acccacgctc accggctcca gatttatcag caataaacca gccagccgga agggccgagc    6000
```

```
gcagaagtgg tcctgcaact ttatccgcct ccatccagtc tattaattgt tgccgggaag    6060
ctagagtaag tagttcgcca gttaatagtt tgcgcaacgt tgttgccatt gctacaggca    6120
tcgtggtgtc acgctcgtcg tttggtatgg cttcattcag ctccggttcc caacgatcaa    6180
ggcgagttac atgatccccc atgttgtgca aaaaagcggt tagctccttc ggtcctccga    6240
tcgttgtcag aagtaagttg gccgcagtgt tatcactcat ggttatggca gcactgcata    6300
attctcttac tgtcatgcca tccgtaagat gcttttctgt gactggtgag tactcaacca    6360
agtcattctg agaatagtgt atgcggcgac cgagttgctc ttgcccggcg tcaatacggg    6420
ataataccgc gccacatagc agaactttaa aagtgctcat cattggaaaa cgttcttcgg    6480
ggcgaaaact ctcaaggatc ttaccgctgt tgagatccag ttcgatgtaa cccactcgtg    6540
cacccaactg atcttcagca tcttttactt tcaccagcgt ttctgggtga gcaaaaacag    6600
gaaggcaaaa tgccgcaaaa aagggaataa gggcgacacg gaaatgttga atactcatac    6660
tcttcctttt tcaatattat tgaagcattt atcagggtta ttgtctcatg agcggataca    6720
tatttgaatg tatttagaaa aataaacaaa taggggttcc gcgcacattt ccccgaaaag    6780
tgccacctga cgtc                                                       6794

<210> SEQ ID NO 45
<211> LENGTH: 5775
<212> TYPE: DNA
<213> ORGANISM: Artificial Sequence
<220> FEATURE:
<223> OTHER INFORMATION: pKQG9 vector

<400> SEQUENCE: 45
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
aacatggatt cacaggccca ggttcttata ttgctgctgc tatgggtatc tggtacctgt    960
ggggacattg tgatgtcaca gtctccatcc tccctgctg tgtcagcagg agagaaggtc    1020
actatgagct gcaaatccag tcagagtctg ctcaacagta aacccgaaa gaactacttg    1080 gcttggtacc agcagaaacc agggcagtct cctaaactgc tgatctactg ggcatccatt    1140
agggaatctg ggtccctga tcgcttcaca ggcagtggat ctgggacaga tttcactctc    1200
accatcagca gtgtgcaggc tgaagacctg gcagtttatt actgcaagca atcttataat    1260
```

```
ctgtggacgt tcggtggagg caccaagctg gaaatcaaac ggactgttgc ggcaccatct    1320
gtcttcatct tcccgccatc tgatgagcag ttgaaatctg gaactgcctc tgttgtgtgc    1380
ctgctgaata acttctatcc cagagaggcc aaagtacagt ggaaggtgga taacgccctc    1440
caatcgggta actcccagga gagtgtcaca gagcaggaca gcaaggacag cacctacagc    1500
ctcagcagca ccctgacgct gagcaaagca gactacgaga acacaaaagt ctacgcctgc    1560
gaagtcaccc atcagggcct gagctcgccc gtcacaaaga gcttcaacag gggagagtgt    1620
tgaggatcca ctagtccagt gtggtggaat tctgcagata tccagcacag tggcggccgc    1680
tcgagtctag agggcccgaa caaaaactca tctcagaaga ggatctgaat agcgccgtcg    1740
accatcatca tcatcatcat tgagtttaaa cccgctgatc agcctcgact gtgccttcta    1800
gttgccagcc atctgttgtt tgcccctccc ccgtgccttc cttgaccctg gaaggtgcca    1860
ctcccactgt cctttcctaa taaaatgagg aaattgcatc gcattgtctg agtaggtgtc    1920
attctattct ggggggtggg gtggggcagg acagcaaggg ggaggattgg gaagacaata    1980
gcaggcatgc tggggatgcg gtgggctcta tggcttctga ggcggaaaga accagctggg    2040
gctctagggg gtatcccccac gcgccctgta gcggcgcatt aagcgcggcg ggtgtggtgg    2100
ttacgcgcag cgtgaccgct acacttgcca gcgccctagc gcccgctcct ttcgctttct    2160
tcccttcctt tctcgccacg ttcgccggct ttccccgtca agctctaaat cggggcatcc    2220
ctttagggtt ccgatttagt gctttacggc acctcgaccc caaaaaactt gattagggtg    2280
atggttcacg tagtgggcca tcgccctgat agacggtttt tcgccctttg acgttggagt    2340
ccacgttctt taatagtgga ctcttgttcc aaactggaac aacactcaac cctatctcgg    2400
tctattcttt tgatttataa gggattttgg ggatttcggc ctattggtta aaaaatgagc    2460
tgatttaaca aaaatttaac gcgaattaat tctgtggaat gtgtgtcagt tagggtgtgg    2520
aaagtcccca ggctcccccag caggcagaag tatgcaaagc atgcatctca attagtcagc    2580
aaccaggtgt ggaaagtccc caggctcccc agcaggcaga agtatgcaaa gcatgcatct    2640
caattagtca gcaaccatag tcccgcccct aactccgccc atcccgcccc taactccgcc    2700
cagttccgcc cattctccgc cccatggctg actaattttt tttatttatg cagaggccga    2760
ggccgcctct gcctctgagc tattccagaa gtagtgagga ggcttttttg gaggcctagg    2820
cttttgcaaa aagctcccgg gagcttgtat atccattttc ggatctgatc agcacgtgtt    2880
gacaattaat catcggcata gtatatcggc atagtataat acgacaaggt gaggaactaa    2940
accatggcca agttgaccag tgccgttccg gtgctcaccg cgcgcgacgt cgccggagcg    3000
gtcgagttct ggaccgaccg gctcgggttc tcccgggact tcgtggagga cgacttcgcc    3060
ggtgtggtcc gggacgacgt gaccctgttc atcagcgcgg tccaggacca ggtggtgccg    3120
gacaacaccc tggcctgggt gtgggtgcgc ggcctggacg agctgtacgc cgagtggtcg    3180
gaggtcgtgt ccacgaactt ccgggacgcc tccggcccgg ccatgaccga tcggcgag    3240 cagccgtggg ggcgggagtt cgccctgcgc gacccggccg gcaactgcgt gcacttcgtg    3300
gccgaggagc aggactgaca cgtgctacga gatttcgatt ccaccgccgc cttctatgaa    3360
aggttgggct tcggaatcgt tttccgggac gccggctgga tgatcctcca gcgcgggat    3420 ctcatgctgg agttcttcgc ccaccccaac ttgtttattg cagcttataa tggttacaaa    3480
taaagcaata gcatcacaaa tttcacaaat aaagcatttt tttcactgca ttctagttgt    3540
ggtttgtcca aactcatcaa tgtatcttat catgtctgta taccgtcgac ctctagctag    3600
```

```
agcttggcgt aatcatggtc atagctgttt cctgtgtgaa attgttatcc gctcacaatt   3660
ccacacaaca tacgagccgg aagcataaag tgtaaagcct ggggtgccta atgagtgagc   3720
taactcacat taattgcgtt gcgctcactg cccgctttcc agtcgggaaa cctgtcgtgc   3780
cagctgcatt aatgaatcgg ccaacgcgcg gggagaggcg gtttgcgtat tgggcgctct   3840
tccgcttcct cgctcactga ctcgctgcgc tcggtcgttc ggctgcggcg agcggtatca   3900
gctcactcaa aggcggtaat acggttatcc acagaatcag gggataacgc aggaaagaac   3960
atgtgagcaa aaggccagca aaaggccagg aaccgtaaaa aggccgcgtt gctggcgttt   4020
ttccataggc tccgcccccc tgacgagcat cacaaaaatc gacgctcaag tcagaggtgg   4080
cgaaacccga caggactata aagataccag gcgtttcccc ctggaagctc cctcgtgcgc   4140
tctcctgttc cgaccctgcc gcttaccgga tacctgtccg cctttctccc ttcgggaagc   4200
gtggcgcttt ctcaatgctc acgctgtagg tatctcagtt cggtgtaggt cgttcgctcc   4260
aagctgggct gtgtgcacga accccccgtt cagcccgacc gctgcgcctt atccggtaac   4320
tatcgtcttg agtccaaccc ggtaagacac gacttatcgc cactggcagc agccactggt   4380
aacaggatta gcagagcgag gtatgtaggc ggtgctacag agttcttgaa gtggtggcct   4440
aactacggct acactagaag gacagtattt ggtatctgcg ctctgctgaa gccagttacc   4500
ttcggaaaaa gagttggtag ctcttgatcc ggcaaacaaa ccaccgctgg tagcggtggt   4560
ttttttgttt gcaagcagca gattacgcgc agaaaaaaag gatctcaaga agatcctttg   4620
atcttttcta cggggtctga cgctcagtgg aacgaaaact cacgttaagg gattttggtc   4680
atgagattat caaaaaggat cttcacctag atccttttaa attaaaaatg aagttttaaa   4740
tcaatctaaa gtatatatga gtaaacttgg tctgacagtt accaatgctt aatcagtgag   4800
gcacctatct cagcgatctg tctatttcgt tcatccatag ttgcctgact ccccgtcgtg   4860
tagataacta cgatacggga gggcttacca tctggcccca gtgctgcaat gataccgcga   4920
gacccacgct caccggctcc agatttatca gcaataaacc agccagccgg aagggccgag   4980
cgcagaagtg gtcctgcaac tttatccgcc tccatccagt ctattaattg ttgccgggaa   5040
gctagagtaa gtagttcgcc agttaatagt ttgcgcaacg ttgttgccat tgctacaggc   5100
atcgtggtgt cacgctcgtc gtttggtatg gcttcattca gctccggttc caacgatca   5160 aggcgagtta catgatcccc catgttgtgc aaaaaagcgg ttagctcctt cggtcctccg   5220
atcgttgtca gaagtaagtt ggccgcagtg ttatcactca tggttatggc agcactgcat   5280
aattctctta ctgtcatgcc atccgtaaga tgcttttctg tgactggtga gtactcaacc   5340
aagtcattct gagaatagtg tatgcggcga ccgagttgct cttgcccggc gtcaatacgg   5400
gataataccg cgccacatag cagaacttta aaagtgctca tcattggaaa acgttcttcg   5460
gggcgaaaac tctcaaggat cttaccgctg ttgagatcca gttcgatgta acccactcgt   5520
gcacccaact gatcttcagc atcttttact ttcaccagcg tttctgggtg agcaaaaaca   5580
ggaaggcaaa atgccgcaaa aaagggaata agggcgacac ggaaatgttg aatactcata   5640
ctcttccttt ttcaatatta ttgaagcatt tatcagggtt attgtctcat gagcggatac   5700
atatttgaat gtatttagaa aaataaacaa ataggggttc cgcgcacatt tccccgaaaa   5760
gtgccacctg acgtc                                                    5775
```